US008772048B2

(12) United States Patent
Twieg et al.

(10) Patent No.: US 8,772,048 B2
(45) Date of Patent: Jul. 8, 2014

(54) FLUOROGENIC COMPOUNDS CONVERTED TO FLUOROPHORES BY PHOTOCHEMICAL OR CHEMICAL MEANS AND THEIR USE IN BIOLOGICAL SYSTEMS

(75) Inventors: Robert J. Twieg, Kent, OH (US); William E. Moerner, Los Altos, CA (US); Samuel J. Lord, Palo Alto, CA (US); Na Liu, Bloomfield, CT (US); Reichel Samuel, Atlanta, GA (US)

(73) Assignees: Kent State University, Kent, OH (US); Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/409,818

(22) Filed: Mar. 1, 2012

(65) Prior Publication Data
US 2012/0190098 A1 Jul. 26, 2012

Related U.S. Application Data

(62) Division of application No. 12/454,273, filed on May 13, 2009, now Pat. No. 8,153,446.

(60) Provisional application No. 61/128,729, filed on May 23, 2008.

(51) Int. Cl.
*G01N 33/533* (2006.01)
*G01N 33/532* (2006.01)
*C07K 1/10* (2006.01)

(52) U.S. Cl.
USPC ............ 436/546; 436/544; 530/402; 530/405

(58) Field of Classification Search
None
See application file for complete search history.

(56) References Cited

U.S. PATENT DOCUMENTS

| 5,670,091 | A | 9/1997 | Marder et al. |
| 5,679,763 | A | 10/1997 | Jen et al. |
| 6,090,332 | A | 7/2000 | Marder et al. |
| 6,716,995 | B2 | 4/2004 | Zhu et al. |
| 6,750,603 | B2 | 6/2004 | Huang et al. |
| 6,864,375 | B2 | 3/2005 | Huang et al. |
| 7,507,840 | B2 | 3/2009 | Dalton et al. |
| 2005/0009109 | A1 | 1/2005 | Moerner et al. |

OTHER PUBLICATIONS

Leyva et al. Photochemistry of phenyl azide: the role of singlet and triplet phenylnitrene as transient intermediates. J. Am. Chem. Soc. 1986, vol. 108, No. 13, pp. 3783-3790.*
Betzig, E. et al., Imaging Intracellular Fluorescent Proteins . . . , Science, 2006, vol. 313, pp. 1642-1645, www.sciencemag.org.
Hess, S.T., et al., Ultra-High Resolution Imaging by Fluorescent Photoactivation . . . , Biophys. J., 2006, vol. 91, pp. 4258-4272, Biophysical Society.

(Continued)

*Primary Examiner* — Shafiqul Haq
(74) *Attorney, Agent, or Firm* — Hudak, Shunk & Farine Co. LPA

(57) ABSTRACT

Fluorophores derived from photoactivatable azide-pi-acceptor fluorogens or from a thermal reaction of an azide-pi-acceptor fluorogen with an alkene or alkyne are disclosed. Fluorophores derived from a thermal reaction of an alkyne-pi-acceptor fluorogen with an azide are also disclosed. The fluorophores can readily be activated by light and can be used to label a biomolecule and imaged on a single-molecule level in living cells.

12 Claims, 19 Drawing Sheets

(56) References Cited

OTHER PUBLICATIONS

Rust, M., et al., Sub-diffraction-limit imaging by stochastic optical . . . , Nature Meth., Oct. 2006, vol. 3, No. 10, pp. 793-795, published online.
Moerner, W. E., New directions in single-molecule imaging . . . , Proc. Nat. Acad. Sci. (USA), 2007, vol. 104, No. 31, pp. 12596-12602, published online.
Heileman, M., Photoswitches: Key Molecules for subdiffraction-resolution . . . , Laser & Photonics Reviews, 2009, Rev. 3, No. 1-2, pp. 180-202, published online.
Fernandez-Suarez, M, et al., Fluorescent probes for super-resolution . . . , Nature Reviews/Molecular Cell Biology, Dec. 2008, vol. 9, pp. 929-943, Macmillan Publishers Limited.
Thompson, R.E., et al., Precise Nanometer Localization Analysis . . . , Biophys. J., May 2002, vol. 82, pp. 2775-2783, Biophysical Society.
Ando, R, et al., Regulated Fast Nucleocytoplasmic Shuttling . . . , Science, Nov. 2004, vol. 306, pp. 1370-1373, www.sciencemag.org.
Patterson, G.H., et al., A Photoactivatable GFP for Selective . . . , Science, Sep. 2002, vol. 297, pp. 1873-1877, www.sciencemag.org.
Harms, G.S., et al., Autofluorescent Proteins in Single-Molecule Research: . . . , Biophys. J. May 2001, vol. 80, pp. 2396-2408, Biophysical Society.
Chen, L, et al, Site-specific labeling of proteins with small molecules . . . , Curr. Opin. Biotech., 2005, vol. 16, pp. 35-40, www.sciencedirect.com.
Prescher, J.A., et al., Chemistry in living systems, Nat. Chem. Biol., Jun. 2005, No. 1, pp. 13-21, Nature Publishing Group.
Adams, S.R., et al., New Biarsenical Ligands and Tetracysteine . . . , J. Am. Chem, Soc., May 2002, 124, pp. 6063-6076, published online.
Bates, M., et al., Short-Range Spectroscopic Ruler . . . , Phys. Rev. Lett., Mar. 2005, 94, pp. 108101-1-108101-4, The American Physical Society.
Folling, J., et al., Photochromic Rhodamines Provide Nanoscopy . . . , Chem. Int. Ed., 2007, 46, 6266-6270, Wiley-VCH Verlag GmbH & Co, Weinheim.
Lord, S. J., et. al., a Photoactivatable Push-Pull Fluorophore . . . , 2008, J. Amer. Chem. Soc., 130, pp. 9204-9205, American Chemical Society.
Dreyfuss, G., et al., Fluorescent photoaffinity labeling: Adenosine . . . , Proceedings of the National Academy of Sciences, Mar. 1978, vol. 75, No. 3, pp. 1199-1203.
Moreland, et al. Preparation and Characterization of 3-Azido-2,7-Naphthalene . . . , Anal. Biochem., 1980, 103, pp. 26-32, Academic Press, Inc.
Thevenin, B., et al., A novel photoactivatable cross-linker for the functionally—. . . , Eur. J. Biochem. 1992, 206, pp. 471-477, FEBS.
Ahlheim, M, et al., Chromophores with Strong Heterocyclic Acceptors: A Poled Polymer . . . , Science Jan. 1996, vol. 271, pp. 335-337, published online.
Milian, B, et al., Spectroscopic and Theoretical Study of Push-Pull Chromophores Containing . . . , J. Phys. Chem. B 2003, 107, pp. 12175-12183, published on web.
Los, G.V., et al., Halotag Interchangeable Labeling Technology . . . , Cell Notes, 2005, Issue 11, pp. 2-6.
Keppler, A., et al., A general method for the covalent labeling of fusion proteins . . . , Nat Biotech, 2003, vol. 21, pp. 86-89, Nature Publishing Group.
Scheiner, P., et. al., The Addition of Aryl Azides to Norbornene . . . , Jan. 1965, J. Amer. Chem. Soc., 87:2, pp. 306-311.
Oehlschlager, A.C., et. al., Reaction of methyl azidoformate with norbornene, 1969, Can. J. Chem., 47, pp. 4367-4374.
Hermes, M.E., et al., N-Cyanoaziridines and 1-Alkylalkylidenecyanamides . . . , 1972, J. Org. Chem., vol. 37, No. 19, pp. 2969-2979.
Huisgen, R., et. al., Exceptional Reactivity of the Bicyclo[2.2.1]heptene Double Bond, May 1980, J. Amer. Chem. Soc., 102:11, pp. 3951-3953, American Chemical Society.
Shea, K. J. , et al., Influence of Strain on Chemical Reactivity. Relative Reactivity . . . , 1992, J. Amer. Chem. Soc., 114, pp. 4846-4855, American Chemical Society.
Brase, S., et. al., Cycloaddition Reactions of Azides Including Bioconjugation, 2008, Topics in Heterocyclic Chemistry, 12, pp. 45-115, published online.
Baskin, J. M. et al., Bioorthogonal Click Chemistry: Covalent Labeling . . . , 2007, QSAR Comb. Sci., vol. 26, No. 11-12, pp. 1211-1219, Wiley-VCH Verlag GmbH & Co.
Lord, S. J., et. al., DCDHF Flurorphores for Single-Molecule Imaging in Cells, ChemPhysChem, 2009, Vo. 10, pp. 55-65, Wiley-VCH Verlag GmbH & Co.
Ostrovherkova, O., et al., Role of Temperature in Controlling Performance of Photorefractive Organic Glasses, 2003 ChemPhysChem, 4, pp. 732-744, Wiley-VCH Verlag GmbH & Co.
Andreu, R., et. al., Decreased Optical Nonlinearities upon CF3 Substitution . . . , Org. Lett., 2008, vol. 10, No. 21, pp. 4963-4966, published on web.
Zhang, C., et. al., Low V Electrooptic Modulators for CLD-1: Chromophore Design . . . , Chem. Mater., 2001, 13, pp. 3043-3050, published on web.
Nakanishi, J., et. al., Imaging of Conformational Changes of Proteins with a New Environment-Sensitive . . . , 2001, Anal. Chem., 73, pp. 2920-2928, published on web.
Meier, H., et. al., Push-Pull Oligomers with 2,2-Dicyanovinyl Groups . . . , 2007, Eur. J. Org. Chem., pp. 625-631, Wiley-VCH Verlag GmbH & Co.
Zhao, C. Y., et. al., A Theoretical Study on the Hyperpolarizabilities of dicyanovinyl . . . , 1996, Theochem-Journal Mol. Struct., 367, pp. 73-82.
Meyer, M. et al., Ground State and Singlet Excited State of Laser Dye DCM: . . . , 1987, Opt. Comm., vol. 64, No. 3, pp. 264-268, Elsevier Science Publishers B.V.
Moylan, C. R., et. al., (Dicyanomethylene)pyran Derivatives with C2v Symmetry: . . . , 1996, J. Amer. Chem. Soc., 118, pp. 12950-12955.
Onoda, M., et al., The effects of spacer length on the fluorescence quantum yields . . . , 2002, Luminescence, 17, pp. 11-14, John Wiley & Sons, Ltd.
Marder, S. R., 4-N-Methylstilbazolium Toluene-p-sulfonate Salts . . . , 1992, J. Mater. Chem., 2(9), pp. 985-986.
Schafer, F. R, Principles of Dye Laser Operation, Topics in Applied Physics, vol. 1, Dye Lasers, Springer-Verlag, 1973 (p. 1 of 80).
Moylan, C. R., et. al., Nonlinear Optical Chromophores with Large Hyperpolarizabilities . . . , 1993, J. Amer. Chem. Soc., 115, pp. 12599-12600.
Greenspan, P., et al., Nile Red: A Selective Fluorescent Stain . . . , 1985 J. Cell Biology, vol. 100, pp. 965-973.
Zhan, C., et al., Multi-photon absorption and optical limiting for six stilbazolium . . . , 2006, Optical Materials, 28, pp. 289-293.
Sage, D., et al., Automatic Tracking of Individual Fluorescence Particles: . . . , Image Processing, IEEE Transactions on 2005, vol. 14, No. 9, pp. 1372-1383.
Soundararajan, N., et al., Descriptive Photochemistry of Polyfluorinated Azide Derivatives of Methyl Benzoate, J. Org. Chem. 1990, 55, pp. 2034-2044.
Huisgen, R., et. al., Exceptional Reactivity of the Bicyclo[2.2.1]heptene Double Bond, J. Amer. Chem. Soc., 120, pp. 3951-3953, 1980.
Hassner, A, et al., Charge-Shift Probes of Membrane Potential. Synthesis, J. Org. Chem. 1984, vol. 49, pp. 2546-2551.
Dockter, M.E., Fluorescent Photochemical Surface Labeling . . . , J Biol. Chem., Apr. 1979, vol. 254, No. 7, pp. 2161-2164, www.jbc.org.

* cited by examiner

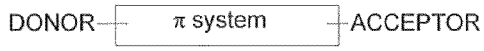

a) general D—π—A "push-pull" chromophore with unspecified donor, π system and acceptor

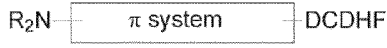

b) more specific D—π—A "push-pull" chromophore with an amine donor, π system and DCDHF acceptor

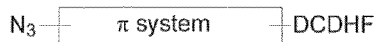

c) chromophore with little "push-pull" character due to the absence of a good donor (azide a poor donor)

d) Photochemical conversion of azide to amine (P-ATA).
Here the azide precursor "fluorogen" has shorter wavelength absorption and much less fluorescence than the amine product "fluorophore". This overall photochemical process converting azide to amine is called "P-ATA". Here R = some group derived from the reaction media, usually a hydrogen atom but R can also result from insertion of the nitrene into other covalent bonds such as C-H, C-C or O-H.

e) Thermochemical conversion of azide to amine (T-ATA).
Here the azide precursor "fluorogen" has shorter wavelength absorption and much less fluorescence than the amine product "fluorophore". This overall thermochemical process converting azide to amine is called "T-ATA". Here R = some group(s) in an intermediate (usually a dihydrotriazole) and/or preferably a final product (secondary amine, aziridine, etc) formed from loss of nitrogen from the dihydrotriazole.

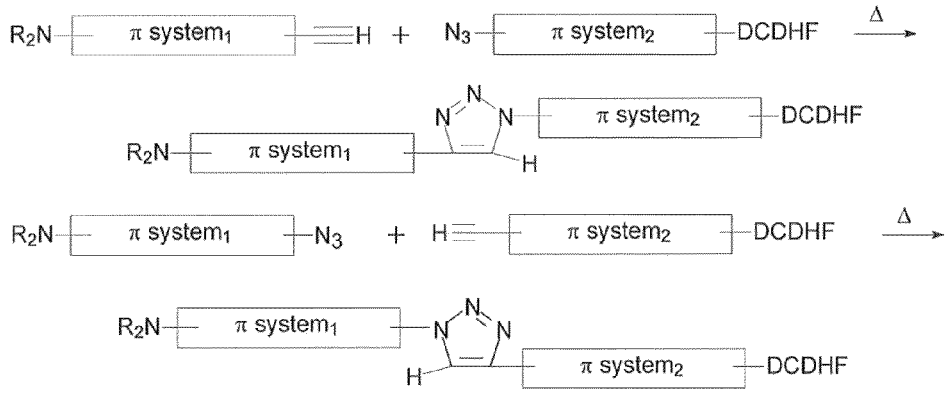

f) Thermochemical reaction of azide plus acetylene to 1,2,3-triazole (T-AAT). There are two versions:
  First, a pi-system with an amine and acetylene is reacted with a pi-system substituted by an azide and an acceptor group.
  Second, a pi-system with an amine and azide is reacted with a pi-system substituted by an acetylene and an acceptor group.
  These reactions are thermally activated but are also influenced by catalysis. A primary acetylene is shown here but fully substituted acetylenes, especially strained cyclic acetylenes, may also be used.
  Two isomers may be produced for each reaction, only one is shown. The spectroscopic properties are influenced by the relative distribution of the four functional groups and π systems on the triazole

FIG. 1

FLUOROGENIC COMPOUNDS CONVERTED TO FLUOROPHORES BY PHOTOCHEMICAL OR CHEMICAL MEANS AND THEIR USE IN BIOLOGICAL SYSTEMS

CROSS-REFERENCE

This is a division of application Ser. No. 12/454,273, filed May 13, 2009 for FLUOROGENIC COMPOUNDS CONVERTED TO FLUOROPHORES BY PHOTOCHEMICAL OR CHEMICAL MEANS AND THEIR USE IN BIOLOGICAL SYSTEMS, which claims the priority filing date of U.S. Provisional Application Ser. No. 61/128,729 filed May 23, 2008, herein fully incorporated by reference.

This invention was made with government support under Grant. No. 5P20-HG003638 awarded by the National Institutes of Health. The Government has certain rights in the invention

FIELD OF THE INVENTION

The present invention relates to non-fluorescent or poorly fluorescent precursor compounds, "fluorogens" that are converted to fluorescent product compounds by "various processes," One process may involve externally applied radiation including ultraviolet or visible light. The non-fluorescent precursor compounds and the fluorescent products produced can be labeled to various biological items using state-of-the-art tagging schemes. The fluorescent products serve to image the biological substance containing them, including cells and their components, compounds, systems and the like. The ability to actively control the fluorescence by photoactivation can be applied to super-resolution microscopy and other complex imaging schemes. Alternatively, fluorogens described herein can be converted to a fluorescent product by another process involving a chemical (nonphotochemical) reaction with a complementary functionalized substance. In the case of an appropriately functionalized biological system as a substrate, this overall process is tantamount to a turning on of fluorescence upon bioconjugation.

BACKGROUND OF THE INVENTION

Labeling biological structures in cells has long been an important and challenging area of research, and many commercial fluorophores are available for making biological structures visible. Current interest in biological and medical fluorescence imaging of cells has pushed to the single-molecule regime, wherein the light from just one molecule can be detected. This technique provides a window into, for example, the operation of the various nanomachines inside cells as they undergo mechanochemical and enzymatic reactions. Single-molecule imaging then provides the opportunity to understand how these individual machines work and/or to assess if there is any pathology present on a molecular level. A number of diseases depend upon small numbers of errant molecules, so the ability to detect cellular processes all the way down to single molecule is a key area for development.

In addition, there is much interest in photoswitchable molecules, so that the individual emitters can be turned on, one at a time or a few at a time, in order to image the position of each single molecule below the optical diffraction limit. The optical diffraction limit is approximately the optical wavelength employed divided by two, which would be, for example, about 250 nm for 500-nm optical wavelength. This effect typically limits the resolution of optical microscopy so that two objects closer together than the optical diffraction limit cannot be resolved by conventional optical microscopy. Recent advances in optical imaging beyond the diffraction limit with single molecules (Betzig, E. et al., Science, 2006, 313, pp. 1642-1645; Hess, S. T., et al., Biophys. J., 2006, 91, pp 4258-4272; and Rust, M., et al., Nature Meth., 2006, 3, pp. 793-795) have overcome this limitation of resolution, but at the same time have introduced a new requirement for fluorescent labels that can be turned on at will: fluorophores must be actively controlled (usually via photoswitching or photoactivation) to ensure that only one single emitter is switched on at a time in a diffraction-limited region (Werner, W. E., Proc. Nat. Acad. Sci. (USA), 2007, 104, pp. 12596-12602; Heileman, M. Laser & Photonics Reviews, 2009, 3, pp. 180-202; and Femandez-Suarez, M, Ting, A. Y., Nature Reviews Molecular Cell Biology, 2008, 9, pp 929-943). The location of each of these sparse molecules is precisely determined beyond the diffraction limit, and a super-resolution image is obtained from the summation of the positions of single molecules from successive rounds of photoactivation. The ultimate spatial resolution is determined by a number of factors, most importantly the total number of photons detected from each single molecule (Thompson, R. E., et al., Biophys. J., 2002, 82, pp 2775-2783) and the density of the fluorogenic labels. Super-resolution imaging by these methods often uses photoactivatable fluorescent proteins, which have the advantage of being genetically targeted (Ando, R, et al., Science, 2004, 306, pp. 1370-1373; and Patterson, G. H., et al., Science, 2002, 297, pp 1873-1877); however, fluorescent proteins typically provide 10-fold fewer photons before photobleaching than good small-molecule emitters (Harms, G. S., et al., Biophys. J. 2001, 80, pp. 2396-2408). Therefore, there is a need to develop new photoactivatable organic fluorophores as well as methods to target said probes to specific locations or biomolecules in living cells. Examples of state-of-the art chemistries, photophysics, and targeting schemes include the following: Chen, I., et al, Curr. Opin, Biotech., 2005, 16, pp. 35-40; Prescher, J. A., et al., Nat. Chem. Biol., 2005, 1, pp. 13-21; Adams, S. R., et al., J. Am. Chem., Soc., 2002, 124, pp. 6063-6076; Bates, M., et al., Phys. Rev. Lett., 2005, 94, pp. 108101-1-108101-4; Foiling, J., et al., Chem. Int. Ed., 2007, 46, 6266-6270; and Lord, S. J., et. al., 2008, J. Amer. Chem. Soc., 130, pp. 9204-9205.

Photoactivatable and chemically fluorogenic emitters have other important applications, including but not limited to photoaffinity labeling (PAL), spatial and temporal activation for diffusion studies, and mitigation of background fluorescence. For instance, one critical issue for the practical detection of fluorescence from single molecules in cells is the need to reduce the background emission signal that is due to the presence of extraneous and unwanted emitters. For example, some current cell-labeling schemes require incubation of a cell with a fluorophore, which may find a specific location in the cell by virtue of a special targeting moiety; however, those fluorescent molecules that are not correctly targeted must still be removed from the cell as their fluorescence may interfere with observation of the targeted fluorophore. This requires extensive washing of the cell to remove superfluous fluorescent tags. This washing step is also problematic in that it delays the observation of the molecules of interest until the washout is complete, hence dynamic phenomena are more difficult to observe. Worse, for the observation of single molecules, if the washout is not effective in removing all the superfluous fluorophores, the properly targeted single molecules are more difficult to distinguish and observe. It is desired to have bright organic fluorophores that can be turned on and/or of and the ability to optically generate fluorophores in a specific region of a cell would reduce washout problems.

Moreover, dark molecules that become fluorescent only after a bioconjugation chemical reaction also reduce the washing requirement.

Azide-based fluorogens have been reported previously, but they require short activation wavelengths, are not photostable enough to be applied to single-molecule imaging, react via a different mechanism, and do not produce fluorophores of the present invention (Dodder, M. E., *J Biol. Chem.*, 1979, 254, pp. 2161-2164, and Dreyfuss, G., et al., *Proceedings of the National Academy of Sciences*, 1978, 75, pp. 1199-1203). The Dreyfuss system brightens not by a chemical or photochemical reaction, but due to confinement of the heterocycle in the cyclic adenosine monophosphate. The Dockter system utilized a fluorogenic photoactivatable azide that was a naphthalene-based molecule 3-azido-(2,7)-naphthalene disulfonate instead of a push-pull, donor-pi-acceptor system as described herein. In the Dockter report, the fluorescence is quenched by the n→pi* transition of the azide, instead of by disruption of a push-pull system, as in the current invention. Evidence of the different type of photoactivation can be found in the reference Moreland, et al. *Anal. Biochem.* 1980, 103, 26-32, which demonstrates that the azido compound "ANDS" absorbs at wavelengths red-shifted compared to the resulting fluorophore 3-amino-(2,7)-naphthalene disulfonate, while for the current invention the azido fluorogens are blue-shifted relative to the generated fluorophore. While this mechanism of quenching by the azide electronic transition may be applied to the specific naphthalene case in the Dockter report, it does not describe the current invention. The current invention applies to push-pull chromophore systems, and the mechanism of switching involves a creation of the fully conjugated donor-pi-acceptor system in the fluorophore by installation of one or more of the critical components that is absent in the fluorogen. This different mechanism is manifested by a dramatic red-shift of the absorption found in the product amine fluorophores compared to the initial azide fluorogens (as in FIG. 2b): by changing the azide group to an amine and pumping at the longer absorption wavelength of the amine, the final fluorophore compound now possess all three of the necessary components of the push-pull system and lights up. A fluorogenic PAL based on an azido coumarin (SAED) has also been reported (B. Thevenin, et al., *Eur. J. Biochem.* 1992, 206, 471-7), but in this and all the earlier cases in the literature, the light required to excite fluorescence is in the near ultraviolet (e.g. 280 and 334 nm), which prohibits ultrasensitive detection in living cells, because these short wavelengths additionally pump cellular autofluorescence and cause cell damage. Photoconversion in these previous cases was not accompanied by a significant spectral shift, and the subsequent fluorophores were not photostable enough to be applied to single-molecule imaging. Therefore, the current invention represents a dramatic improvement over the prior art.

In summary, the prior art was not sufficient for many cell-imaging applications, because the photogenerated fluorophores were not sufficiently bright, long-lived, or possessed red enough absorption. The novel azide fluorogens based on push-pull chromophores described in the present invention are a major improvement over the prior art because in the new system the absorption and emission of the donor substituted fluorophore obtained from the original azide substituted fluorogen is red shifted from that of the original fluorogen hence allowing for single-molecule imaging in living cells. Furthermore, the photogeneration wavelengths producing this change are closer to the visible regime. Because push-pull chromophores can be tuned over a range of wavelengths including the longer wavelengths, it is possible to design fluorogenic photoactivatable azido-fluorogens that are better suited to experiments involving living cells. Such fluorogens when converted to fluorophores are bright and emit millions of photons before photobleaching, and so are powerful tools for a variety of experiments requiring ultrasensitive detection of individual fluorescent molecules.

SUMMARY OF THE INVENTION

The present invention relates to fluorogens that are converted to fluorophores either by photoactivation or by a chemical reaction. Fluorogens such as the azide-pi-acceptor type described here can typically be converted utilizing ultraviolet or blue light to an amine-pi-acceptor fluorophore or other donor-pi-acceptor fluorophore. Alternatively, the chemical reaction routes include the following: an azide-pi-acceptor fluorogen reacting with an alkene or a strained alkene to produce a dihydrotriazole- or amine-containing fluorophore; or an azide-pi-acceptor reacting with an alkyne to produce a triazole-pi-acceptor fluorophore; or an alkyne-pi-acceptor reacting with an azide to produce a triazole-pi-acceptor fluorophore. As utilized herein, a fluorogen is defined as a molecule that is a precursor to a fluorophore and which can be converted to the fluorophore by means of a photochemical or a chemical reaction. In addition, the fluorogen has less (meaning, generally, less intense and/or blue-shifted) fluorescence relative to the corresponding fluorophore or, at the least, the fluorescence of the fluorogen can be distinguished from that of the fluorophore. A fluorophore is generally defined herein as a molecule, or part of a molecule, which when excited, such as with incident radiation, emits fluorescent light. A chromophore is a molecule or part of a molecular entity consisting of an atom or group of atoms in which the electronic transition responsible for a given spectral band is approximately localized. Fluorogens and fluorophores are both types of chromophores and the donor-pi-acceptor are examples of groups of atoms from which fluorophores are constructed.

The fluorophore compounds and their fluorogen precursors of the present invention are generally specially functionalized types of chromophores. Useful specific classes of fluorophores include various fully conjugated donor-pi-acceptor molecules wherein the acceptor or pi-acceptors include dicyanomethylene dihydrofuran (DCDHF), 4-dicyanomethylene-2-methyl-6-p-dialkylaminostyryl-4H-pyran (DCM), nitrobenzoxadiazole (NBD), stilbazolium cations, and the like. Various classes of donors used in push-pull chromophores include amines and optionally oxygen or sulfur with various substituents (e.g. alkyl groups making them ethers or thioethers) or some heterocycles. In the case at hand the amine donor groups, which are derived from an azide, are of most interest. The pi system can be comprised of a single carbocyclic benzene ring, naphthalene ring, or heterocyclic aromatic system such as pyridine or thiophene and the conjugation may be further augmented with an additional alkene or acetylene linkage. Combinations of such units are often also employed, as well as other components set forth herein below.

The acceptor units often include nitro groups, cyano groups, or may be electron deficient heterocycles such as are found in barbituric acid or thiobarbituric acid derivatives. Some acceptors, here termed composite acceptors, combine multiple electron deficient units such as in dicyanovinyl, tricyanovinyl, and DCDHF, which are all comprised of multiple cyano groups built on an alkene or diene backbone. Various donor, pi, and acceptor groups are described in the literature and the same is hereby fully incorporated by reference. See, for example, Organic Nonlinear Optical Materials, Ch. Bosshard, et. al., CRC Press 2001; Ahlheim, Barzoukas et al., *Science* 1996, 271, pp 335-337; U.S. Pat. No. 6,750,603 to Huang and Chen; and U.S. Pat. No. 6,864,375 to Huang et al.; and U.S. Patent Application Publication 2005/0009109 A1, to Moerner and Twieg, all hereby fully incorporated by reference. Such combinations of donor, pi and acceptor units are often found in chromophores used for second-order nonlinear optics (NLO). Virtually all second order NLO molecules are "push-pull" chromophores wherein the lowest energy electronic transition involves a transfer of electron density between an electron donor group through a conjugated pi group to an electron acceptor group. See, for example, Milian, B., et al., *J. Phys. Chem. B* 2003, 107, pp 12175-12183 and references therein. This low energy electronic transition is absent or impeded when one or more of the required structure Components (donor, pi, acceptor) is absent. The invention thus encompasses a working system in which an azide is converted to a better donor by the action of light or by chemical reaction. Photochemical and/or chemical modifications of the other two critical components, pi and acceptor, will at least conceptually produce the same outcome.

The diagrams in FIG. 1 relate to generic fluorophores of the present invention and the same are discussed in greater detail herein below wherein the fluorophores are fully conjugated.

The present invention relates to bright organic fluorophores that can be imaged at the single-molecule level in living cells and are produced by photoactivation of a dark fluorogen precursor, which is based on a disrupted push-pull donor-pi-acceptor chromophore. A representative example is a fluorogen based on the DCDHF class of single-molecule cellular labels, in which an azide is connected to a dicyanomethylene dihydrofuran acceptor via a conjugated pi-bonded network. However, other dye classes in the push-pull donor-pi-acceptor family will also suffice, as set forth herein below. The azide functionalized fluorogen DCDHF fluorogen (e.g., compound 1 in FIG. 2*a*), is a molecule that is dark (nonfluorescent or low fluorescence) at the imaging wavelength until photoactivated with a short burst of low-intensity violet light (e.g. 407 nm). Photoactivation of the fluorogen leads to loss of molecular nitrogen and conversion of the azide moiety to a nitrene, a very highly reactive intermediate, which in turn is converted to an amine by reaction with its immediate environment, and ultimately resulting in the formation of a fluorophore (e.g., compound 2 in FIG. 2*a* which possesses all three critical donor-pi-acceptor components). The photochemical azide-to-amine conversion also shifts the electronic absorption to longer wavelengths, so that photoactivation of the resulting fluorophore creates a bright, red emitter that is photostable enough to be imaged on the single-molecule level in living cells. Proof-of-principle demonstrations described here indicate that photoactivation of azide-based donor-pi-acceptor fluorogens provides a new class of labels needed for super-resolution imaging schemes that require active control of the fluorescence of single molecules.

The light-activated fluorogen compounds of the present invention are molecules wherein an azide group and an acceptor group terminate the pi system (i.e. azide-pi-acceptor). This combination of substituents and pi system has relatively short wavelength absorption and low or no fluorescence (especially when subjected to or pumped with longer wavelengths) relative to the corresponding system wherein a better donor group, such as an amine donor along with the acceptor group terminate the same pi system (i.e. donor-pi-acceptor). The latter is obtained when the azide is photochemically converted to an amine ("P-ATA", for "Photochemical Azide To Amine").

These photoactive (e.g. by near ultraviolet or visible light) fluorogenic azides can be covalently bonded to substrates, including biological substrates, by a variety of established protocols employed for bioconjugation as are discussed in Hermanson, G. T., Bioconjugate Techniques, Second Edition, 2008, Academic Press. Examples by which the fluorogen may be bound to the substrate include reaction of a succinimide ester with an amine on the substrate to make an amide, the reaction of a maleimide with a thiol on the substrate to make a thioether, and more specialized reactive partners found in enzyme-based labeling such as the HaloTag or the SNAP-tag or the phosphoramidite system widely used in DNA synthesis and as described, respectively, in Los, C. V. et al., *Cell Notes*, 2005, 11, pp. 2-6, and Keppler, A, et al., *Nat Biotech*, 2003, 21, pp. 86-89.

Alternatively, photoactivation of the fluorogen may itself result in covalent attachment to a biological substance of interest, via photoaffinity labeling (PAL). For instance, in some cases, a photoactivated molecule may react through the nitrene or other intermediate and insert into bonds of nearby molecules other than the solvent, and thus attaching a fluorescent probe to biological material in the immediate environment of the fluorogen. This process could either be untargeted to label many regions of the cell, or be engineered to label a specific and targeted binding site for the fluorogen (e.g. a protein binding pocket, an RNA aptamer, etc.).

As already noted, the azide-to-amine process may also be obtained chemically, for example upon reaction of the azide-pi-acceptor with an alkene, particularly a strained alkene ("T-ATA", for "Thermal Azide To Amine"). The strained alkenes are particularly attractive as the release of strain energy in the cycloaddition increases the rate of cycloaddition and permits the cycloaddition to occur at a useful rate at temperatures compatible with biological samples. Ideally, and just as in the case of the photochemical process just described, at least part of the absorption band of the generated amine-pi-acceptor fluorophore should exist at a wavelength where the precursor azide-pi-acceptor has no (or at least little) absorption. This change in peak absorption wavelength will result in the opportunity for selective excitation of the amine-substituted material without excitation of any residual azide or alkene fluorogens that might result in further or spurious fluorescence. Generally, fluorogens described here may be converted to a fluorescent product upon a chemical reaction with a complementary functionalized substance. In the case of a functionalized biological system as substrate, this overall process is tantamount to a turning-on of fluorescence upon bioconjugation. These azide-pi-acceptor fluorogens are themselves not fluorescent or have fluorescence only when pumped at short wavelengths. However, the azide functional group in the fluorogen can undergo a bond forming cycloaddition reaction with a special partner to produce a fluorophore with a longer wavelength absorption and which is usually accompanied by an increased fluorescence wavelength and enhanced intensity. In the case of an azide-pi-acceptor reacting with an alkene or strained alkene, the initial cycloadduct product is a 4,5-dihydrotriazole derivative in which the dihydrotriazole can be a better donor than the azide group and this leads in some cases to a molecule with red-shifted absorption and enhanced fluorescence intensity relative to the original azide fluorogen. Especially interesting and valuable are certain cases where in the overall process this initially formed cycloadduct with a weak dihydrotriazole donor rearranges with loss of nitrogen to produce a product with a still better donor, such as a secondary amine or an aziridine. Both of these latter two systems (dihydrotriazole donor+acceptor and amine donor+acceptor) now have a more potent donor and constitute a red-shifted donor-pi-acceptor chromophore as compared to the initial azide-pi-acceptor chromophore. Furthermore, such rearrangements not only produce longer wavelength absorption but are also often accompanied by an increase of the extinction coefficient. Notably, the creation of the fluorophore accompanying the cycloaddition of the azide-terminated fluorogen with an alkene is novel.

The rates of the cycloaddition reaction between azide and alkene and the identity and rates of any subsequent rearrangements are a function of a variety of factors including but not limited to the specific identities of the individual reacting substances (both azide and alkene), their concentration, the solvent, the temperature and the pH. Typical relationships amongst structure and the rate and identity of products are described in the literature: P. Scheiner, et, al., 1965, *J. Amer. Chem. Soc.*, 87, pp. 306-311; A. C. Oehischlager, et. al., 1969, *Can. J. Chem.*, 47, pp. 4367-4374; M. E. Hermes, F. D. Marsh, 1972, *J. Org. Chem.*, 37, 2969-2979; R. Huisgen, et. al., 1980, *J. Amer. Chem. Soc.*, 102, pp. 3951-3953, K. J. Shea, J.-.S. Kim, 1992, *J. Amer. Chem. Soc.*, 114, pp. 4846-4855.

Another chemical fluorogenic approach is the reaction of an azide-pi-acceptor fluorogen with a reactive alkyne or a strained alkyne to produce a triazole fluorophore; or the reaction of an alkyne-pi-acceptor fluorogen with a reactive azide to produce a triazole fluorophore ("T-AAT", for "Thermal Azide Acetylene to Triazole"). As with strained alkenes, the release of strain energy in the cycloaddition increases the rate of cycloaddition and permits the cycloaddition to occur at a useful rate at temperatures compatible with biological samples. As with the T-ATA reaction described above, a change in peak absorption wavelength upon the chemical reaction results in the opportunity for selective excitation of the triazole-substituted material without excitation of any residual azide or alkyne fluorogens that might result in further or spurious fluorescence. Generally, fluorogens described here may be converted to a fluorescent product upon a chemical reaction with a complementary functionalized substance. In the case of a functionalized biological system as substrate, this overall process is tantamount to a turning-on of fluorescence upon bioconjugation. These azide-pi-acceptors (or alkyne-pi-acceptors) and functionalized alkynes (or azides) are themselves not fluorescent or have fluorescence only when pumped at short wavelengths. However, the azide and alkyne functional groups in the fluorogens can undergo a bond forming cycloaddition reaction (Huisgen type or [3+2] cycloaddition, see Brase, S., et. al., Cycloaddition Reactions of Azides Including Bioconjugation, 2008, *Topics in Heterocyclic Chemistry*, 12, 1861) with a special partner to produce a fluorophore with a longer wavelength absorption and which is usually accompanied by an increased fluorescence wavelength and enhanced intensity. That special partner may be an acetylene group, itself conjugated with a donor or acceptor, and the bond-forming reaction creates a 1,2,3-triazole ring. The bioconjugation of preformed fluorophores using a click type (azide+acetylene) reaction is known. The creation of the donor-pi-acceptor fluorophore accompanying the cycloaddition of the azide-terminated (or alkyne-terminated) fluorogen with an alkyne (or azide) is novel. The azide+acetylene cycloaddition may be promoted by catalysis (usually a copper salt) or thermally, especially when a strained or electronically activated alkyne is employed as described in Baskin, J. M. and Bertozzi, C. R. 2007, *QSAR Comb. Sci.*, 11-12, pp. 1211-1219. As a proof-of-principle example, we have demonstrated that after the click reaction of an azide fluorogen and an acetylene fluorogen (with a DCDHF acceptor terminating one end of the pi system and an alkyne terminating the other end, Formula 18), the fluorescence of the resulting triazole product (Formula 19) is enhanced.

In a minor variation to all the schemes described, instead of the absorption wavelength changing upon reaction, the wavelength of maximum fluorescence may dramatically change, thus making a two-color switchable fluorophore. Alternatively, the brightness of the emission may dramatically change. As long as the final product resulting from the chemical, photochemical, or bioconjugation reaction can be distinguished from the original educt(s), the azido version of a push-pull donor-pi-acceptor chromophore can act as a switch enabling turning-on of fluorescence.

BRIEF DESCRIPTION OF THE DRAWINGS

FIG. 1 describes schematically the structure of a typical push-pull chromophore and the various mechanisms by which a fluorogen may be converted to a fluorophore. These mechanisms are the photochemical azide to amine process (P-ATA), a thermal process in which an azide reacts with an alkene producing a dihydrotriazole or amine (T-ATA) and a second thermal process in which an azide reacts with an alkyne to produce a triazole (T-AAT). More specifically, FIG. 1 shows a-c) Features of push-pull chromophores, d) P-ATA Photochemical conversion of azide fluorogen to amine in a push-pull fluorophore. e) T-ATA Thermochemical conversion of an azide fluorogen to a fluorophore with a better donor, such as in a dihydrotriazole intermediate or better an amine in the final fluorophore. f) T-AAT Thermal fluorogen to fluorophore triazole conversion;

FIG. 2B Inset: Fluorescence from 594 nm pumping. After activation (solid line), there is at least a 100-fold increase from 1 (dotted line), which is practically nonemissive, (c) shows the photoactivation kinetics from data in (b). The total yield of the reaction ($[2]_f/[1]_i$) is 69%. Photoconversion data for 1 were fit using two exponentials ($[1]$=1.16 $e^{-1/7.40}$+1.50 $e^{-1/1291}$+0.545); data for 2 were fit using one exponential ($[2]$+2.32 $e^{-1/353}$2.32);

FIG. 3 shows three CHO cells incubated with fluorogen 1 (A) before and (B) after activation using a 10-s flash of diffuse, low-irradiance (0.4 W/cm$^2$) 407-nm light. (False color: red is the White-light transmission image and green shows the fluorescence images, excited at 594 nm.) Scalebar: 20 µm. (C) Fluorescence image of single molecules of activated 2 in a cell under higher magnification. Background was subtracted and the image was smoothed with a 1-pixel Gaussian. Scalebar: 800 nm;

FIG. 4 shows a CHO cell (500×) incubated with fluorogen 1 before (left), immediately after (middle), and 18.7 s after (right) a three-second activation with a tightly focused, moderate-irradiance (35 W/cm$^2$) 407-nm spot. The 594-nm light for imaging was illuminating the sample the entire time, except for the brief period of 407-nm activation. Only fluorophores in a small region of the cell are turned on, then they diffuse away and bleach. Height of the image is 16 µm. (False color: red is the white-light transmission image and green are the fluorescence images, excited at 594 nm.);

FIG. 5 shows (left) the spatial trajectory of a single copy of the DCDHF fluorophore diffusing in the membrane of a CHO cell after photoactivation. Dotted red lines indicate when the fluorophore was dark (i.e. blinking off). FIG. 5 (right) shows a background-subtracted intensity time-trace of the molecule in the trajectory on the left. Red lines indicate when the fluorophore was dark (i.e., initially blinking events, then finally bleaching);

FIG. 6 shows a concept for formation of a fluorophore inside a cell involving a [3+2] cycloaddition reaction between an azide and an alkene (T-ATA). This diagram depicts a method of using an azide-containing fluorogen and a strained alkene (norbornene) that has been functionalized to bind at a specific site inside a cell. The fluorogen can be a precursor for a push-pull dye [donor-pi system-acceptor] wherein one of the components is absent or nonconjugated. In the examples here the fluorogen will have the structure [azide-pi system-acceptor]. (A) Strained alkene functionalized with biological binding motif is introduced into the cell. (B) After the motif binds with a receptor site in the cell the azide-fluorogen (N$_3$-Fl) is introduced into cell. (C) The azide of the fluorogen reacts with the strained alkene yielding a covalent linkage involving a nitrogen atom (dihydrotriazole, amine, aziridine) which is also involved as the donor in the [Donor-pi system-Acceptor] system. The binding event is also responsible for creation of the fluorophore structure, permitting fluorescence to be generated upon excitation; FIG. 7 (right) shows gel electrophoresis of CHO-cell lysate demonstrating fluorogenic photoaffinity labeling (PAL) using NBD-azide. (Similar results were seen for DCDHF-P-azide PAL.) The left panel shows the stained protein, imaged with white light; the right panel is fluorescence from NBD photochemically cross-linked to proteins, imaged using 488 nm. The left lane in the gel (+PAL) is protein covalently labeled with NBD by PAL. The right lane (−PAL) is a control performed by mixing into the cell solution preactivated NBD, which is fluorescent but cannot participate in the covalent PAL bioconjugating reaction. The fluorescence signal in the control lane was significantly lower. The blurry fluorescence on the bottom of the gel is from the unbound dye at the front edge; equal brightness in both lanes indicates equal dye concentration in the PAL and control;

DETAILED DESCRIPTION OF THE INVENTION

Figure 2A:
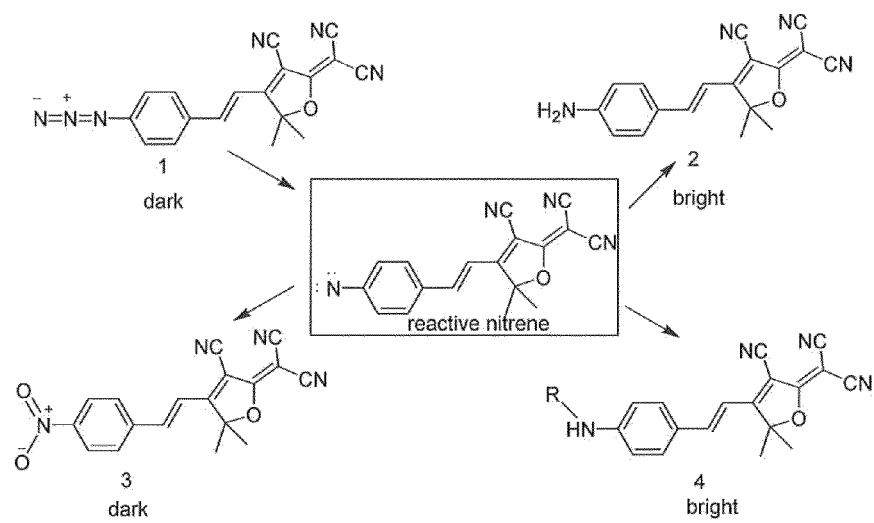
FIG. 2*a* relates to a specific example of a P-ATA reaction scheme of a DCDHF azide fluorogen and the conversion thereof via a reactive nitrene to either amine terminated fluorescent fluorophores or a non-amine non-fluorescent compound as described in Lord, S. J., et. al., 2008, *J. Amer. Chem., Soc.*, 130, pp. 9204-9205.

The fluorogens are the basic building blocks of the present invention and they are converted to compounds that are fluorescent generally by three different routes: P-ATA, T-ATA, and T-AAT. First, a photoactivation process with visible or near-ultraviolet radiation in which an azide fluorogen is converted to an amine fluorophore (photochemical azide to amine, P-ATA). Second, a chemical and/or a thermal process (thermochemical azide to amine, T-ATA) in which an azide fluorogen reacts with an alkene or strained alkene producing, initially, a dihydrotriazole which itself may rearrange to an amine substituted fluorophore by loss of nitrogen. Third, and finally, a chemical and/or thermal process in which an azide reacts with an acetylene to produce a 1,2,3-triazole, (thermochemical azide plus acetylene to triazole, T-AAT). This third process is distinct from the second because a triazole is produced instead of a dihydrotriazole, and unlike the dihydrotriazole the triazole will not lose nitrogen and rearrange to an amine. A general scheme of conversion of a fluorogen to visible fluorophores of the present invention is shown in FIG. 1. In FIG. 1*a*, a general formula is shown with regard to the donor-pi-acceptor fully conjugated fluorophores of the present invention. FIG. 1*b* relates to a specific fluorophore wherein the donor is usually an amine compound and the acceptor is DCDHF as set forth herein below. In FIG. 1*c*, a specific fluorogen is disclosed wherein the donor (as in 1*b*) is replaced by an azide, which is not a donor. FIG. 1*d* shows a typical RATA reaction of an azide fluorogen that upon photoactivation is converted to a fluorophore with an amine donor replacing the azide group. FIG. 1*e* shows a typical thermally induced reaction of an azide fluorogen to a fluorophore now with a nitrogen donor (T-ATA). This latter thermal reaction may involve initial production of a dihydrotriazole, itself a potential fluorophore, but also additional rearrangement products, such as an amine (including aziridines) which are also fluorophores. FIG. 1*f* shows a thermal reaction between an azide and an acetylene, both of which are fluorogens, producing a triazole (T-AAT), which may possess better fluorophore properties than the individual fluorogen precursors. The rate of this reaction and the resulting change in properties here will depend on the exact structures of the reacting azide and acetylene pair, including the identity, number and location of substituents they bear as well as the structure of the resulting triazole. This rate and product composition of this reaction may be influenced by catalysis and use of a strained or otherwise activated acetylene.

Azide Compounds

An azide is the $N_3$ functional group or a compound, such as R—$N_3$, containing this functional group. An azide compound may be ionic or covalent. In the case of most organic compounds the bond to the azide functional group is largely covalent. In an organic azide compound R can be a wide range of structures, but the R structures of relevance here have the azide attached to an sp$_2$ carbon atom and, in particular, an sp$_2$ hybridized carbon atom which is part of an aromatic ring. That is, while the R group can be an aliphatic such as an alkyl having from 1 to about 10 carbon atoms, desirably it is an aromatic group containing one or more rings such as benzene, naphthalene, and the like. While not preferred, the aromatic group can contain one or more substituents thereon such as an aliphatic group, for an example an alkyl group containing from 1 to 12 carbon atoms, and the like. The R group can also be a heterocyclic containing a total of from about 3 to about 12 atoms with one or more of the atoms being O, S, N, or a halide. Examples of heterocyclics include pyridine and derivatives thereof.

Acceptors

An acceptor (represented in chemical structures by "A" or "$A_n$," where n is an integer number of acceptor groups, typically from 1 to 5 units) is an atom or group of atoms that has a low reduction potential, wherein the atom or group of atoms can accept electrons from a donor through an Abridge. The acceptor (A) has a higher electron affinity than does the donor (D), so that the chromophore is generally polarized, with relatively more electron density on the acceptor (A). Typically, an acceptor group contains at least one electronegative heteroatom that is part of a pi bond (a double or triple bond) such that a resonance structure can be drawn that moves the electron pair of the pi bond to the heteroatom and concomitantly decreases the multiplicity of the pi bond (i.e., a double bond is formally converted to single bond or a triple bond is formally converted to a double bond) so that the heteroatom gains formal negative charge. The heteroatom may be part of a heterocyclic ring. Exemplary acceptor groups include but are not limited to —$NO_2$, —CN, —CHO, —COR, —$CO_2$R, —PO(OR)$_3$, —SOR, —$SO_2$R, —$SO_3$R. The total number of heteroatoms and carbons in a acceptor group is about 5 to about 15, and the acceptor group can be substituted further with alkyl (as defined herein), aryl (as defined herein), and heteroaryl (as defined herein). The "donor" and "acceptor" terminology is well known and understood in the art of the present invention. See, e.g., U.S. Pat. Nos. 5,670,091, 5,679, 763, and 6,090,332.

Figure 2B:
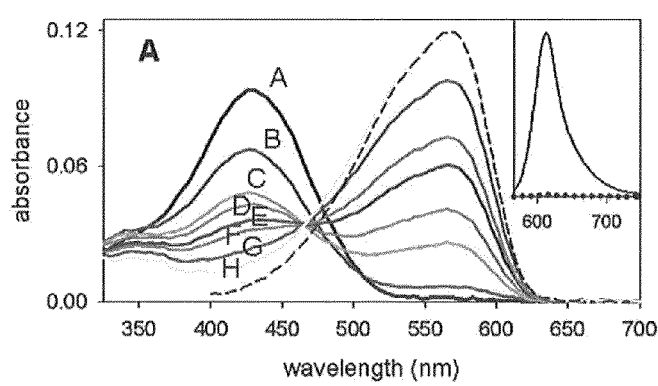
FIG. 2*b* relates to various time dependent absorption curves showing the conversion of a DCDHF azide fluorogen to a fluorescent amino DCDHF fluorophore, FIG. 2*c* relates to the total yield of the conversion of the same fluorogen and fluorophore pair. More specifically, Figure(a) shows the conversion of fluorogen (1) to a fluorophore (2) via a photochemically generated reactive nitrene. Nitro compound (3) is a minor byproduct and (4) is a hypothetical product resulting from reaction of the nitrene with some molecule in the environment (R could be a biomolecule and then then this is an example of photoaffinity labeling). Azide compound 1 and Nitro compound 3 are dark (low fluorescence) while amines 2 and 4 are bright (high fluorescence). (b) shows the absorption curves in ethanol (bubbled with $N_2$) showing photoactivation of 1 ($\lambda_{abs}$=424 nm) over time to fluorescent product 2 ($\lambda_{abs}$=570 nm). Different colored curves represent 0, 10, 90, 150, 240, 300, 480, and 1320 seconds of illumination by 3.1 mW/cm$^2$ of diffuse 407-nm light. The sliding isosbestic point may indicate a build-up of reaction intermediates. Dashed line: absorbance of pure, synthesized 2.

The fluorogens and the fluorophores of the present invention contain various types of acceptors including those known to the art and to the literature. The acceptors are often small functional groups, especially electron accepting groups comprising nitro, nitroso, cyano, ketone, sulfone, ester, carboxylic acid, amide, or sulfonic acid, or any combination thereof. Often one or more of these electron accepting groups is bonded to one or more alkenes or to one or more aromatic rings, or bonded to at least one other electron accepting group through one or more alkenes or through one or more aromatic rings, or one or more heterocyclic aromatic rings containing one or more nitrogen, and/or one or more oxygen atoms; or any combination thereof. For example, two more aromatic rings can be combined containing at least one electron accepting group, or one or more aromatic rings containing an electron accepting group can be combined with one or more alkene groups of two or more alkene compounds containing an electron accepting group can be combined. The DCDHF acceptor group is a good example of a composite acceptor; it is comprised of three individual cyano groups which themselves are bound to a conjugated diene. For example, see U.S. Pat. Nos. 7,507,840 and 6,716,995, hereby fully incorporated by reference. In U.S. Pat. No. 6,716,995, FIGS. 1A and 1B illustrate exemplary donor moieties (D) that may incorporated into a chromophore where, in FIG. 1A independently at each occurrence, R is alkyl, aryl, or heteroaryl, X is O, S, Se, or Te, and n is 1 or 2; and in FIG. 1B independently at each occurrence, R is alkyl, aryl or heteroalkyl; $R_1$ is hydrogen, alkyl, aryl or heteroalkyl; Y is O, S or Se; m is 2, 3 or 4; p is 0, 1 or 2; and q is 0 or 1; wherein each of alkyl, aryl and heteroaryl is defined herein. FIGS. 2A and 2B illustrate acceptor moieties (A) that may be incorporated into a chromophore where, in FIG. 2A independently at each occurrence, R is alkyl, aryl, and heteroaryl, X is O, S, Se, or Te, and is 1 or 2; and FIG. 2B independently at each occurrence, R is alkyl, aryl or heteroalkyl; $R_1$ is hydrogen, alkyl, aryl or heteroalkyl; Y is O, S or Se; and q is 0 or 1; wherein each of alkyl, aryl and heteroaryl is defined herein. FIGS. 3A and 3B illustrates pi-bridges that may be incorporated into a chromophore where, in FIG. 3A independently at each occurrence, $Z^1$ is O, S, Se, $NR^1$, $C(R^1_2)$ or —$C(R^1)$=$C(R^1)$—; p is 0, 1 or 2; o is 0, 1 or 2; 0-1-p is at least 1; $R^1$ is hydrogen, alkyl, aryl or heteroalkyl. Examples of such specific acceptors are also set forth in U.S. Pat. Nos. 6,750,603, 6,864,375, and U.S. Patent Application Publication 2005/0009109 A1, hereby fully incorporated by reference.

A desired acceptor of the present invention is DCDHF, a heterocyclic acceptor as set forth in Formula 3. This acceptor is currently examined in fluorescent dyes, Lord, S. J., et. al., *Chem Phys Chem*, 10, 2009, pp. 55-65; also used in photorefractive materials, Ostrovherkova, O., et al., 2003 *Chem Phys Chem*, 7, pp. 732-744 and also used in electro-optic materials (where it is sometimes referred to as TCF) Andreu, R., et. al., *Org. Lett.*, 2008, 10, pp 49634966 and Zhang, C., et. al., *Chem. Mater*, 2001, 13, pp. 3043-3050. The DCDHF (or TCF) is an example of a composite acceptor built from multiple individual acceptors (three cyano groups) with internal π-linkage (two conjugated alkenes, one endocyclic and one exocyclic). This unit, 3-cyano-2-dicyanomethylene-5,5-dimethyl-2,5-dihydrofuran, is used as an acceptor with attachment to the rest of the chromophore (or fluorogen or fluorophore) at the 4 position:

The $R_1$ and $R_2$ groups of Formula 3 as well as other $R_1$ and $R_2$ groups set forth in the various acceptor formulas 1 through 8 as set forth herein below as well as in the claims independently, comprise H; or, an alkyl group having from 1 to about 18 carbons; or an aryl group having from 4 to about 14 carbon atoms; an aromatic heterocyclic group containing one, or more or combination of oxygen, nitrogen, sulfur, atoms and 4 to about 14 carbon atoms; or an alkene or an alkyne group each, independently, containing from 2 to about 18 carbon atoms; or wherein said alkyl, alkene, alkyne, aryl group, or said aromatic heterocyclic group, each, independently and optionally, contain a functional group comprising an ether, an amine, a cyano, an alcohol, a carboxylic acid, or a sulfonic acid, or any combination thereof. The various alkyl, alkene, or alkyne groups, independently, can be linear or branched or components of cyclic structures. Examples of the above-noted $R_1$ and $R_2$ groups, independently include methyl, ethyl, propyl, isopropyl, isobutyl, 2-ethylhexyl, pyrrolidine, piperidine, homopiperidine, 2-methylpiperidine, methylalcohol, dimethylether, propionic acid, cyanomethyl, butyl alcohol, phenyl, biphenyl, naphthyl and the like.

The DCDHF acceptor is a very strong conjugated acceptor group that characterizes the DCDHF chromophores (fluorophores) of which they are an important structural component. Other suitable acceptors of the present invention are set forth herein below within Formulas 1-8. The site of attachment of the acceptor group to the rest of the molecule, usually at a pi site, is indicated here by the squiggle in these Formulae.

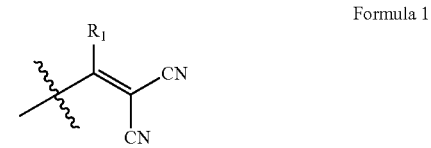

dicyanovinyl (when $R_1$ = H), or

Formula 1

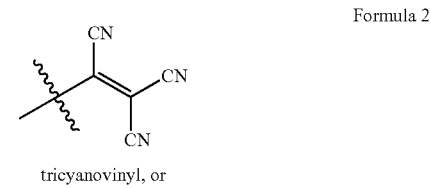

tricyanovinyl, or

Formula 2

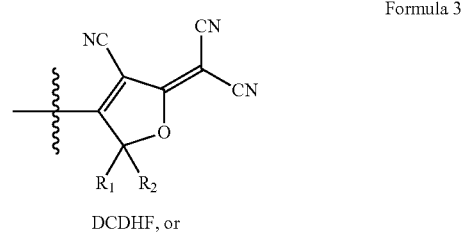

DCDHF, or

Formula 3

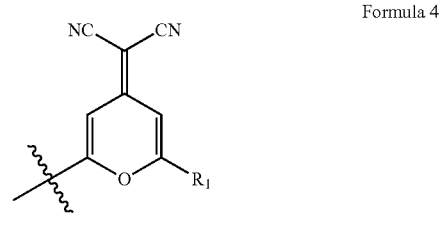

DCM, or

Formula 4

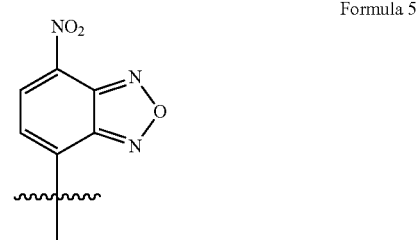

NBD, or

Formula 5

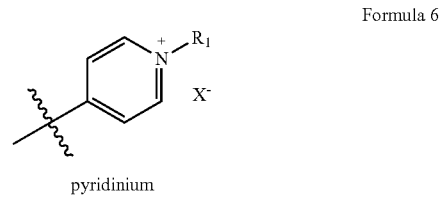

pyridinium

Formula 6 wherein $R_1$ is not H and x is a counterion

An example of a more highly functionalized acceptor, is

Formula 7

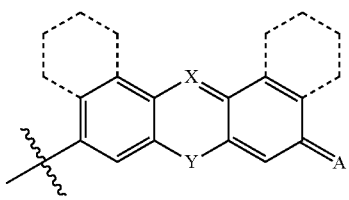

X = CR₁, N
Y = NR₂, O, S, or CR₃R₃
A = O, or N⁺R₅R₆

$R_3$, $R_4$, $R_5$, and $R_6$ can each be the same, independently, as $R_1$ or $R_2$ except that $R_5$ and $R_6$ can be combined to make a cycloaliphatic group.

For example, when X=N, Y, A=O and right dashed ring is benzene then this is a Nile Red type system. A precursor to the azide for the Nile red system might be made from the appropriate amine found in Nakanishi, J., et. al., 2001, *Anal. Chem.*, 73, pp. 2920-2928.

Formula 8

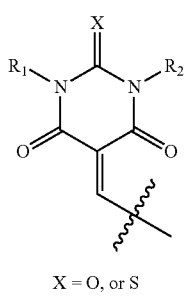

X = O, or S barbituric or thiobarbituric acid derivative with methylene link shown
or any combination thereof, and
wherein said $R_1$ and said $R_2$, independently, are set forth above.

A suitable acceptor is the dicyanovinyl group (with $R_1$=H) (Formula 1) which is found in many NLO chromophores functioning as an electron accepting group such as described in Meier, H., et. al., 2007, *Eur. J. Org. Chem., pp.* 625-631. This is a small composite acceptor built from an alkene and two cyano groups. A modification involving substitution by $R_1$ is possible, where $R_1$ is chosen from $R_1$ already discussed here.

A suitable acceptor is the tricyanovinyl group (Formula 2) which is found in many NLO chromophores functioning as an electron accepting group as described in Zhao, C. Y., et. al., 1996, *Theochem-Journal Mol. Struct.*, 367, pp. 73-82. This is a small but potent composite acceptor built from an alkene and three cyano groups.

Another suitable acceptor of the present invention is a dicyanomethylene dihydropyran (DCM) and has a formula as set forth in Formula 4. This type of acceptor is found in laser dyes, Meyer, M. and Mialoco, J. C., 1987, *Opt. Comm.*, 64, pp 264-268; and also some electro-optic chromophores Moylan, C. R., et. al., 1996, *J. Amer. Chem., Soc.*, 118, pp 12950-12955. This a composite acceptor constructed from two cyano groups and three cross-conjugated alkenes, two endocyclic and one exocyclic.

Another representative acceptor is nitrobenzoxadiazole (NBD) which is a composite acceptor having the formula set forth in Formula 5. The nitro group is the external acceptor while the electron deficient benzoxadiazole ring has a dual function of pi system and secondary acceptor unit. This NBD structure is found in fluorescent dyes which find wide use in biological labeling, Onoda, M., 2002, *Luminescence,* 17, pp. 11-14. Replacement of the nitro group with a sulfonamide gives the related DBD series of fluorophores.

Another suitable pi-acceptor is the pyridinium group, which has the general structure set forth in Formula 6. Such alkylated heterocycles are found in nonlinear optical chromophores such as the stilbazolium chromophores, Marder, S. R., 1992, *J. Mater. Chem.*, 2, pp 985-986. Many variants on the alkylated pyridine acceptor using other alkylated heterocycles are found in cyanine dyes, Hamer, F. M., "The cyanine dyes and related compounds", Wiley Interscience, 1964.

Formula 7 relates to a system in which the acceptor and pi system are heavily integrated and difficult to cleanly separate. Compounds of Formula 7 are derivatives of important dye classes. For example, Rhodamine 110 (X=C—C₆H₄COOH, Y=O, A=NH₂+), Oxazine 118 (X=N, Y=O, A=NH₂+), resorufin (X=N, Y=O, A=NH₂+) and numerous others. See, for example, Schafer, F. P., *Topics in Applied Physics, Vol 1, Dye Lasers*, Springer-Verlag (1973).

Formula 8 relates to derivatives of barbituric (X=O) and thiobarbituric, (X=S) acids used as acceptor groups, again which have found use in electro-optic applications, Moylan, C. R., et. al., 1993, *J. Amer. Chem. Soc.*, 116, pp. 12599-12600. These acceptor groups derived from barbituric acid are shown here including a methylene link in between the rest of the pi system.

Pi Groups

A "pi-bridge" or "electronically conjugated bridge" (represented in chemical structures by "pi" or "pi," where n is an integer typically from 1 to 5 units) is comprised of an atom or group of atoms through which electrons can be delocalized from an electron donor (defined below) to an electron acceptor (defined below) through the orbitals of atoms in the bridge. Such groups are very well known in the art. Typically, the orbitals will be p-orbitals on double (sp²) or triple (sp) bonded carbon atoms such as those found in alkenes, alkynes, neutral or charged aromatic rings, and neutral or charged heteroaromatic ring systems. Additionally, the orbitals can be p-orbitals on atoms such as boron or nitrogen. Additionally, the orbitals may be p, d or f organometallic orbitals or hybrid organometallic orbitals. The atoms of the bridge that contain the orbitals through which the electrons are delocalized are referred to here as the "critical atoms." The number of critical atoms in a bridge can be a number from 1 to about 30, The critical atoms may be substituted with any organic or inorganic group. The substituent may be selected with a view to improving the solubility of the chromophore in a polymer matrix, to enhancing the stability of the chromophore, or to any other purpose.

Generally, the pi system can be defined as being conjugated and from one or more contiguous alkenes each, independently, containing from 2 to about 12 carbon atoms, or wherein said one or more alkenes is replaced by a —(CH=N)— unit, or wherein said one or more alkenes are substituted with an aliphatic group containing from 1 to about 18 carbon atoms; or is derived from one or more alkynes each, independently, containing from 2 to about 12 carbon atoms; or is derived from one or more aromatic or heterocyclic aromatic groups or mono or polysubstituted aromatic or heterocyclic groups wherein each, independently, aromatic group has from 3 to about 26 total ring atoms, or each, independently, heterocyclic aromatic group has from 3 to 26 total ring atoms and from 1 to 3 nitrogen, oxygen, sulfur, phosphorus, or selenium atoms, and wherein each substituent, independently, is a) one or more alkyl groups having a total of from 1 to about 18 carbon atoms, or b) is one or more alkene groups having a total of from 2 to about 4 carbon atoms, or c) one or more alkyne groups having a total of from 2 to 10 carbon atoms; or d) is an unsubstituted heterocyclic alkene or alkyne group having a total of from 3 to about 10 carbon atoms, or e) wherein said substituent is one or more halides; or f) wherein said substituent can be connected to 2 or more of said aromatic groups. Desirably, many useful pi compounds are a combination of aromatic and heterocyclic compounds with one or more alkenes, alkynes, and the like. Thus, the one or more aromatic or heterocyclic aromatic or mono or polysubstituted aromatic or heterocyclic groups, each, independently, can contain from 5 to about 14 ring atoms, the one or more substituted alkyl groups, each, independently, can contain from 1 to about 8 carbon atoms, and desirably the heterocyclic aromatic group ring optionally contains one or more of only nitrogen, oxygen, or sulfur atoms therein.

More specifically, pi ($\pi$) is a conjugated system comprised of a variety of unsaturated groups in various combinations: e.g. linear combinations of aromatic rings ($Ar_1$—$Ar_n$-) wherein n is 1 to about 6; or combinations of an aromatic ring with alkenes ($Ar_1$—$(CH=CH)_m$) where m is 1 to about 6; or combinations of aromatic rings with alkenes ($Ar_1$—$(CH=CH)_m Ar_n$) where m is 1 to about 6, and n is 1 to about 6; or combinations of an aromatic ring with alkynes ($Ar_1$—$(C\equiv C)_m$) where m is 1 to about 3; or combinations of aromatic rings with alkynes where m is 1 to about 6; and n is 1 to about 6. In cases where there are multiple attachments to an aromatic ring containing six atoms they are most effectively made by attachment at pare positions (rather than ortho or meta positions, if available). Alternatively, the above aromatic rings can be heterocyclic rings containing from 3 to about 6 atoms. In the case of 5 member cyclic or heterocyclic ring systems the attachments are likewise most effective if they are for atoms apart and those atoms are carbon atoms (as in a 2,5-disubstituted thiophene or a 2,5-disubstituted 1,3,4-oxadiazole).

In addition to the alkene pi unit —(CH=CH)— an analogous nitrogen containing unit —(CH=N)— known as an azomethine or Schiff base is sometimes useful. In addition to the simple alkenes —(CH=CH)— already shown, more substituted versions with other groups replacing the hydrogens can be employed —($CR^x=CR^y$)— here $R^x$ and/or $R^y$ can be aliphatic and contain from 1 to about 18 carbon atoms, and/or aromatic and contain from 4 to abut 24 carbon atoms, and can comprise part of a ring. Another related pi unit is the azo group —(N=N)—. While commonly employed in NLO materials, usually as a subunit of azobenzene, Ph-N=N-Ph, it is of lesser use in fluorescent dyes due to lowered fluorescence quantum yields.

As apparent from the above, pi systems can take a wide range of forms but often contain at least one aromatic ring ($Ar_1$) and the donor such as an amine (and its precursor azide group) is usually attached directly to the initial aromatic ring ($Ar_1$). The aromatic rings are usually benzene but can also be condensed benzene compounds (naphthalene, anthracene, phenanthrene, pyrene, etc).

In addition to carbocyclic ring(s) the pi-system can also be comprised of six member ring heterocycles such as pyridine or five membered ring heterocycles such as thiophene. The ring(s) can also be one or more heterocyclic aromatic rings fused with carbocyclic rings such as benzene and examples include indole, benzofuran, benzothiophene, benzimidazole, benzoxazole, benzothiazole, carbazole, dibenzofuran, dibenzothiophene (and others which contain one or more fused five member rings) as well as quinoline, isoquinoline, quinoxaline and others with one or more fused six member rings. The heterocycles may also include units derived from the fusion of two or more heterocycles such as 1,8-naphthyridine, thieno [3,2-b]thiophene and dithieno[3,2-b:2',3'-d]thiaphene.

Donor Group

A donor (represented in chemical structures by "D" or "$D_n$" where n is an integer typically from 1 to 5 units) is an atom or group of atoms that has a low oxidation potential, wherein the atom or group of atoms can donate electrons to an acceptor "A" through pi-bridge. The donor (D) has a lower electron affinity that does the acceptor (A), so that the chromophore is generally polarized, with relatively less electron density on the donor (D). Typically, a donor group contains at least one heteroatom that has a lone pair of electrons capable of being in conjugation with the p-orbitals of an atom directly attached to the heteroatom such that a resonance structure can be drawn that moves the lone pair of electrons into a bond with the p-orbital of the atom directly attached to the heteroatom to formally increase the multiplicity of the bond between the heteroatom and the atom directly attached to the heteroatom (i.e., a single bond is formally converted to double bond, or a double bond is formally converted to a triple bond) so that the heteroatom gains formal positive charge. The p-orbitals of the atom directly attached to the heteroatom may be vacant or part of a multiple bond to another atom other than the heteroatom. The heteroatom may be a substituent of an atom that has pi bonds or may be in a heterocyclic ring. Exemplary donor groups include but are not limited to $R_2N$—, see FIG. 1A, and RX— where R is alkyl (as defined herein), aryl (as defined herein), and heteroaryl (as defined herein), X is O, S, Se, or Te, and n is 1 or 2. The total number of heteroatoms and carbons in a donor group is from about 3 to about 30, and the donor group can be substituted further with alkyl (as defined herein), aryl (as defined herein), and heteroaryl (as defined herein). The "donor" and "acceptor" terminology is well known and understood in the art of the present invention. See, e.g., U.S. Pat. Nos. 5,670,091, 5,679,763, and 6,090,332, hereby fully incorporated by reference.

In the fluorogen compounds described here an effective donor is usually absent, being replaced with a poor donor azide or alkyne). The fluorogens containing an azide (or alkyne) group undergo a transformation in which a superior donor is created and the spectroscopic properties of the product are modified in a useful way. The azide (or alkyne) group is bonded to the various pi systems of the present invention, which are set forth hereinabove. Briefly, when an azide fluorogen is photoactivated, a fluorophore is produced which retains the pi group and acceptor as found in the original azide compound but instead with an amine (or other nitrogen) donor instead of the original azide. When a chemical (non-photochemical) reaction route is utilized with the fluorogens of the present invention, the azide (or alkyne) compound is reactive with other partner compounds set forth hereinbelow in greater detail. The reactive partner of the azide may be an alkene or a strained alkene to produce a dihydrotriazole which itself may rearrange to an amine, or the reactive partner may be an alkyne or a strained alkyne compound and in this case a product containing a triazole ring is formed. The fluorogens containing an alkyne group can react with another compound containing an azide, forming a triazole.

Pi-Acceptor Group Combinations

As should be apparent from the above, numerous pi-acceptor group combinations can be formed by joining one or more of the above noted pi groups and one or more of the acceptor groups. As is also noted above, the fluorogens of the present invention are generally made by adding an azide group (or alkyne group) to any of these pi-acceptor group combination compounds of the present invention. Some of the more desired pi-acceptor groups are set forth in Formulas 10 through 19 as follows, wherein a squiggle line indicates attachment to the rest of the molecule.

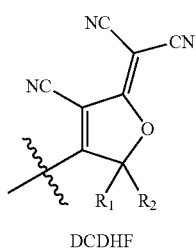

Formula 10

DCDHF

In Formula 10 is found the DCDHF acceptor-pi group, which is a good example of a composite acceptor wherein small individual acceptor groups (three cyano groups) are tightly integrated with a pi system (e.g. a diene) to create an overall larger acceptor group. This DCDHF acceptor group is then attached to additional pi system which itself is usually terminated by an azide in the fluorogen form.

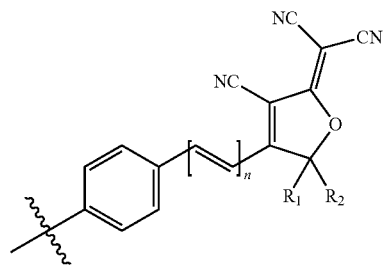

Formula 11 phenyl-vinyl DCDHF
(when n = 1)

Formula 11 is an example of the DCDHF group attached to one or more alkenes and then to a benzene ring as part of that additional pi system which would be terminated by an azide in the fluorogen.

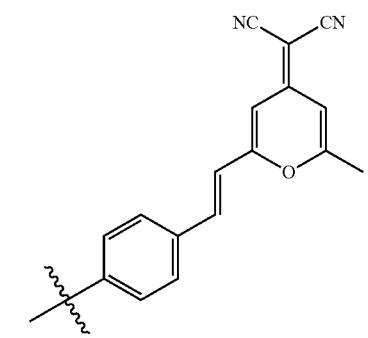

Formula 12 phenyl-vinyl-DCM

Formula 12 is an example of the DCM heterocycle acceptor group extended with an additional vinyl and phenyl group on one side. Sometimes extensions are used on both sides of this acceptor. The entire heterocycle-vinyl-phenyl unit is sometimes referred to as "DCM".

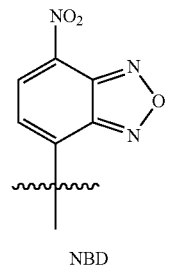

Formula 13

NBD

The NBD group illustrated in Formula 13 is already a composite acceptor, here the $NO_2$ is clearly an acceptor group but the benzoxadiazole ring system serves a dual role as pi system but also in some cases as an acceptor and pi system fused into "NBD".

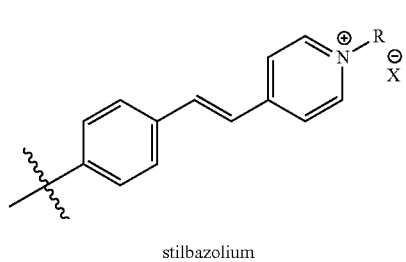

Formula 14 stilbazolium

The stilbazolium system in Formula 14 is the combination of the N-alkylpyridinium acceptor with the phenylvinyl pi-system. The entire structure is called stilbazolium due to its resemblance to stilbene.

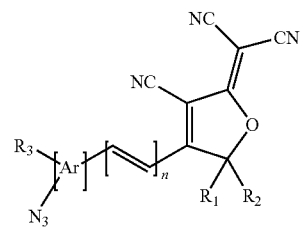

Formula 15

Formula 15 is an example of a full-fledged azido DCDHF fluorogen with an aryl-vinyl pi-system where Ar may be any of the pi conjugated groups.

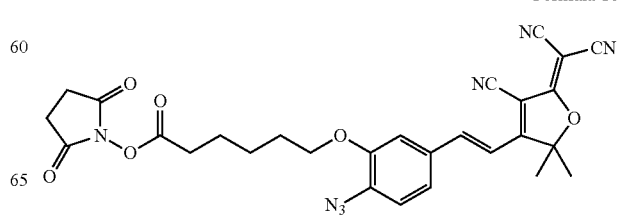

Formula 16

Formula 16 is an example of a full-fledged azido DCDHF fluorogen with a vinyl phenyl pi group and a N-hydroxy succinimide side group installed as a side group on the pi system to allow for bioconjugation to amine moieties as is well-known in the art.

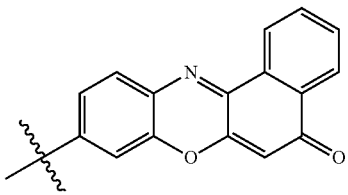

Formula 17

Formula 17 is the highly integrated acceptor and pi system of the Nile red type chromophore (a Et$_2$N donor group would be attached in Nile Red itself). If an azide is attached instead of the amine then this is a fluorogen for a Nile Red type fluorophore; Greenspan, P., 1985 *J. Cell Biology*, 100, pp. 965-973.

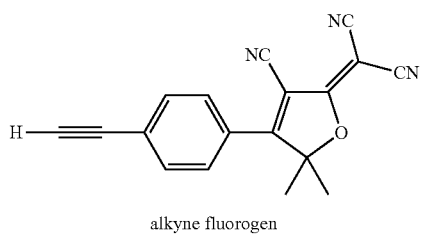

Formula 18 alkyne fluorogen

Formula 18 is an example of a full-fledged alkyne-pi-acceptor fluorogen for T-AAT reactions, in this case the structure is a ethynylphenyl substituted DCDHF. The ethnyl group is not a donor, but when reacted with an appropriately functionalized azide a somewhat more conjugated (but not fully conjugated) adduct is produced containing a triazole ring (see Formula 19).

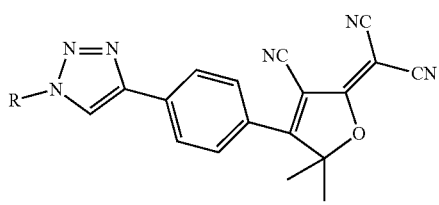

Formula 19 click product of alkyne flurogen with R—N$_3$

Some of the desired pi-acceptor groups will now be discussed in greater detail.

In Formula 12, the acceptor, DCM, is attached to a phenylvinyl pi group characteristic of DCM laser dyes. Again, the molecule will be a photoreactive fluorogen when the open (donor) site contains an azide and a dye or fluorescent fluorophore when the azide is converted to an amine group, or other donor group. Moreover, the various additional open sites on the molecule can be substituted to modify its properties. These substitutions may occur on the DCM heterocycle acceptor ring or on the remaining pi section and such substitutions may include reactive site suitable for bioconjugation.

Another representative pi-acceptor is nitrobenzoxadiazole (NBD) which is a compound having the formula set forth in Formula 13. Here again the open (donor) site will be an azide in the fluorogen NBD-azide and when converted to an amine, or other donor group, the entire compound will be a fluorophore. While Formula 13 does contain a pi system, the benzoxadiazole ring, it can optionally contain one or more of the above noted, pi components such as a vinyl or substituted vinyl group and/or a phenyl or a substituted phenyl group. In this system the nitro group serves as the primary acceptor group. In the related DBD systems a sulfonamide functions as the acceptor.

Another suitable pi-acceptor is stilbazolium as set forth in Formula 14. The open (donor) site will be an azide in the fluorogen and an amine in the fluorophore or fluorescent dye product. The substituent R is particularly useful as a site for functionalization and the components of the pi also serve as sites for additional substitution. The primary acceptor here is the pyridinum ion and the remaining phenylvinyl part serves mostly as part of the pi system. The stilbazolium dyes have many applications, are of particular interest as potential-sensitive dyes for membrane studies when the open site is, for example, a dialkylamino group and are also used as nonlinear optical materials including multiphoton applications. See, for example, C. Zhan, 2006, *Optical Materials*, 28, pp. 289.293.

An example of an azide fluorogen is set forth in Formula 15 wherein the pi-acceptor is the same as that set forth in Formula 11. R$_1$ and R$_7$ of Formula 15 are as set forth herein above and hereby incorporated by reference and R$_3$ can be the same as either R$_1$ or R$_2$. The pi-acceptor of Formula 11 can be modified as shown in Formula 15 wherein n is 0 to about 4 (but usually n=0 or 1), wherein Ar of the pi is an aromatic ring moiety as noted above such as a benzene ring, a naphthalene ring, etc., and wherein R$_3$ is an optional group on the pi and can be a wide range of groups similar to those found in R$_1$ and R$_2$, hereby fully incorporated by reference.

Preparation of Fluorophores—Phothoactivation Route (P-ATA)

Fluorogens of the present invention are generally result from addition of an azide group to any of the pi-acceptor structures set forth in Formulas 10 through 14, 17, and 18.

The photoactive compounds of the present invention such as the various fluorogen-azides are converted to the amine and become fluorescent upon exposure to incident light with wavelength within (i.e. resonant with) their absorption band (P-ATA process) or by multiphoton processes. Upon termination of the ultraviolet or visible photoactivating light, photoconversion from an azide to an amine ceases. The rate of photoconversion can be varied with the wavelength and intensity of the activation light. Accordingly, photoconversion can be controlled with a variety of light sources (e.g. laser, Xe lamp, Hg lamp, laser diodes, etc.).

The preferred wavelengths for the near-ultraviolet or visible photoactivating light can be different for different specific fluorophores, and is determined primarily by the absorption band of the azide-functionalized fluorogen. While such wavelengths will vary with respect to converting a fluorogen to a fluorophore, often the wavelength is from about 300 to about 600 nm, desirably and from about 350 to about 500 nm, and preferably from about 365 to about 450 nm. Upon exposure to the ultraviolet or visible photoactivating light that is resonant with the fluorogen, the azide group degrades and releases N$_2$ producing a highly reactive nitrene end group. Depending on its environment, e.g. the solvent and its components, for example cytosol, and mode of reaction, the nitrene can produce a primary, secondary, or tertiary amine (the last case, for example, may include an aziridine as well as an amine with two alkyl groups attached). Formation of an amine functioning as a terminating electron donor group gives rise to a donor-pi-acceptor fluorophore. The donor-pi-acceptor fluorophore compounds of the present invention are fully conjugated. That is, progressing from the donor through the acceptor, every other bond is a multiple bond, e.g., an alkene or acetylene pi bond. No catalysts are required for the photochemical reaction, but removal of oxygen gas from the sample may increase the overall conversion of the azide to amine. Also, higher concentrations of the photochemical fluorogens will result in higher brightness and labeling density.

An electron donor, especially an amine donor, is a critical component of the donor-pi-acceptor system that comprises a push-pull chromophore or fluorophore with regard to the photo, alkene, and alkyne reactions. The amine donor is a trivalent nitrogen atom and it bears an electron pair which may delocalize into the pi system and ultimately to the acceptor group. One bond from the nitrogen atom will be attached to the pi system and the other two bonds will be to other atoms which are usually chosen from hydrogen, alkyl carbon ($C_1$ to $C_5$, $C_{10}$, or $C_{15}$) or aryl or alkyl aryl carbon ($C_6$ to $C_{15}$). The donor nitrogen atom can also have a bond to a second heteroatom such as a nitrogen or oxygen. The $H_2N$ group is the simplest amine donor, the $H(CH_3)N$ group is the simplest monoalkylamine donor, HPhN is the simplest monoaryl donor, $(CH)_2N$ is the simplest dialkylamine donor and $Ph_2N$ is the simplest diarylamine donor. The one or more phenyl groups, independently, can be substituted and contain from 1 to 15 carbon atoms, Numerous other alkyl, branched alkyl, functionalized alkyl and/or phenyl, substituted phenyl groups and heterocycle, (e.g. O, S, or halide) groups can be substituted on the nitrogen donor atom. The heterocyclic group can contain a total of 3 to about 12 atoms including one or more of O, S, N, halide, and the like. The nitrogen donor atom may also be part of a ring as in the cases of piperidine, tetrahydroquinoline, julolidine, indole or carbazole as representative examples.

After photochemical activation by ultraviolet or visible light, the amine compounds of the present invention are highly fluorescent by subsequent exposure to visible light that is resonant with the absorption band of the fluorophore, but not necessarily resonant with the azide substituted fluorogen precursor. As is generally the case with DCDHF systems the amount of fluorescent light generated can also vary depending upon the polarity and viscosity of the solvent or environment in which it is contained. Generally suitable solvents or environments include hydrocarbons, ethers, halogenated solvents, alcohols such as ethanol, water, polymers, and biological environments that are water-rich. Once the fluorophore of the present invention has been generated and is utilized in a biological entity such as a live cell, a fluorescent label is formed that can be imaged (i.e. excited) at wavelengths generally greater than 500 nm, desirably from about 514 to about 633 nm, and preferably from about 532 to about 633 nm, to avoid cellular autofluorescence.

An important example fluorophore of the present invention is compound 2 of FIG. 2a, that is (E)-2-(4-(4-aminostyryl)-3-cyano-5,5-dimethylfuran-2(5H)-ylidene)malononitrile, and the schematic preparation thereof is set forth in FIG. 2a. The synthesis of compounds 1 and 2 set forth in FIG. 2a will now be described, followed by the chemical analysis of the photoproducts thereof, followed by the various methods utilized to obtain the chemical analysis, including sample preparation, bulk spectroscopy, microscopy, single-molecule photon-count analysis, photobleaching and photoconversion quantum yields, and live cell imaging.

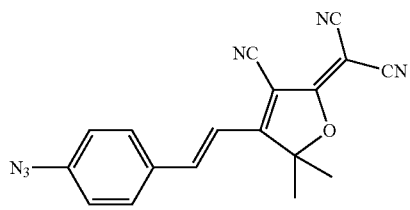 [SMILES: CC1(C)OC(=C(C#N)C#N)C(C#N)=C1/C=C/c1ccc(N=[N+]=[N-])cc1]

2-{4-(4'-Azidophenylethenyl)-3-cyano-5,5-dimethyl-5H-furan-2-ylidene}-malononitrile—Compound 1 of FIG. 2a The 4-azidobenzaldehyde (2.00 g, 13.6 mmol) and 3-cyano-2-dicyanomethylene-4,5,5-trimethyl-2,5-dihydrofuran (2.70 g, 13.6 mmol) were dissolved in 90 mL pyridine and a few drops of acetic acid were added. The mixture was stirred at room temperature for 24 h, poured into water, stirred for 30 min, kept in the refrigerator overnight, and then the precipitate was filtered off and air dried. The material was further purified by silica-gel column chromatography using hexane/EAC (7:3) as eluent and then finally recrystallized from dichloromethane/1-propanol to give the product as a solid (2.00 g, 44% yield). Mp 177-178° C.; IR (neat, cm$^{-1}$) 3060, 2992, 2227, 2118, 1575, 1526, 1380: $^1$H NMR (400 MHz, CDCl$_3$, δ): 7.65 (d, J=8.4 Hz, Ar, 2H), 7.61 (d, J=16 Hz, vinyl, 1H), 7.13 (d, J=8.4 Hz, Ar, 2H), 6.97 (d, J=16 Hz, vinyl, 1H), 1.80 (s, CH$_3$, 6H). $^{13}$C NMR (100 MHz, CDCl$_3$, δ) 174.5, 173.19, 145.65, 144.52, 130.48, 130.18, 119.84, 114.00, 111.27, 110.52, 109.94, 97.30, 26.23: UV-vis (CH$_2$Cl$_2$): $\lambda_{max}$=433 nm; Anal. Calcd for C$_{18}$H$_{12}$N$_6$O: C, 65.85; H, 3.68; N, 25.60. Found: C, 65.58; H, 3.74; N, 25.94.

Compound 2 of FIG. 2a (E)-2-(4-(4-Aminostyryl)-3-cyano-5,5-dimethylfuran-2(5H)-ylidene)malononitrile

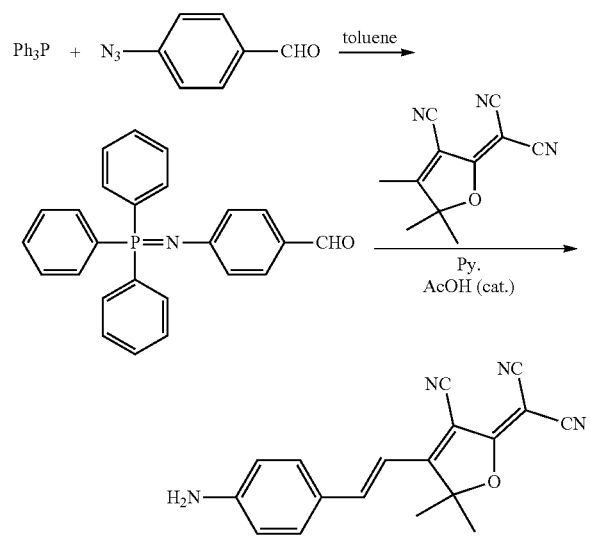

Triphenylphosphine (0.43 g, 1.6 mmol) and anhydrous toluene (12 mL) were added to a 100-mL two-neck round-bottom flask equipped with an additional funnel. The mixture was cooled in an ice-water bath. Next, 4-azidobenzaldehyde (0.30 g, 2.0 mmol) was dissolved in toluene (3 mL) in the additional funnel and added to the reaction mixture dropwise over 10 min. The reaction was continued at 0° C. for 1 h. TLC showed complete conversion of 4-azido-benzaldehyde to one main product. The reaction was stopped and the solvent was removed by rotary evaporation. The remaining solid was recrystallized from 1-propanol and hexane to give the desired azaphosphane benzaldehyde as light yellow solid (0.54 g, 89% yield). IR (neat, cm$^{-1}$): 2965, 1660, 1586, 1504, 1463, 1338, 1156, 1105, 1010, 743, 719; $^1$H NMR (400 MHz, CDCl$_3$, δ): 9/1 (s, 1H), 7.81-7.72 (m, 6H), 7.63-7.47 (m, 11H), 6.82 (d, J=8.8 Hz, 2H); $^{13}$C NMR (100 MHz, CDCl$_3$, δ); 190.5, 132.6, 132.5, 132.3, 131.5, 129.0, 128.9, 123.2, 123.0. This material was of sufficient purity for direct conversion to the amine.

The azaphosphane benzaldehyde (0.38 g, 0.001 mol), 2-(3-cyano-4,5,5-trimethyl-5H-furan-2-ylidene)-malononitrile (0.199 g, 0.001 mol), pyridine (8 mL), and acetic acid (0.2 mL) were added to a 100-mL round-bottom flask with stirbar. The mixture was warmed to 40° C. and kept at this temperature for 3 days and the reaction was monitored several times by TLC, which showed one purple product with high polarity was formed as the main product. The reaction was stopped and solvent was removed by rotary evaporation. The remaining solid was poured into ice water (200 mL) and stirred for 3 h. The precipitate was filtered off by suction filtration and recrystallized from a mixture of 1-propanol and dichloromethane to give the desired title compound as a purple solid (0.23 g, 77% yield). Mp 360° C.; IR (neat, cm$^{-1}$): 3487, 3366, 2229, 1643, 1519, 1496, 1265, 1169, 1111, 836; $^1$H NMR (400 MHz, DMSO, δ): 7.88 (d, J=16.0 Hz, 1H), 7.68 (d, J=8.8 Hz, 2H), 6.86 (broad s, 2H), 6.82 (d, J=16.0 Hz, 1H), 6.66 (d, =8.8 Hz, 2H), 1.74 (s, 6H); $^{13}$C NMR (100 MHz, CDCl$_3$, δ): 177.9, 176.1, 155.8, 150.4, 134.1, 122.5, 114.7, 114.0, 113.2, 112.6, 108.2, 98.6, 92.0, 51.1, 26.1, UV-vis (CH$_2$Cl$_2$): $\lambda_{max}$=500 nm, $\epsilon$=3.1×10$^4$ M$^{-1}$ cm$^{-1}$.

Compound 3 of FIG. 2a (E)-2-(3-Cyano-5,5-dimethyl-4-(4-nitrostyryl)furan-2(5H)-ylidene)malononitrile

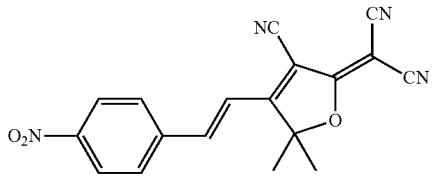 [SMILES: CC1(C)OC(=C(C#N)C#N)C(C#N)=C1/C=C/c1ccc([N+](=O)[O-])cc1]

To a 100-mL round-bottom flask with stirbar was added 4-nitrobenzaldehyde (0.30 g, 0.002 mol), 2-(3-cyano-4,5,5-trimethyl-5H-furan-2-ylides (0.44 g, 0.0022 mol), pyridine (5 mL), and acetic acid (several drops). The reaction mixture was reacted at room temperature for 24 h. TLC showed that an orange product had been formed as the main product, but a small amount of 4-nitrobenzaldehyde still remained. The reaction was warmed to 40° C. and continued for another 24 h. The reaction was stopped and cooled to room temperature. The reaction mixture was poured into ice water (500 mL) and stirred for 4 h. The brown precipitate was isolated by suction filtration and recrystallized from 1-propanol to give the desired product as a light brown powder (0.40 g, 67% yield). Mp 281° C.; IR (neat, cm$^{-1}$): 3084, 2220, 1581, 1521, 1345, 1105; $^1$H NMR (400 MHz, CDCl$_3$, δ): 8.34 (d, J=8.8 Hz, 2H), 7.80 (d, 8.8 Hz, 2H), 7.68 (d, J=16.8 Hz, 1H), 7.12 (d, J=16.4 Hz, 1H), 1.83 (s, CH$_3$, 6H); $^{13}$C NMR (100 MHz, CDCl$_3$, δ): 171.9, 149.6, 143.2, 139.4, 129.3, 124.6, 118.5, 110.9, 110.1, 109.6, 97.7, 26.2.

Other DCDHF type fluorophores that are fully conjugated are set forth in U.S. Pat. Nos. 6,750,603, 6,864,375, and U.S. Patent Application Publication 2005/0009109 A1, hereby fully incorporated by reference.

Various of the above examples were analyzed with regard to chemical analysis, bulk spectroscopy, fluorescence microscopy, single-molecule photon counts, photobleaching and photoconversion quantum yields, and live-cell imaging as follows.

Samples for bulk chemical studies were photoconverted, both with and without removing dissolved oxygen by bubbling N$_2$, and analyzed using NMR and HPLC-MS. Samples of the azide DCDHF (compound 1 in FIG. 2a) that were left in the dark were stable for months.

Column chromatography and NMR: A solution of photoconverted azido DCDHF (compound 1 in FIG. 2a) in ethanol was separated on a TLC plate (1:3 acetone:dichloromethane) into two bands: a red band with lower R$_f$ that was fluorescent under ultraviolet light (365 nm) and a yellow band with higher R$_f$ that was nonemissive; the yellow band was not present when the solution of 1 was deoxygenated by bubbling N$_2$ before and during photoconversion, (Adequate separation was not achievable using dichloromethane and hexanes or dichloromethane alone; therefore, we resorted to acetone in the mobile-phase solvent mixture.)

For column chromatography, the photoproducts were separated on a column using silica gel as the stationary phase and 2:1 hexanes:acetone as the mobile-phase solvent. Two bands were well separated: a yellow band of nitro (compound 3 in FIG. 2a) eluted first, been a red band of amine (compound 2 in FIG. 2a) eluted later. $^1$H NMR spectra of column-separated photoproducts confirm these identifications, as compared to pure, synthesized samples (although the yellow band was contaminated with some other minor photoproducts):

(E)-2-(4-(4-Aminostyryl)-3-cyano-5,5-dimethylfuran-2(5H)-ylidene)malononitrile Compound 2 (photoconverted from compound 1, column separated): $^1$H NMR (400 MHz, CDCl$_3$, δ): 7.58 (d, J=16 Hz, vinyl, 1H), 7.50 (d, J=8.4 Hz, Ar, 2H), 6.80 (d, J=16 Hz, vinyl, 1H), 6.70 (d, J=8.8 Hz, Ar, 2H), 4.39 (s, NH$_2$, 2H), 1.76 (s, CH, 6H).

(E)-2-(3-Cyano-5,5-dimethyl-4-(4-nitrostyryl)furan-2 (5H)-ylidene)malononitrile Compound 3 (photoconverted from compound 1, crude, column enriched); $^1$H NMR (300 MHz, CDCl$_3$, δ): 8.34 (d, J=8.7 Hz, Ar), 7.80 (d, 8.4 Hz, Ar), 7.69 (d, J=11 Hz, vinyl), 7.12 (d, J=14 Hz, vinyl), 1.83 (s, CH$_3$).

Purification of 2 and 3 by semi-prep HPLC: An ethanolic solution containing ~1 mg/mL fluorogenic azide (compound 1 in FIG. 2a) was photoconverted using a 150-W Xe lamp for 5 min under air. Photoproducts compounds 2 and 3 were separated by HPLC on a Hypersil Hyper Prep 100 BDS-C18 column (10.0×250 mm) with linear gradient elution (5-100% acetonitrile over 25 min, 5 min hold at 100% acetonitrile; balance by volume., 0.1 M tetraethylammonium acetate buffer, pH 7.5; total flow rate, 4 mL/min). The UV-N is absorption spectrum of the column eluent was continuously monitored using a Shimadzu diode array detector (SPD-M10A). Under these conditions, compounds 2 and 3 exhibited retention times of 20.9 and 22.5 min, respectively. No azide compound 1 (RT=23.6 mm) after photoactivation.

HPLC-MS characterization of photoproducts: Ethanolic solutions of compound 1 were photoconverted using diffuse 407-nm laser light under nitrogen (dissolved oxygen removed by bubbling N$_2$) or air. The photoactivation products were analyzed by HPLC-MS (Waters 2795 Separations module with 2487 Dual λ Absorbance Detector; Waters Micromass ZQ mass spectrometer). Gradient elution (2-95% acetonitrile with 0.1% formic acid over 20 min, 10 min hold at 95% acetonitrile/formic acid; balance by volume, water with 0.1% formic acid) through a C18 column (2.1×40 mm) was employed for the separation. The column eluent was subjected to electrospray ionization, and positive and negative ions with m/z from 100-1000 amu were detected.

In the absence of oxygen, photoconversion of azide compound 1 in ethanol produced amine compound 2 (RT=11.36 min; ESI$^-$: m/z=301.7, [M−H]$^-$; ESI$^+$: m/z=303.5, [M−H]$^+$) as the only major photoproduct. A putative azo dimer (RT=16.97 min; ESI$^-$: m/z==599.7, [M−H]$^-$) was observed as a minor photoproduct.

In air, photoactivation of 1 in ethanol produced a mixture of amine compound 2 (RT=11.43 min; ESL: m/z=301.5, [M−H]$^-$; ESI$^+$: m/z 303.4, [M+H]$^+$) and nitro 3 (RT=12.99 min; ESI$^-$: m/z=331.5, [M−H]$^-$, 315.5 [M—O—H]$^-$, 301.5 [M-2O—H]$^-$) as major products. After several days in air and room lights, an unidentified species believed to be generated from compound 3 formed in the solution (RT=19.15 min; ESI$^-$: m/z=367.6).

Samples for aqueous bulk photostability measurements and quantitative single-molecule measurements were prepared using 5% (by mass) gelatin (type A, Bloom ~200, MP Biomedicals) in purified water. The gelatin solution was liquefied at 37° C. A small volume (<0.5 μL) of dye stock solution in dimethyl sulfoxide was mixed with 10 μL gelatin, sandwiched between two Ar-plasma-etched glass coverslips, and allowed to gel at room temperature.

Polymer samples were prepared in 1% (by mass) solutions of poly(methyl methacrylate) (PMMA, $T_g$=105° C., MW=75,000 g/mol, atactic, polydispersity ~2.8, PolySciences Inc.) in distilled toluene doped with nanomolar fluorophore concentrations; these solutions were then spin-cast onto Ar-plasma-etched glass coverslips to produce films 30 nm thick as measured by ellipsometry, (Distillation and plasma-etching were performed to remove fluorescent impurities.)

Bulk solution absorption and emission spectra were acquired on a Perkin-Elmer Lambda 19 UV-vis spectrometer and a SPEX Fluoromax-2 fluorimeter using standard 1-cm path length, quartz cuvettes. Fluorescence quantum yields were referenced against standards with known quantum yields, corrected for differences in optical density and solvent refractive index. Fluorophore compound 2 in ethanol was measured against Texas Red in ethanol ($\Phi_F$=0.93). All quantitative measurements were done at low concentrations (absorbance values less than 0.2) to avoid any complications with dimer or aggregate formation. Molar absorption coefficients were measured from dilutions of solutions with known concentrations.

Samples were studied using en Olympus IX71 inverted microscope in an epifluorescence configuration using 594-nm illumination from a HeNe laser (Meredith Instruments, 5 μW output); the irradiance at the sample was approximately 0.5-1.0 kW/cm$^2$. The emission was collected through a 100×, 1.4 N.A. oil-immersion objective, filtered using a 594RDC dichroic and HQ615LP long-pass filter (Chroma Technology) to remove scattered excitation light, and imaged onto an electron-multiplication Si EMCCD camera (Andor iXon+) with integration times of 20-100 ms. Photoactivation was performed using a 150-W Xe lamp or the 407-nm line from a Kr-ion laser (Coherent Innova-301); irradiances at the sample were generally less than 50 W/cm$^2$. Singles of compound 2 blinked more often than most secondary- and tertiary-amine DCDHFs. However, no oxygen scavengers were used for any imaging; including oxygen scavengers, triplet quenchers, or bathing the sample with inert gases such as $N_2$ or Ar may reduce blinking, increase photostability, and reduce nonemissive photoproducts.

All image analysis was performed using the ImageJ program (NIH). Single-molecule movies were used to extract the total number of detected photons before photobleaching, where all the photons (minus background) contributing to a single-molecule spot were spatially and temporally integrated. Results were plotted using the probability distribution of photobleaching: P=$m_N$/M, the ratio of the number of bleached singles in surviving after a given number of photons emitted N to the total number of molecules M in the measurement set. This curve was fit using one or two exponential decays, and the decay constant was extracted from the fit (Equation 2). The probability distribution approach for determining average photons emitted avoids any artifact from choice of bin size, and gives comparable results to histogramming.

The EM gain and conversion gain (defined as the number of A-to-D converter counts per photoelectron) were used to convert counts to photoelectrons; the linear EM gain was measured at various software settings, and the conversion gain from the manufacturer is 26.12 e$^-$/count. It is also useful to calculate the number of emitted photons $N_{tot,e}$ by correcting the measured value of detected photons using the collection efficiency of our setup (D $\eta_Q F_{coll} F_{opt} F_{filter}$), which is the product of the camera quantum efficiency $\eta_Q$, the angular collection factor $F_{coll}$ determined by the objective NA, the transmission factor through the objective and microscope optics $F_{opt}$, and the transmission factor through the various filters $F_{filter}$, respectively. At the emission wavelengths, $\eta_Q$ 92% for our camera, the maximum possible $F_{coll}$ for our setup is 38% in PMMA and 45% in gelatin for a single dipole emitter aligned horizontally, we measured $F_{opt}$ for our setup to be 50%, and we measured $F_{filter}$ to be 50% for the filter set we used This yields $D_{PMMA}$=8.7% and $D_{gelatin}$=10.3%.

The photobleaching quantum yield is defined as the probability of photobleaching after absorbing a photon, or the ratio of the bleaching rate $R_B$ to the rate of absorbing photons $R_{abs}$:

$$\Phi_{B(P)} = \frac{R_{B(P)}}{R_{abs}} = \frac{1}{\tau_{B(P)} R_{abs}} = \frac{1}{\tau_{B(P)} \sigma_\lambda I_\lambda \left(\frac{\lambda}{hc}\right)}, \quad \text{(Equation 1)}$$

where $\tau_{B(P)}$ is the decay constant in the exponential fit, the absorption cross-section is related to the molar absorption coefficient by the equation $\sigma_\lambda$=(1000)2.303$\epsilon_\lambda$/$N_A$=9.37× 10$^{-17}$ cm$^2$ for compound 1, $I_\lambda$ is the irradiance at the sample, λ is the excitation wavelength, h is Planck's constant, and c is the speed of light. The average decay constant for a two-exponential fit, $$F = \sum_{i=1}^{n=2} \alpha_i e^{(-i/\tau_j)},$$

is given by:

$$\tau = f_1 \tau_1 + f_2 \tau_2 = \frac{\alpha_1 \tau_1^2 + \alpha_2 \tau_2^2}{\alpha_1 \tau_1 + \alpha_2 \tau_2}, \quad \text{(Equation 2)}$$

where $f_i = \alpha_i \tau_i / \Sigma_j \alpha_j \tau_j$ is the fractional area under the multi-exponential curve (Some other papers use $t_{90}\%$, the irradiation time in seconds for 90% conversion to product, as a more practical measure than the decay constant $\bar{\tau}$; compare values carefully.) Photobleaching quantum yield scales with the inverse of total number of photons emitted, and a lower value for $\phi_B$ indicates better photostability.

Figure 2C:
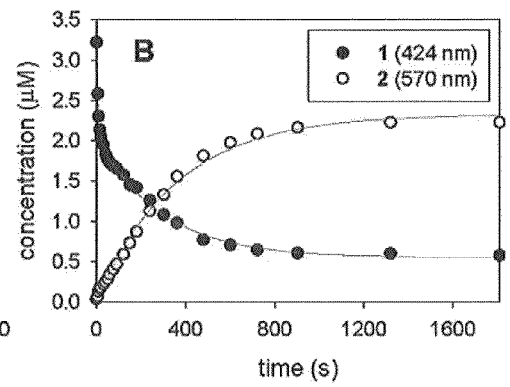

Photoconversion by diffuse 407-nm laser light (3.1 mW/cm$^2$) was monitored as shown in FIG. 2c by measuring changes over time in absorbance values of the reactant and photoproduct of interest in ethanol bubbled with $N_2$. The quantum yield of photoconversion $\phi_P$ is defined in Equation 1 above, with $T_P$ as the average decay constant from the exponential fit of the decaying absorption values for the starting material. Note that $\phi_P$ is the probability that the starting material will photoconvert for each photon absorbed; only a fraction of those photoconverted molecules become fluorescent (69% in ethanol).

For details of cell culture, see reference, Vrijic, M., et al., *Biophys. J.*, 2005, 88, pp. 334-347. Chinese hamster ovary (CHO) cells were plated on fibronectin-coated borosilicate chambered coverslips overnight prior to imaging. CHO cells were treated with 1-μM fluorogen solution (1-mM dye stock in ethanol into growth medium) at 37° C. for 1 hr, followed by PBS buffer rinses to remove excess extracellular fluorogen. Briefly, cells were imaged at 22° C. in supplemented PBS buffer. That is, imaging was performed within 45 min after removing the cell tray from the 37° C. incubator to ensure cell viability.

For imaging, the irradiance of the 594-nm laser was 500 W/cm$^2$ for high-magnification cell images, and 20 W/cm$^2$ for low-magnification images; the 407-nm laser irradiance for photoactivation ranged from <1 to 35 W/cm$^2$.

Figure 5:
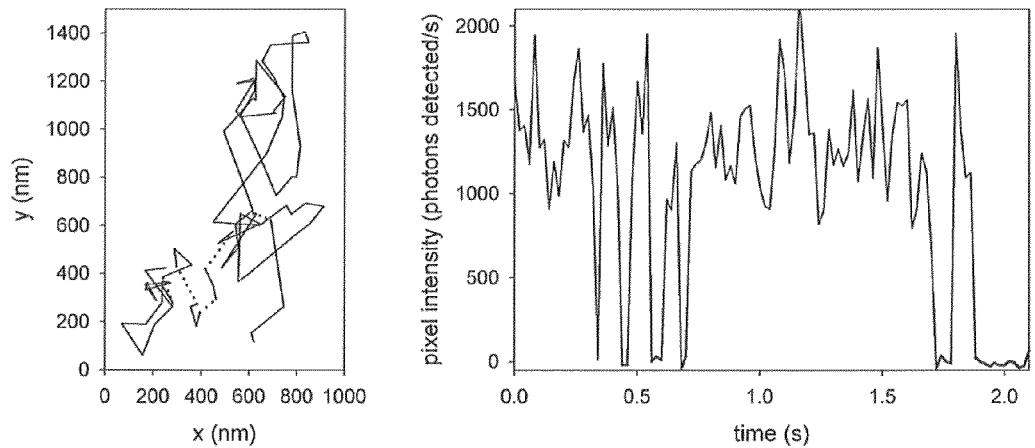
FIG. 5 (left) shows the trajectory of a single copy of a DCDHF fluorophore diffusing in the membrane of a CHO cell after photoactivation, whereas the right figure discloses a background-subtracted intensity time trace of the molecule in the trajectory of the left figure. More specifically.
Figure 6:
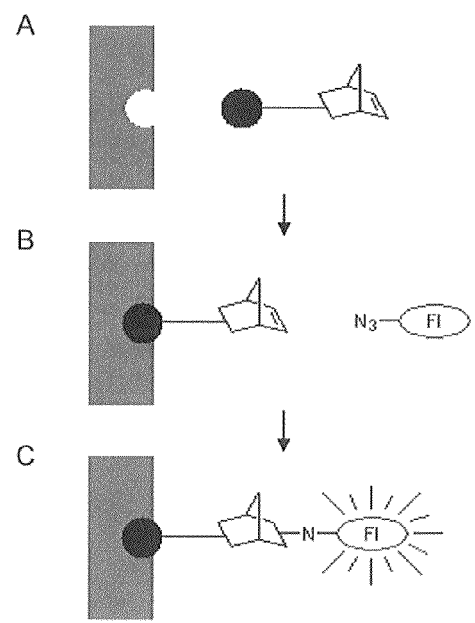
FIG. 6 discloses a method of labeling wherein a biological binding motif bonded to an alkene, such as the strained alkene norbornene, is introduced into a cell, the motif binds to the cell and then a dark fluorogen is reacted with the ligated norbornene to provide simultaneously bioconjugation and creation of the fluorophore. More specifically.

Single-particle tracking in FIG. 5 was performed using ImageJ and the "SpotTracker" plugin, see reference, Sage, D. *Image Processing, IEEE Transactions on* 2005, 14, pp. 1372-1383, with the following parameters; maximum displacement of 5 pixels, intensity factor of 80%, intensity variation of 0%, movement constraint of 20%, and center constraint of 0%.

The evolution of the absorption spectra related to photochemical conversion of fluorogen 1 (FIG. 2a) to fluorophore 2 (FIG. 2a) is shown in FIG. 2b. FIG. 2b shows the decrease in absorption (left side) of the azide fluorogen compound 1 with λmax at 424 nm and the corresponding growth of absorption (right side) of the amine photoproduct 2 with λmax at 570 nm resulting from exposure to 0.0031 \W/cm$^2$ of diffuse 407 nm radiation in ethanol. The amount of time commences with zero at top left curve A, 10 seconds for curve B, 90 seconds for curve C, 150 seconds for curve D, 240 seconds for curve E, 300 seconds for curve F, 480 seconds for curve G, and 1,320 seconds for curve H. Thus, FIG. 2b shows that irradiation of the fluorogen 1 at 407 nm leads to loss of the azido DCDHF absorption at 424 nm and the formation of longer wavelength absorption at 570 nm as in a biological label entity. The azide fluorogen does not absorb at 594 nm, but the amine photoproduct does strongly absorb. Irradiation at wavelengths in the absorption band of the amine produces strong fluorescence. The fluorophores having a DCDHF acceptor generated from the azides share the other beneficial properties of other DCDHF dyes, namely photostability and environmental sensitivity wherein the wavelength and intensity of fluorescence is influenced by the solvent polarity and viscosity.

FIG. 2c sets forth the photochemical production of micromolar concentrations of the primary amine compound 2 as a function of time and the corresponding decrease in the amount of fluorogen compound 1. The production of the primary amine compound 2 was approximately 69% by concentration, whereas the yield of the nonfluorescent nitro compound 3 was minor. The secondary-amine compound 4 is hypothetical and represents the product of reaction of the nitrene with a biological substrate "R". Other unidentified minor products were present in the photoproduct mixture.

The azide-fluorogen compound (1 in FIG. 2a) as well as the primary amine compound 2 were tested with regard to photophysical properties in ethanol and the results listed in the table below were obtained. (This is one embodiment of the azide fluorogen system, and other embodiments can have different photophysical parameters.) Before photoactivation, the azide fluorogen 1 absorbs in the "A" curve with λmax at 424 nm in ethanol; when activated or pumped at these short blue wavelengths, the fluorogen emits fluorescence at 552 nm, but it is nonemissive when pumped at longer wavelengths (e.g. 594 nm). Illumination with 407-nm laser light or the light from a Xe or Hg lamp causes the azide fluorogen to photoconvert to other compounds, including the fluorescent amine product 2. The efficiency of this photoconversion is measured by the quantum yield of photoconversion ($\Phi_P$), which is the probability of photoconverting the azide to amine with each photon absorbed by the fluorogen, Photoactivation requires only low-intensity irradiation. After photoactivation, the amine fluorophore 2 absorbs at longer wavelengths (e.g. 594 nm) where the fluorogen does not absorb and where autofluorescence in the cell is low. Therefore, when imaging using 594 nm, only the photoactivated molecules 2 are visible and the unactivated fluorogen 1 of FIG. 2a is dark. The quantum yield of fluorescence ($\Phi_F$) quantifies how many fluorescent photons the fluorophore emits for every photon absorbed; it is relatively low in ethanol and water, but gets much higher (up to around 40%) in rigidified environments such as ice or cell membranes or biomolecules. The quantum yield of photobleaching ($\Phi_B$) quantifies the probability of photodestruction of the fluorophore for every photon absorbed; the very low value for the fluorophore, 2 indicates that it resists photobleaching and emits many photons prior to eventual bleaching. The average number of photons emitted per molecule before permanent photobleaching, measured one molecule at a time in a polymer film or in gelatin, is reported as "SM $N_{tot,e}$." Because the fluorophore emits millions of photons, it can be imaged for a relatively long time with a high signal-to-background ratio. Imaging single molecules in living cells has stringent prerequisites, foremost among them is photostability; most DCDHF fluorophores are quite photostable, and the photoproduct 2 is no exception.

| Compound | $\lambda_{abs}$ (nm) | $\lambda_{fl}$ (nm) | $\epsilon_{max}$ (M$^{-1}$cm$^{-1}$) | $\Phi_F$ | $\Phi_P$ (a) | $\Phi_B$ (b) | SM $N_{tot,e}$ (c) |
|---|---|---|---|---|---|---|---|
| 1 | 424 | 652 | 29,100 | — | 0.0059 | — | — |
| 2 | 570 | 613 | 54,100 | 0.025 (d) | — | 4.1 × 10$^{-6}$ | 7.2 × 10$^6$[2.3 × 10$^6$] |

(a) quantum yield of photoactivation from 407 nm illumination using measured average decay time constant
(b) bulk photobleaching quantum yield, measured in aqueous gelatin
(c) average number of photons emitted per molecule in PMMA[gelatin], measured molecule-by-molecule
(d) fluorescence quantum yield in ethanol; much higher in rigid environment In FIG. 2a, replacing the usual amine donor group in fluorophores containing a DCDHF acceptor with the mildly electron-withdrawing azide disrupts the donor-pi-acceptor push-pull character observed with the amine present. This explains the large (~150-nm) red-shift of the absorption wavelength relative to the azido DCDHF fluorogen, and thus the azido-DCDHF is not in resonance with the longer-wavelength excitation laser. The curve labeled G is not the final photostate presented, rather that is H (underneath the dashed line). Electron-withdrawing substituents (i.e., the DCDHF acceptor) on an aryl azide appear to stabilize the nitrene intermediate in an alcohol solvent, and aniline products rather than azepines are produced (Soundararajan, N.; Platz, M. S. *J. Org. Chem.* 1990, 55, 2034-2044), In fact, HPLC-MS and NMR analysis of the photoproducts of 1 confirm structure 2 as the major product in ethanol. Compound 2 was also independently synthesized and is identical to the sample of 2 prepared photochemically.

Figure 3:
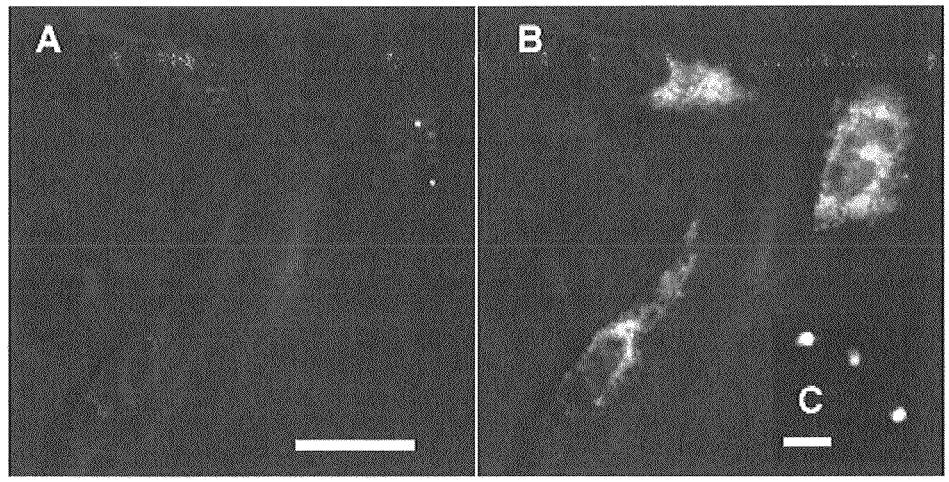
FIG. 3 relates to three CHO cells incubated with a fluorogen before (FIG. 3A) and after (FIG. 3B) activation of the fluorogen utilizing diffuse 407-nm light, whereas FIG. 3C (inset) shows single photoactivated molecules fluorescing in a cell under higher magnification. More specifically.

An example of a specific azide-fluorogen compound will now be set forth in regard to various properties thereof including fluorescence and generation of fluorescence in a Chinese hamster ovary (CHO) cell. For quantitative analysis, single molecules were easily activated and imaged in polymer films and in aqueous gelatin. But a crucial test is whether an azide-fluorogen can also be photoactivated in living cells. FIG. 3 shows three Chinese hamster ovary (CHO) cells growing on a glass slide and incubated with the azide-fluorogen of FIG. 2, which easily inserts into and penetrates the cell plasma membrane. Fluorescence in the cytosol turns on only after exposure of the cell to a short flash of diffuse violet light. A fraction of the fluorophores produced remained stationary at the activation site, presumably bioconjugated to relatively static biomolecules (here the nitrene has reacted with some cell component other than the cytosol). The remaining untethered fraction of chromophores produced was free to move throughout the cell and single molecules were visible diffusing in the cell.

Figure 4:
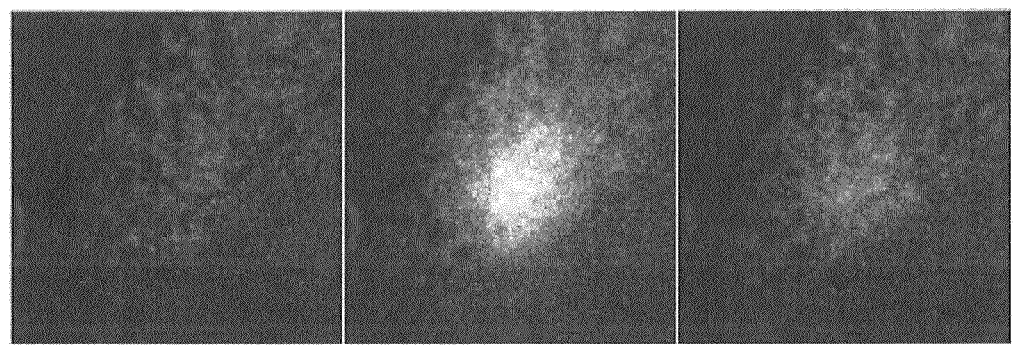
FIG. 4 discloses three photos of a CHO cell incubated with a fluorogen before (left), immediately after (middle), and after a three second activation (right) by focused 407-nm light. More specifically.

A CHO cell imaged at higher magnification was activated with tightly focused 407-nm light and the results are shown in FIG. 4.

The spatial trajectory of a single copy of the activated fluorophore could be monitored moving in a CHO cell membrane and the result is set forth in FIG. 5.

The photoactivatable compounds of the present invention such as the various azide fluorogen compounds can be photoactivated by ultraviolet or visible light and become fluorescent. In other words, upon photoreaction of the azide to a nitrene and the nitrene chemically converts into an amine compound, a dark fluorogen can be converted by photoactivation into a fluorescent label molecule.

Figure 7:
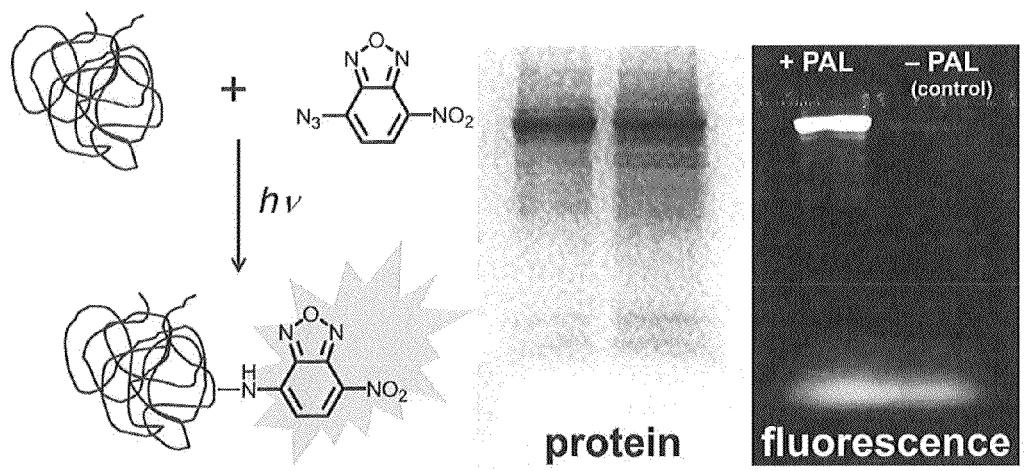
FIG. 7 discloses a method of labeling wherein an azide fluorogen forms a bond to a biomolecule or other object and becomes fluorescent at the same time upon photochemical generation of a reactive nitrene. The resulting fluorogenic photoaffinity labeling (PAL) can be used to tag nearby biomolecules, proteins, cells, or other objects. The figure also shows a gel electrophoresis experiment that demonstrates PAL attachment of an azide fluorogen to proteins in a cell accompanied by generation of fluorescence. More specifically, FIG. 7 (left) shows a schematic of fluorogenic photoaffinity labeling (PAL) of proteins. The nitrene intermediate of the photoconversion of an azide to an amine is reactive enough to insert into bonds of nearby biomolecules. The cross-linking reaction simultaneously turns-on fluorescence and covalently links the probe to the biomolecule. The fluorogen here is NBD-azide.

Activated fluorophores of the type in the present invention were bright enough to be detected above the cellular background, with red enough absorption to avoid pumping cellular autofluorescence. The activated fluorophores were robust enough to emit millions of photons before photobleaching, small enough not to interfere with, cellular processes, and have the potential to be noncovalently or covalently bound to biomolecules using state-of-the-art targeting schemes (e.g. HaloTag, SNAP-tag, etc.) or using photoaffinity labeling of a binding pocket (via the nitrene intermediate reacting with a nearby biomolecule), (Photoaffinity labeling is demonstrated in FIG. 7.) Thus, the photoactivatable azide-fluorogen compounds of the present invention could be connected or tagged to various biological entities. If incubated with living cells, and/or specifically or nonspecifically labeled to biological molecules, the fluorogens remain dark until activated with light, whereby they are converted to amine-terminated fluorophores. After activation, the fluorophores are rendered fluorescent by visible light and thus biological entities such as cells, biomolecules, molecular motors, organelles, etc., can be located and the path thereof determined. In general, this invention will aid biophysical measurements and/or super-resolution imaging.

The invention will be better understood by reference to the following examples that serve to illustrate, but not to limit the present invention. The synthesis and photophysical, properties of additional fluorogens will be described.

Figure 8:
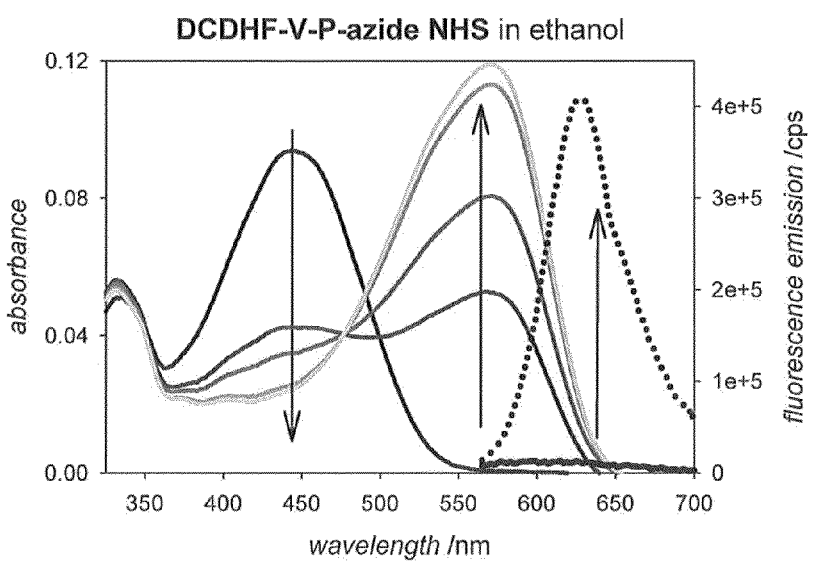
FIG. 8 is the absorbance and fluorescence emission of DCDHF-V-P-azide NHS in ethanol.

Fluorogens with reactivity for bioconjugation can be used, as well. N-hydroxy succinimide (or NHS) groups are used to link the fluorogen to lysines or other biomolecules containing free amines. We have also synthesized an NHS version of the azide-pi-acceptor fluorogen DCDHF-V-P-azide NHS, Formula 16). In ethanol, see FIG. 8, the absorbance peak of this NHS azido fluorogen is 443 nm; the absorbance peak of the amino photoactivated version is 572 nm and the emission peak is 627 nm. The photoconversion can be accomplished with a range of excitations (350-450 nm), and the imaging of the photoactivated fluorophore can be done at 550 nm, or in the range of 525-600 nm.

Formula 16

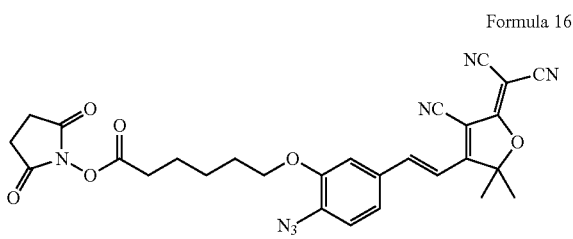 [SMILES: CC1(C)OC(=C(C#N)C#N)C(C#N)=C1/C=C/c1ccc(N=[N+]=[N-])c(OCCCCCC(=O)ON2C(=O)CCC2=O)c1]

6-(5-formyl-2-nitro-phenoxy)-hexanoic acid ethyl ester

JCW-03-015

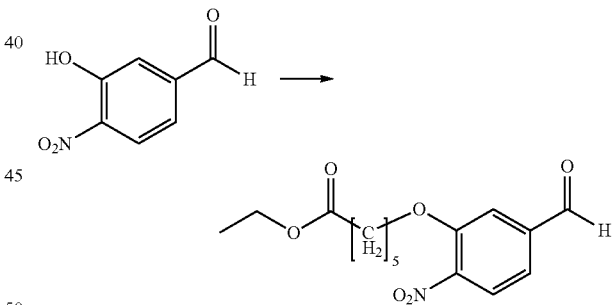

To a solution of 3-hydroxy-4-nitrobenzaldehyde (0.80 g, 4.76 mmol), in DMF (15 mls) was added ethyl 6-bromohexanoate (1.30 g, 5.82 mmol) and potassium carbonate (1.23 g, 8.91 mmol). The mixture was stirred at 70° C., for 12 hours, cooled, poured into water and extracted twice with ethyl acetate. The combined organic fractions were washed once with water and dried over anhydrous magnesium sulfate. After the solvents were removed under reduced pressure, a red oil remained which was purified by column chromatography (70% hexane/30% ethyl acetate) to give 6-(5-formyl-2-nitro-phenoxy)-hexanoic acid ethyl ester as a yellow oil (1.00 g, 67%). $^1$H NMR (400 MHz, CDCl$_3$) δ: 10.06 (s, 1H), 7.92 (d, 1H, J=8.8 Hz), 7.58 (d, 1H, J=1.2 Hz), 7.54 (dd, 1H, J=8 Hz, J=1.6 Hz), 4.20 (q, 2H, J=6.8 Hz), 4.14 (t, 2H, J=7.2 Hz), 2.36 (t, 2H, J=8.0 Hz), 1.90 (m, 2H), 1.73 (m, 2H), 1.57 (m, 2H), 1.29 (t, 3H, J=6.8 Hz) $^{13}$C NMR (400 MHz, CDCl$_3$)

δ: 173.79, 169.46, 151.87, 143.23, 133.66, 125.32, 121.93, 115.88, 69.65, 60.42, 34.12, 28.54, 25.40, 24.52, 14.25. IR (neat): 3396, 3110, 3080, 3047, 2944, 2869, 2735, 1730, 1705, 1607, 1531, 1489, 1465, 1434, 1381, 1351, 1311, 1272, 1161, 1093, 1063, 1030, 961, 863 cm$^{-1}$.

6-(2-amino-5-formyl-phenoxy)-hexanoic acid ethyl ester

JCW-03-016

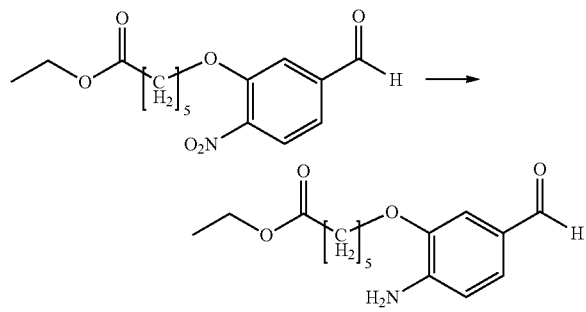

To a solution of 6-(5-formyl-2-nitro-phenoxy)-hexanoic acid ethyl ester (1.0 g, 3.23 mmol) in ethanol (20 ml) and concentrated HCl (5 ml) was added stannous chloride (2.17 g, 11.63 mmol). The mixture was stirred at 70° C. for 90 minutes while being monitored by thin layer chromatography. After cooling to room temperature, the mixture was poured into water (100 ml) and neutralized with a saturated solution of sodium bicarbonate resulting in the precipitation of tin salts and a dark brown oil. The salts were washed with ethyl acetate and the washings were combined with the original filtrate, the aqueous phase was separated and the remaining ethyl acetate phase was dried with magnesium sulfate, filtered and concentrated by rotary evaporation to a brown oil which was purified by column chromatography (45% CH$_2$Cl$_2$, 45% hexane, 10% Et$_3$N). The product, 6-(2-amino-5-formyl-phenoxy)-hexanoic acid ethyl ester, was obtained as a red oil (0.33 g, 35%). An additional 0.32 g of red oil was obtained from the column but found to be a mixture of unidentified byproducts. $^1$H NMR (400 MHz, CDCl$_3$) δ: 9.72 (s, 1H), 7.30 (m, 2H), 613 (d, 1H, J=8.4 Hz), 4.50 (s, 2H), 4.15 (q, 2H, J=7.2 Hz), 4.08 (t, 2H, J=6.8 Hz), 2.35 (t, 2H, J=8.8 Hz), 1.88 (m, 2H), 1.74 (m, 2H), 1.55 (m, 2H) 1.30 (t, 3H, J=6.8 Hz). $^{13}$C NMR (400 MHz, CDCl$_3$) δ: 109.59, 173.60, 146.08, 143.31, 127.78, 127.55, 112.72, 109.11, 68.18, 60.35, 34.20, 28.83, 25.69, 24.61, 14.18. IR (neat): 3481, 3362, 2936, 2868, 2722, 2360, 2341, 2229, 2156, 1964, 1727, 1671, 1612, 1587, 1572, 1517, 1444, 1394, 1368, 1313, 1243, 1164, 1140, 1095, 1029, 864, 817, 789, 748.

6-{2-Amino-5-[2-(4-cyano-5-dicyanomethylene-2,2-dimethyl-2,5-dihydro-furan-3-yl)-vinyl]-phenoxy}-hexanoic acid ethyl ester

JCW-03-019

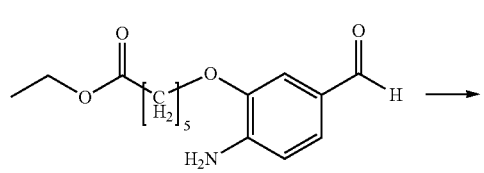

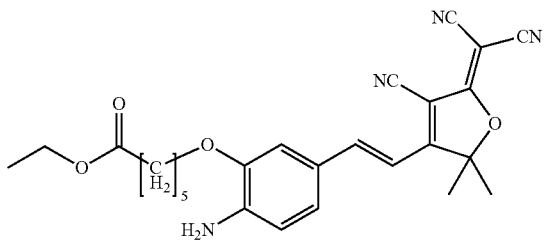

Acetic acid (5 drops) was added to a solution of 6-(2-amino-5-formyl-phenoxy)-hexanoic acid ethyl ester (0.310 g, 1.10 mmol) and 2-(3-cyano-4,5,5-trimethyl-5H-furan-2-ylidene)-malononitrile. (0.26 g, 1.33 mmol) in pyridine (10 ml). After stirring for 24 hours at room temperature, the mixture was diluted with 100 mls of water causing the formation of a dark purple precipitate which was removed by suction filtration and washed with water. The material, was found to be pure 6-{2-amino-5-[2-(4-cyano-5-dicyanomethylene-2,2-dimethyl-2,5-dihydro furan-3-yl)-vinyl]phenoxy}-hexanoic acid ethyl ester by NMR (0.38 g, 75%). Small crystals of this product were obtained by pouring the NMR sample (chloroform) into a small amount of acetone and allowing this solution to slowly evaporate. Mp: 164.5° C. $^1$H NMR (400 MHz, CDCl$_3$) δ: 7.58 (d, 1H, J=16 Hz), 7.17 (dd, 1H, J=8 Hz, J=1.6 Hz), 7.01 (d, 1H, J=1.6 Hz), 6.77 (d, 1H, J=16 Hz), 6.72 (d, 1H, J=8 Hz), 4.70 (s, 2H), 4.16 (q, 2H, J=7.2 Hz), 4.11 (t, 2H, J=6.2 Hz), 2.38 (t, 2H, J=7.2 Hz), 1.91 (m, 2H), 1.78 (s, 6H), 1.76 (m, 2H), 1.61 (m, 2H), 1.28 (t, 3H, $^{13}$C NMR (400 MHz, (CDCl$_3$) δ: 176.06, 174.30, 173.59, 148.75, 146.35, 143.18, 126.97, 124.02, 113.85, 112.40, 111.65, 111.16, 110.20, 109.73, 96.99, 68.41, 60.35, 34.14, 28.78, 26.75, 25.65, 24.63, 14.26. IR (neat): 3461, 3341, 3251, 3215, 2987, 2946, 2873, 2360, 2219, 2208, 1728, 1630, 1587, 1549, 1521, 1482, 1448, 1415, 1357, 1335, 1273, 1235, 1211, 1187, 1166, 1145, 1108, 1028, 1013, 961, 946, 906, 871, 861, 828, 816, 805, 748.

6-{2-amino-6-[2-(4-cyano-5-dicyanomethylene-2,2-dimethyl-2,5-dihydro-furan-3-yl)-vinyl]-phenoxy}-hexanoic acid

JCW-03-020

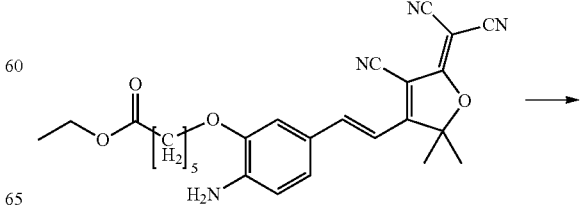

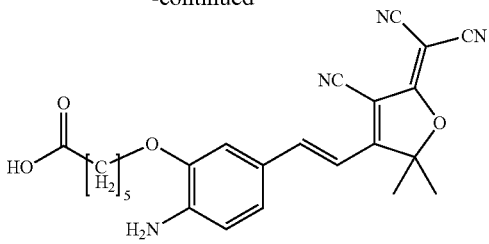

To a solution of 6-{2-amino-5-[2-(4-cyano-5-dicyanomethylene-2,2-dimethyl-2,5-dihydro-furan-3-yl)-vinyl]-phenoxy}-hexanoic acid ethyl ester (0.33 g, 0.71 mmol), in acetic acid (Sail) was added 5 mls of 6M HCl. The mixture was allowed to stir at room temperature for 16 hours. After being poured into 50 mls of water, it was neutralized with a solution of saturated sodium bicarbonate and extracted with ethyl acetate. Both phases of the separatory funnel remained highly colored so solid sodium chloride was added resulting in the decoloration of the aqueous layer. The organic phase was separated and dried over magnesium sulfate and rotovapped to dryness. Purification by column chromatography (60% EtOAc, 35% Hexane, 5% EtOH) provided 6-{2-amino-5-[2-(4-cyano-5-dicyanemethylene-2,2-dimethyl-2,5-dihydro-furan-3-yl)-vinyl]-phenoxy}-hexanoic acid as a shiny green solid (0.23 g, 74%). $^1$H NMR (400 MHz, CDCl$_3$) δ: 7.57 (d, 1H J=16.0 Hz), 7.17 (dd, 1H, J=8.4 Hz, J=1.6 Hz), 7.04 (d, 1H, J=1.6 Hz), 6.79 (d, 1H, J=16.0 Hz), 6.72 (d, 1H, J=8.4 Hz), 4.12 (t, 2H, J=7.2 Hz), 2.45 (t, 2H, J=6 Hz), 1.93 (m, 2H), 1.79 (m, 8H), 1.62 (m, 2H). $^{13}$C NMR (400 MHz, CDCl$_3$) δ: 176.65, 174.34, 174.17, 148.78, 146.49, 143.21, 127.15, 124.20, 113.86, 112.45, 112.36, 111.64, 111.13, 110.16, 109.82, 97, 35, 68.62, 33.27, 30.95, 29.72, 29.28, 28.75, 26.81

2-(5-carboxy-pentyloxy)-4-[2-(4-cyano-5-dicyanomethylene-2,2-dimethyl-2,5-dihydro-furan-3-yl)-vinyl]-benzenediazonium tetrafluoroborate

JCW-03-021

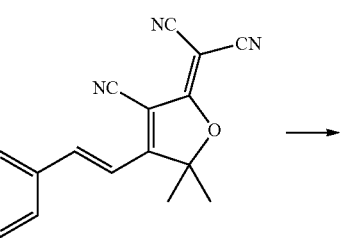

To a suspension of 6-{2-amino-5-[2-(4-cyano-5-dicyanomethylene-2,2-dimethyl-2,5-dihydro-furan-3-yl)-vinyl]-phenoxy}-hexanoic acid (0.30 g, 0.69 mmol) at 5° C. in 3.2 mls of fluoroboric acid (60%) was added a solution of sodium nitrite (0.29 g, 4.27 mmol) in 2 mls of water. The cooling bath was removed and the mixture was allowed to stir at room temperature for 2 hours. The resulting yellow solid, 2-(5-carboxy-pentyl oxy)-4-[2-(4-cyano-5-dicyanomethylene-2,2-dimethyl-2,5-dihydro-furan-3-yl)-vinyl]-benzenediazonium tetrafluoroborate, was removed by vacuum filtration and air dried (0.35 g, 97%). $^1$H NMR (400 MHz, DMSO) δ: 8.66 (d, 1H, J=8.4 Hz), 8.07 (s, 1H), 7.97 (d, 1H, J=9.2 Hz), 7.86 (d, 1H, J=16.4 Hz), 7.55 (d, 1H, J=16.4 Hz), 4.52 (t, 2H, J=6.4 Hz), 2.27 (t, 2H, J=7.2 Hz), 1.86 (m, 2H), 1.83 (s, 6H), 1.61 (m, 2H), 1.53 (m, 2H). IR (neat): 2360, 2341, 2264, 2230, 1730, 1586, 1481, 1307, 1106.

2-(5-ca boxy-pentyloxy)-4-[2-(4-cyano-6-dicyanomethylene-2,2-dimethyl-2,5-dihydro-furan-3-yl)-vinyl]-benzenediazonium; tetrafluoroborate

JCW-03-022

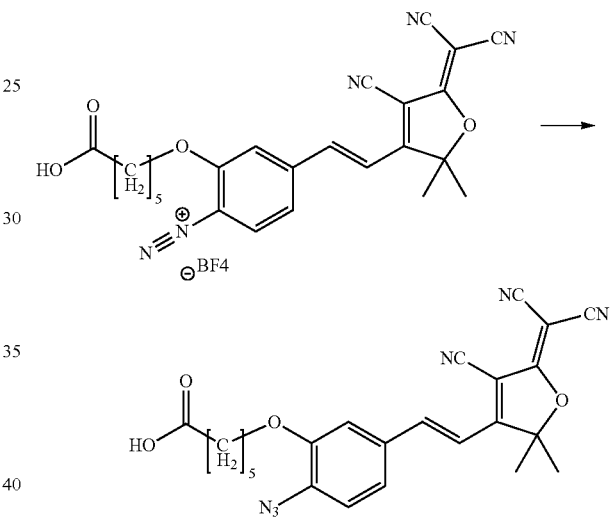

The following procedure requires dark room conditions. To a mixture of 2-(5-carboxy-pentyloxy)-4-[2-(4-cyano-5-dicyanomethylene-2,2-dimethyl-2,5-dihydro-furan-3-yl)-vinyl]-benzenediazonium; tetrafluoroborate (0.34 g, 0.64 mmol) in DMF (1.5 mls) was added a solution of azidotrimethylsilane (0.088 g, 0.76 mmol) in DMF (1.5 mls). After stirring for 2 hours at room temperature, the mixture was poured into 50 mls of water and extracted twice with ethyl acetate. The combined organic fractions were washed twice with water and dried over magnesium sulfate. Removal of the solvent under reduced pressure gave 0.260 g of a brown oil that was found to be the target azide contaminated with some DMF (based on examined by NMR). The material was purified by column chromatography (77% EtOAc, 4.5% EtOH, 18.5% Hexane) to give 6-{2-azido-5-[2-(4-cyano-5-dicyanomethylene-2,2-dimethyl-2,5-dihydro-furan-3-yl)-vinyl]-phenoxy}-hexanoic acid as a dark orange solid (0.200 g, 68%). $^1$H NMR (400 MHz, DMSO) δ: 7.60 (d, 1H, 16.4 Hz), 7.23 (dd, 1H, J=8.0 Hz, J=2.0 Hz), 7.11 (d, 1H, J=2.0 Hz), 7.03 (d, 1H, J=8 Hz), 6.97 (d, 1H, J=16.4 Hz), 4.13 (t, 2H), 2.43 (t, 2H, J=6.8 Hz), 1.93 (m, 2H), 1.82 (s, 6H), 1.76 (m, 2H), 1.63 (m, 2H). $^{13}$C NMR (400 MHz, DMSO) δ: 177.58, 175.53, 174.85, 152.39, 147.27, 132.70, 131.74, 113.19, 112.34, 111.31, 99.79, 99.48, 69.47, 68.73, 54.67, 34.05, 28.62, 25.64, 24.67. IR (neat): 2937, 2869, 2360, 2341, 2227, 2130, 2093, 1707, 1572, 1530, 1498, 1432, 1314, 1247, 1100, 971, 814.

6-{2-azido-5-[2-(4-cyano-5-dicyanomethylene-2,2-dimethyl-2,5-dihydro-furan-3-yl)-vinyl]-phenoxy}-hexanoic acid 2,5-dioxo-pyrrolidin-1-yl ester JCW-03-023, Formula 16

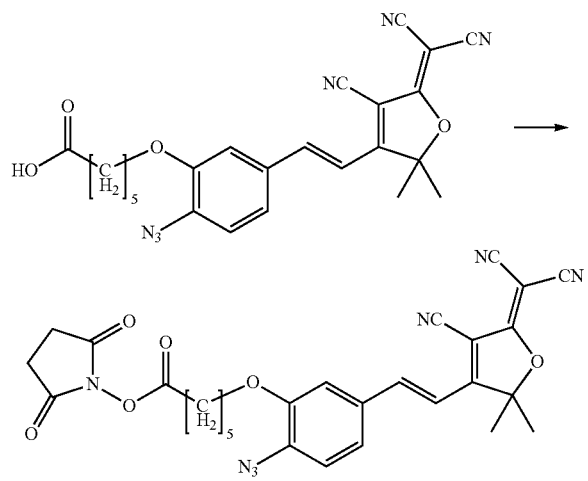

The following procedure requires dark room conditions. To a cooled solution (5° C.) of 6-{2-Azido-5-[2-(4-cyano-5-dicyanomethylene-2)-2-dimethyl-2,5-dihydro-furan-3-yl)-vinyl]-phenoxy}-hexanoic acid (0.1 g, 0.21 mmol) in dichloromethane (20 ml) was added N-hydroxysuccinimide (0.027 g, 0.24 mmol) and DOC (0.052 g, 0.25 mmol). The resulting solution was allowed to stir at 5° C. for 2 hours and then at room temperature for 12 hours. The solvent was removed under reduced pressure and the resulting dark red solid was purified by column chromatography (70% EtOAc/30% Hexane) to give 6-{2-azido-5-[2-(4-cyano-5-dicyanomethylene-2,2-dimethyl-2,5-dihydro-furan-3-yl)-vinyl]-phenoxy}-hexanoic acid 2,5-dioxo-pyrrolidin-4-yl ester as a dark red solid (0.084 g, 69%). $^1$H NMR (400 MHz, CDCl$_3$) δ: 7.60 (d, 1H, J=16.4 Hz), 7.24 (dd, 1H, J=8.4 Hz, J=1.6 Hz), 7.09 (d, 1H, J=1.6 Hz), 7.04 (d, 1H, J=8 Hz), 6.96 (d, 1H, J=16.4 Hz), 4.13 (t, 2H), 2.87 (s, br, 4H), 2.70 (t, 2H, J=7.2 Hz), 1.98 (m, 2H), 1.91 (m, 2H) 1.82 (s, 6H), 1.68 (m, 2H). $^{13}$C NMR (400 MHz, CDCl$_3$) δ: 173.50, 169.25, 168.48, 152.61, 146.50, 133.66, 131.19, 123.40, 121.54, 114.10, 112.07, 111.62, 110.83, 110.29, 97, 48, 69.18, 30.85, 29.71, 28.34, 26.55, 25.62, 25.22, 24.22. IR (neat): 3321, 2926, 2850, 2361, 2225, 2128, 2094, 1812, 1783, 1733, 1563, 1536, 1497, 1307, 1292, 1186, 1102, 1064, 1046, 849 cm$^{-1}$.

Synthesis in the DCM Class, i.e. Formula 12, with an Azide End Group

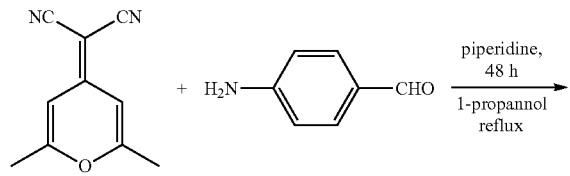

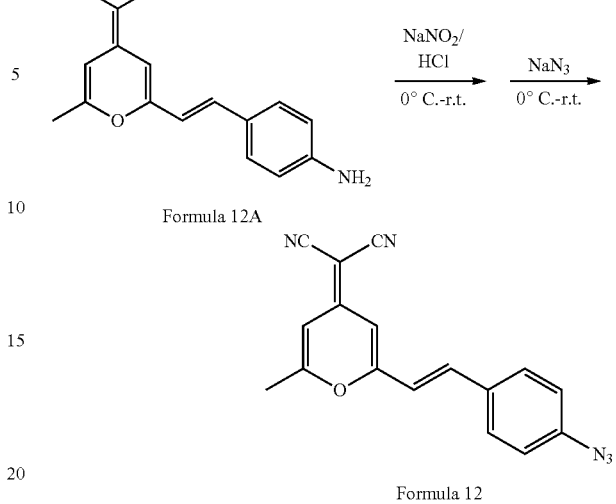

Formula 12A

Formula 12

Synthesis of 12A [(2-ethenyl-4-'aminophenyl)-6-methylpyran-4-ylidene]-malononitrile. A mixture of 2,6-dimethylpyran-4-ylidene-malononitrile (1.2 g, 6.8 mmol), 4-aminobenzaldehyde (1.0 g, 8.2 mmol) and piperidine (0.68 ml, 6.9 mmol) was dissolved in 150 ml 1-propanol and refluxed for 48 h. The reaction mixture was cooled, poured into water, stirred for 5 h and the precipitate was filtered and air-dried. The crude product was further purified by silica gel column chromatography using hexane/EAC 30-50% as eluent. The product was finally recrystallized from dichloromethane/1-propanol. Yield: 1.50 g (80%); mp: 249° C.; λ$_{max}$=436 nm; $^1$H NMR (400 MHz, DMSO) δ 7.36 (d, J=8.4 Hz, 2H), 7.31 (s, 1H), 6.91 (d, J=16 Hz, 1H), 6.69 (s, 1H), 6.57 (d, J=16 Hz, 1H), 6.55 (d. J=8.4 Hz, 2H), 5.86 (s, 2H), 2.40 (s, 3H); $^{13}$C NMR (DMSO) 163.12, 160.71, 156.05, 151.12, 138.47, 129.61, 121.57, 115.31, 113.18, 111.53, 104.88, 104.22, 18.80. IR (neat, cm$^{-1}$) 3478, 2957, 2200, 1647.

Synthesis of Formula 12, [(2-ethenyl-4-'azidophenyl)-6-methylpyran-4-ylidene]-malononitrile. A solution of NaNO$_2$ (552 mg, 8.0 mmol)) in 8 mL water was added dropwise to a solution of the [(2-ethenyl-4-'aminophenyl)-6-methylpyran-4-ylidene]-malononitrile (1.10 g, 4.0 mmol) in 46 ml 4M HCl at 0-5° C. After stirring the mixture at this temperature for 45 min, a solution of NaN$_3$ (520 mg, 8.0 mmol) in 8 ml water was slowly added to the mixture at the same temperature. Stirring was continued for 1 h below 5° C. and then for overnight at room temperature. The precipitate was filtered and air-dried. The product was further purified by a silica gel column chromatography using hexane/EAC (7:3) as eluent and filially recrystallized from dichloromethane/1-propanol. Yield: 550 mg (45%); mp: 190° C.; λ$_{max}$(CH$_2$Cl$_2$)=405 nm.

Figure 9:
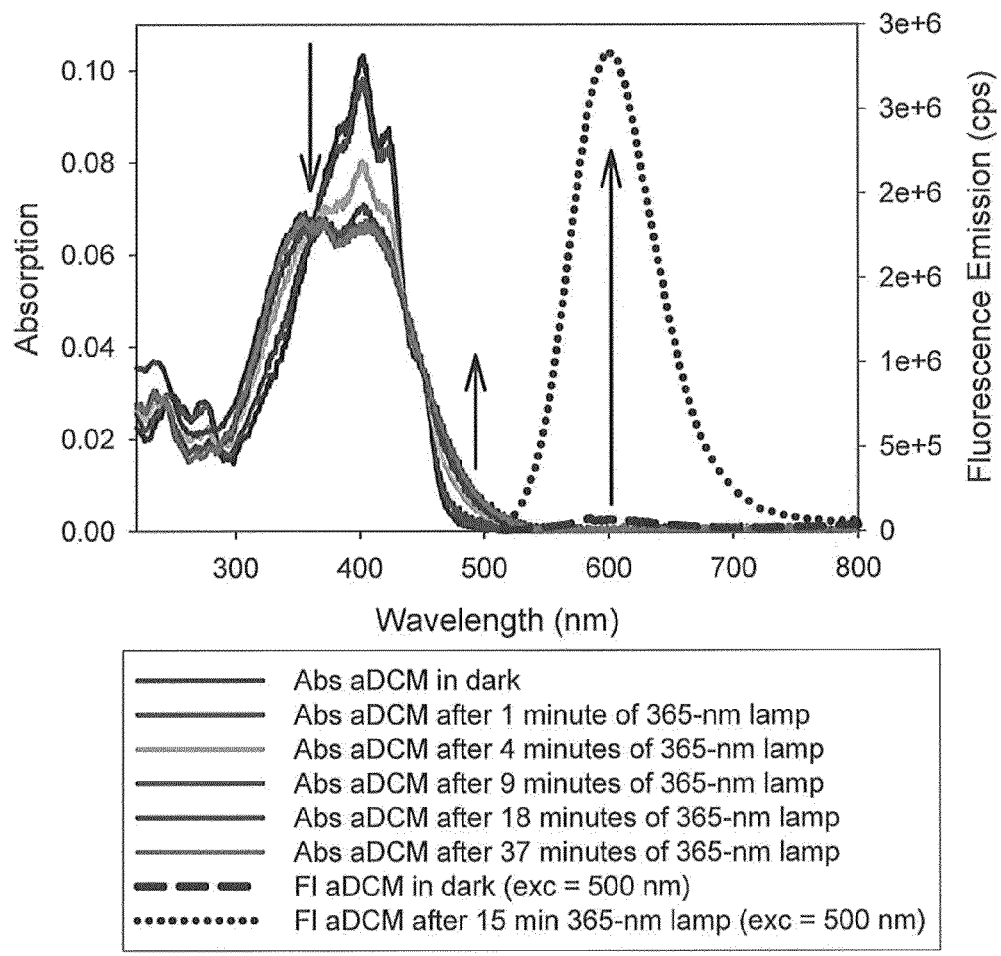
FIG. 9 is a photoconversion of DCM-azide to DCM-amine. The DCM-azide ("aDCM") is hardly fluorescent while the DCM-amine has strong fluorescence.

The DCM azide is dissolved in ethanol and the spectra prior to irradiation is shown in FIG. 9 Irradiation of this sample with a 365-nm source, for example, brings about consumption of the azide and appearance of the photoproduct amine shoulder with λmax>450 nm (shown at one-, four-, nine-, 18- and 37-minute intervals). The fluorescence of the DCM azide and photoproduct DCM amine are also shown. Excitation of the DCM azide at 500 nm produces very little fluorescence. In contrast, the excitation of photoproduct DCM amine at 500 nm produces strong fluorescence with λmax 600 nm.

Synthesis of NBD azide, Formula 13 with azide substitution. In a 50-mL round bottom flask equipped with a stirbar, 7-chloro-4-nitrobenzofurazan (1.5 g, 7.52 mmol) and sodium azide (0.54 g, 8.27 mmol) were stirred in ethanol (15 mL) for 6 h at 35° C. TLC indicated complete consumption of the starting material. The solution was poured into ice water, forming a precipitate, which was filtered and washed with water. The product was collected as a yellow powder in the amount of 1.45 g (94% yield). mp 101.1-101.9° C. $^1$H NMR (400 MHz, CDCl$_3$) δ 8.53 (d, J=8.2 Hz, 1H), 7.08 (d, J=8.2 Hz, 1H). $^{13}$C NMR (100 MHz, CDCl$_3$) δ 145.9, 143.6, 138.1, 132.2, 128.6, 114.9. $\lambda_{max}^{CH2Cl2}$ 388 nm (ε 1.44×. 10$^4$). IR $v_{max}$ (cm$^{-1}$) 2114 (N$_3$).

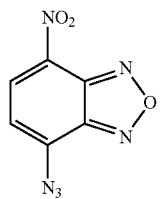

Formula 13

7-Azido-4-nitrobenzoxadiazole

Figure 10:
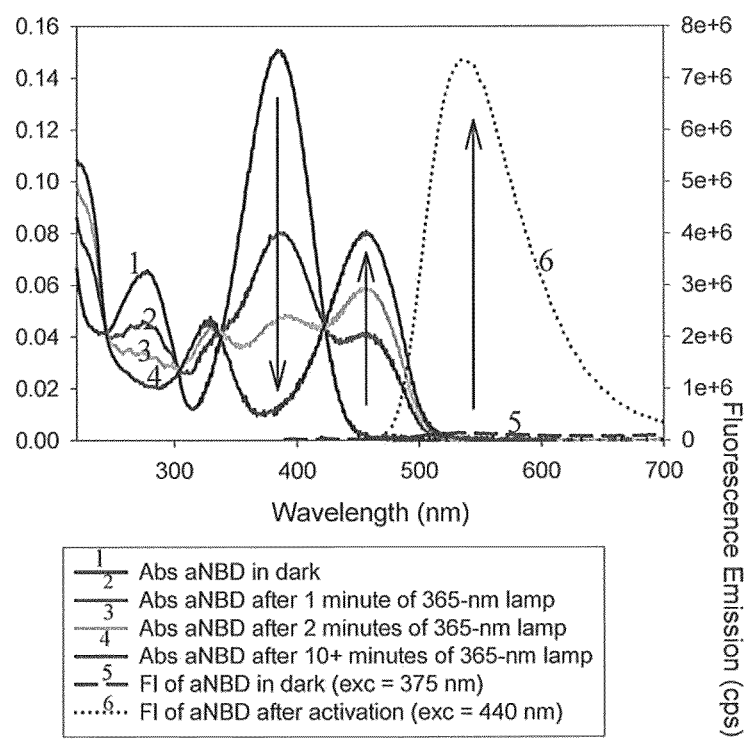
FIG. 10 is a Photoconversion of NBD-azide to NBD-amine. The NBD-azide ("aNBD") is hardly fluorescent while the NBD-amine has strong fluorescence.

While the NBD azide and any amines derived from it will both have relatively short absorption and emission wavelengths compared to the DCDHF or DCM dyes, the NBD system will still have useful applications because NBD labels are currently used for imaging of membranes, for example. An experiment showing photoconversion of NBD-azide to NBD amine is shown in FIG. 10. Here NBD azide is dissolved in ethanol and the spectra prior to irradiation with λmax 385 nm is shown, Irradiation of this sample with a 365-nm source, for example, brings about consumption of the azide and appearance of the photoproduct amine with λmax 460 nm (shown at one-, two-, and ten-minute intervals). The fluorescence of the NBD azide and photoproduct NBD amine are also shown. Excitation of the NBD azide at 375 nm produces very little fluorescence. In contrast the excitation of photoproduct NBD amine at 440 nm produces strong fluorescence with λmax 560 nm. In this case it would be possible to excite the amine at wavelengths above about 470 nm and generate fluorescence with little or no further conversion of NBD azide to NBD amine.

Synthesis of 4-(2-pyridin-4-yl-vinyl)-phenylamine (4'-amino-4-stilbazole) with an azide end group (Formula 14). To an oven-dried flask charged with nitrogen was added 4-iodoaniline (5.59 g, 25.5 mmol), 4-vinylpyridine (3.68 g, 35 mmol), palladium (II) acetate (14.4 mg, 0.064 mmol), tri-o-tolylphosphine (39.0 mg, 0.128 mmol), triethylamine (7.08 g, 70 mmol), and acetonitrile (25 mL). The flask was fitted with a reflux condenser and then charged again with nitrogen. A bubbler was quickly attached to the top of the condenser and then the flask was heated in an oil bath. The mixture was stirred at reflux for 48 h, after which the flask was cooled to room temperature. The mixture was poured into cold water and then the precipitate was collected via vacuum filtration. The product was placed in the vacuum oven and dried overnight at 55° C. at approximately 20 mmHg vacuum until it reached a constant mass. The product was collected as a yellow powder in the amount of 4.26 g (85% yield), mp 270.1-276.4° C. $^1$H NMR (400 MHz, DMSO-d$_6$) δ 8.45 (dd, J=1.6, 6.1 Hz, 2H), 7.44 (dd, J=1.6, 6.1 Hz, 2H), δ 7.37-7.32 (m, 3H), 6.87 (d, J=16.4 Hz, 1H), 6.58 (ddd, J=1.9, 2.6, 8.6 Hz, 2H), 5.49 (s, 2H). $^{13}$C NMR (100 MHz, DMSO-d$_6$) δ 150.3, 145.7, 134.2, 129.0, 124.1, 120.6, 120.3, 114.2. $\lambda_{max}$ CH$_3$CN 348 nm 2.96×10$^4$).

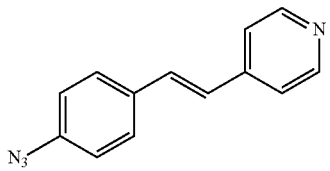

Formula 14A

Synthesis of 4-[2-(4-azido-phenyl)-vinyl]-pyridine (4-azido-4-stilbazole) (Formula 14S). A solution of sodium nitrite (1.76 g, 25.5 mmol) in 10 mL water was added dropwise to a solution of 4-(2-pyridin-4-yl-vinyl)-phenylamine (2.0 g, 10.2 mmol) in 102 mL 4M HCl at 2-3° C. After stirring the mixture at this temperature for 1 hr, a solution of sodium azide (1.32 g, 20.4 mmol) in 10 mL water was slowly added dropwise, maintaining the temperature at 2-3° C. Stirring was continued for 30 min at this temperature and then the ice bath was allowed to come to ambient temperature while stirring continued overnight Saturated aqueous sodium bicarbonate was added carefully to this mixture with stirring until the evolution of gas subsided. The precipitate was filtered off and dried overnight in the funnel to yield 1.875 g of the product as a beige powder (83% yield), mp 88.2-89.4° C. $^1$H NMR (400 MHz, CDCl$_3$) δ 8.51 (dd, J=1.4, 6.1 Hz, 2H), 7.46 (ddd, J=1.9, 21, 8.5 Hz, 2H), 7.29 (dd, J=1.4, 6.1 Hz, 2H), 7.18 (d, J=16.4 Hz, 1H), 6.98 (ddd, J=2.0, 2.7, 8.5 Hz, 2H), 8.90 (d, J=16.4 Hz, 1H). $^{13}$C NMR (100 MHz, CDCl$_3$) δ 150.3, 144.4, 140.3, 133.1, 132.0, 128.4, 125.7, 120.8, 119.5. $\lambda_{max}^{CH3CN}$ 323 nm (ε 3.92×10$^4$). IR $v_{max}$ (cm$^{-1}$) 2122 (N$_3$).

Synthesis of 4-[2-(4-azido-phenyl)-vinyl]-1-methyl-pyridinium iodide (4'-azido-4-stilbazolium methiodide) (Formula 14 with R=CH$_3$ and X=I). In a 100 mL round bottom flask equipped with a stirbar and covered with foil, 4-[2-(4-azido-phenyl)-vinyl]-pyridine (0.57 g, 2.56 mmol) was mixed with iodomethane (0.95 g, 6.7 mmol) in acetonitrile (20 mL) and stirred at room temperature for 36 hrs. A precipitate had formed and TLC showed a single spot, so the solution was placed in the refrigerator for 30 minutes and then filtered, rinsing with diethyl ether. The product was collected as a yellow powder (0.482 g). Diethyl ether was added to the filtrates and then placed in the refrigerator for 2 his. Orange/brown crystals formed which were collected by suction filtration (0.15 g). The total amount of product collected was 0.63 g (68% yield). mp 166.2-168.0° C. $^1$H NMR (400 MHz, DMSO-d$_6$) δ 8.86 (d, J=6.9 Hz, 2H), 8.20 (d, J=6.9 Hz, 2H), 8.01 (d, J=16.4 Hz, 1H), 7.80 (ddd, J=1.8, 2.6, 8.5 Hz, 2H), 7.49 (d, J=16.4 Hz, 1H), 7.26 (ddd, J=1.8, 2.6, 8.5 Hz, 2H), 4.26 (s, 3H). $^{13}$C NMR (100 MHz, DMSO-d$_6$) 152.89, 145.56, 141.80, 140.08, 132.54, 130.31, 123.90, 123.28, 120.37, 47.39. $\lambda_{max}^{CH3CN}$ 373 nm (ε 4.07×10$^4$). IR $v_{max}$ (cm$^{-1}$) 2118 (N$_3$).

The following paragraphs generally relate to photo-physical parameters of various azide-pi-acceptor fluorogens, and to the preparation, examples, data tables, graphs, etc., with regard to fluorophores derived from azide-pi-acceptor compounds photochemically converted to amine-pi-acceptor fluorophores.

Figure 11:
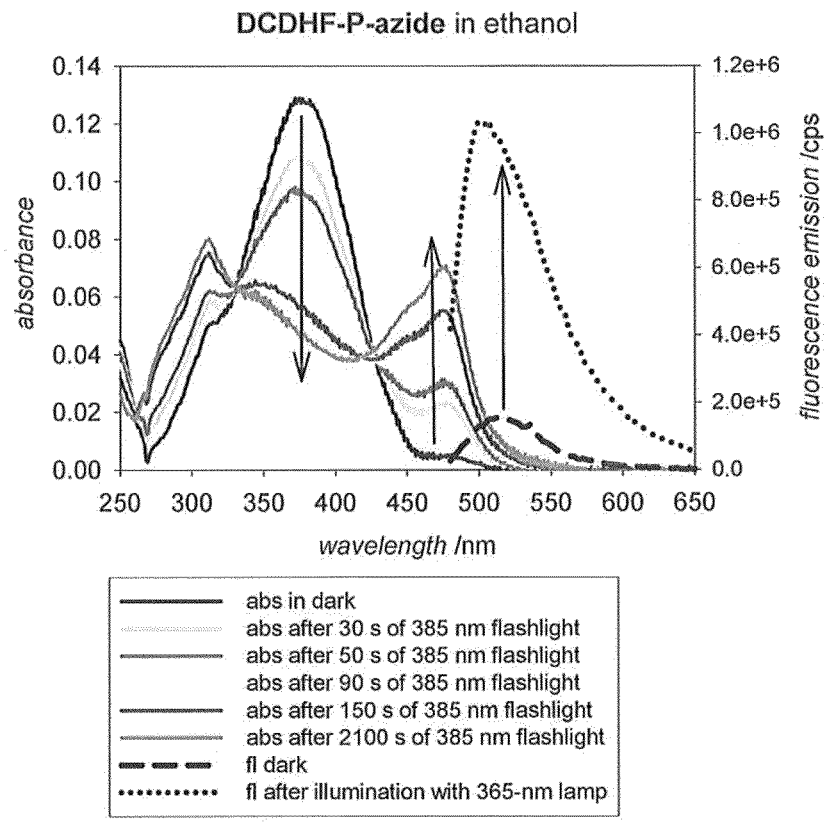
FIG. 11 is a graph illustrating the absorbance and fluorescence emission of DCDHF-V-P-azide in ethanol.
Figure 12:
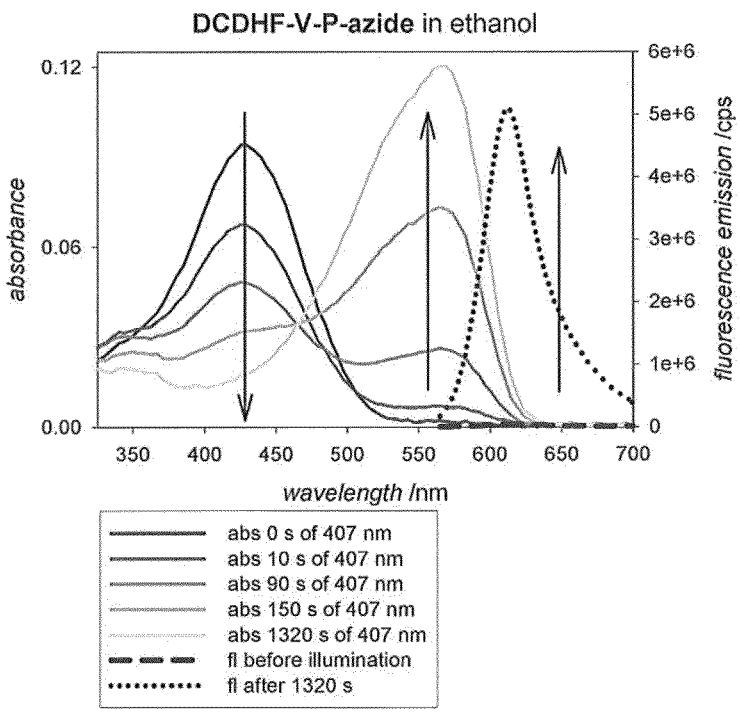
FIG. 12 is a graph illustrating the absorbance and fluorescence emission of DCDHF-V-P-azide in ethanol.
Figure 13:
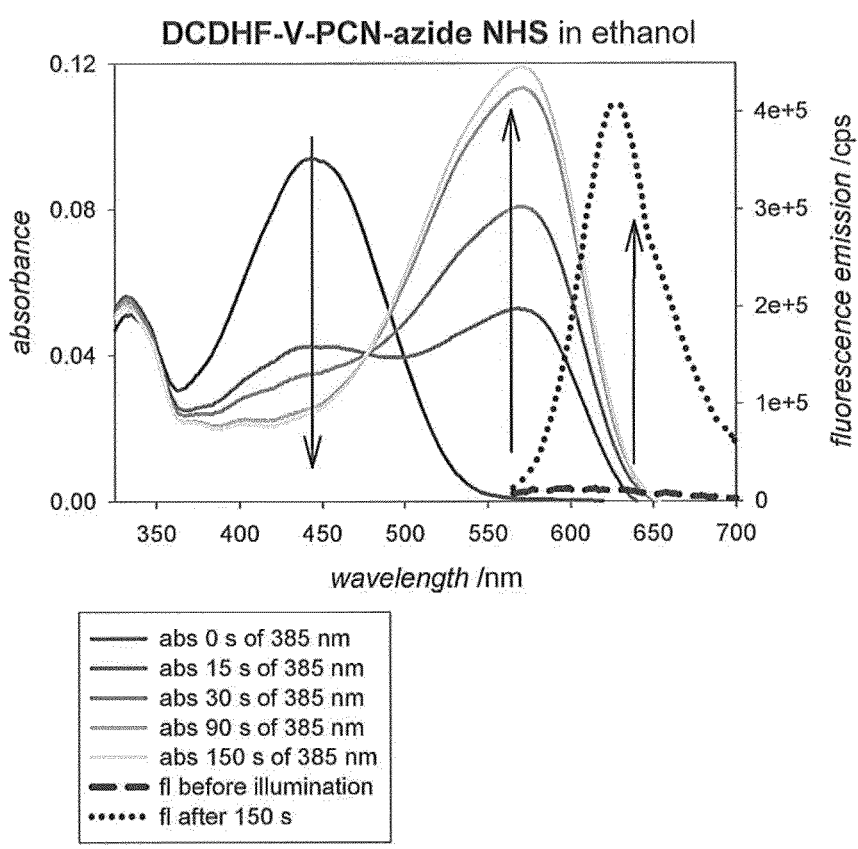
FIG. 13 is a graph illustrating the absorbance and fluorescence emission of DCDHF-V-PCN-azide NHS in ethanol.
Figure 14:
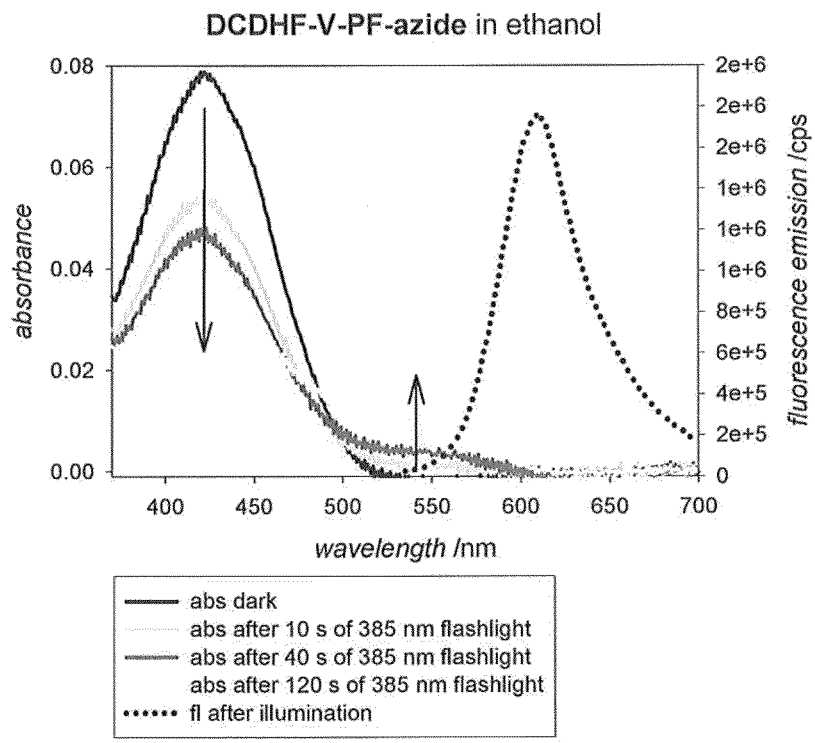
FIG. 14 is a graph illustrating the absorbance and fluorescence emission of DCDHF-V-PF-azide in ethanol.
Figure 15:
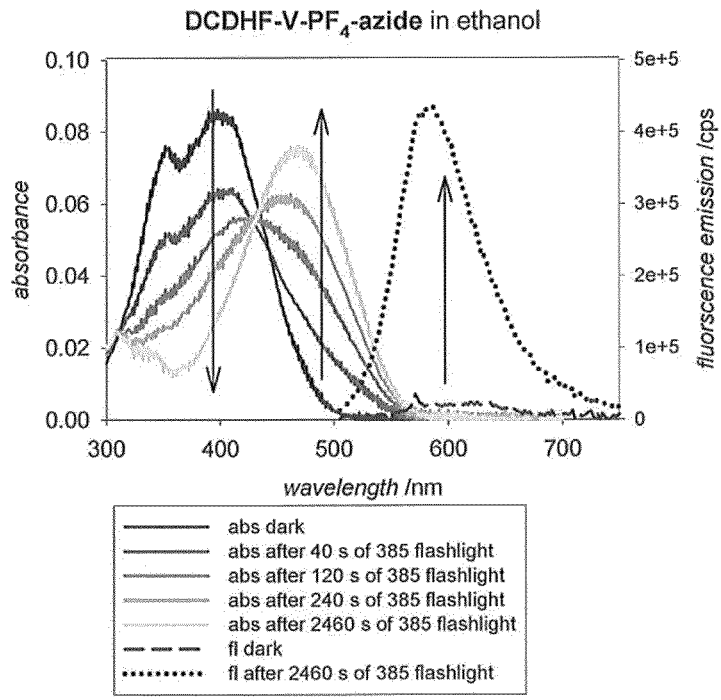
FIG. 15 is a graph illustrating the absorbance and fluorescence emission of DCDHF-V-PF$_4$-azide in ethanol.
Figure 16:
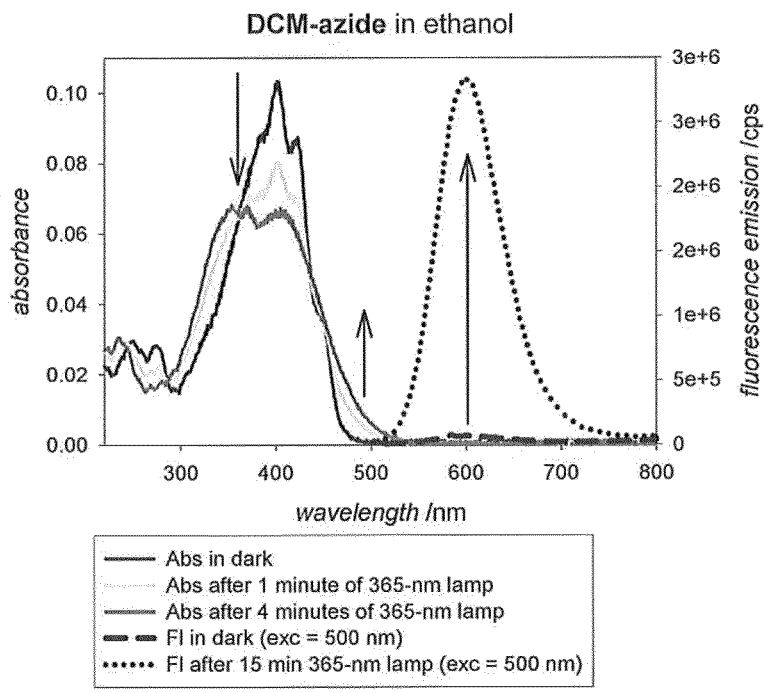
FIG. 16 is a graph illustrating the absorbance and fluorescence emission of DCM-azide in ethanol.
Figure 17:
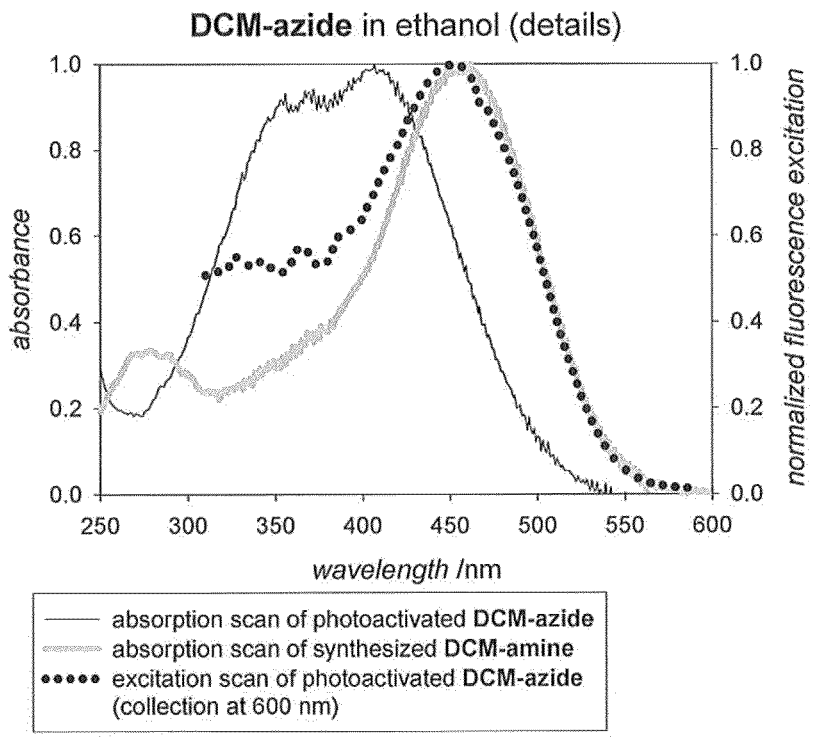
FIG. 17 is a graph illustrating the absorbance and normalized fluorescence excitation of DCM-azide in ethanol. Spectra of DCM-azde and synthesized DCM-amine corroborate that the fluorescing species in the photoreaction mixture is the DCM-azide.

| | $\lambda_{abs,azido}$ (nm)[a] {$\epsilon_{max}$ (M$^{-1}$ cm$^{-1}$)} | $\lambda_{abs,amino}$ (nm)[b] {$\epsilon_{max}$ (M$^{-1}$ cm$^{-1}$)} | $\lambda_{fl,amino}$[c] (nm) | yield[d] | $\phi_F$[e] | $\phi_P$[f] {$\lambda_P$}[g] | $\phi_B(10^{-6})$[h] in PVA |
|---|---|---|---|---|---|---|---|
| 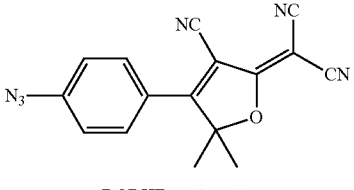<br>DCDHF—P-azide | 379 (19,300)[i] | 475 (44,900)[i] | 496 | 24% | 0.003 | ~0.08 (385 nm) | 4.6 (see FIG. 11) |
| 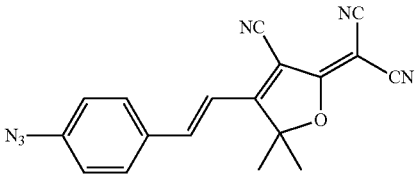<br>DCDHF—V—P-azide | 424 (29,100) | 570 (54,100) | 613 | 65% | 0.225 | 0.0059 (407 nM) | 4.1[k] (see FIG. 12) |
| 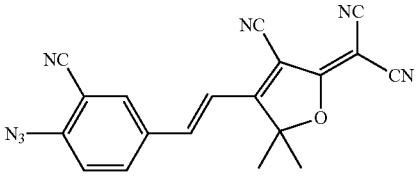<br>DCDHF—V—PCN-azide | 415 (19,100) | 479 | 591 | ~50% | | ~0.09 (385 nm) | (see FIG. 13) |
| 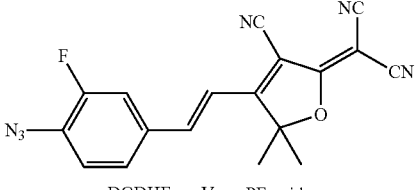<br>DCDHF—V—PF-azide | 420 (18,100)[i] | 517 | 611 | | | | 3.4 (see FIG. 14) |
| 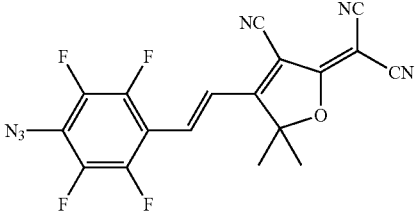<br>DCDHF—V—PF$_4$-azide | 407 (26,700) | 463 (20,000) | 578 | 87% | 0.0062 | 0.017 (385 nm) | 9.2 (see FIG. 15) |
| 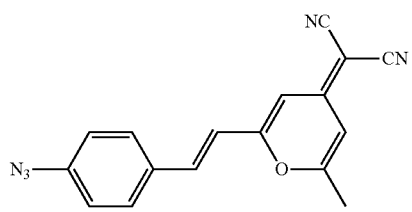<br>DCM-azide | 403 (31,300) | 456 (31,100) | 599 | <30% | 0.18 | 0.085 (385 nm) | 6.2 (see FIG. 16 & 17) |

-continued

Figure 18:
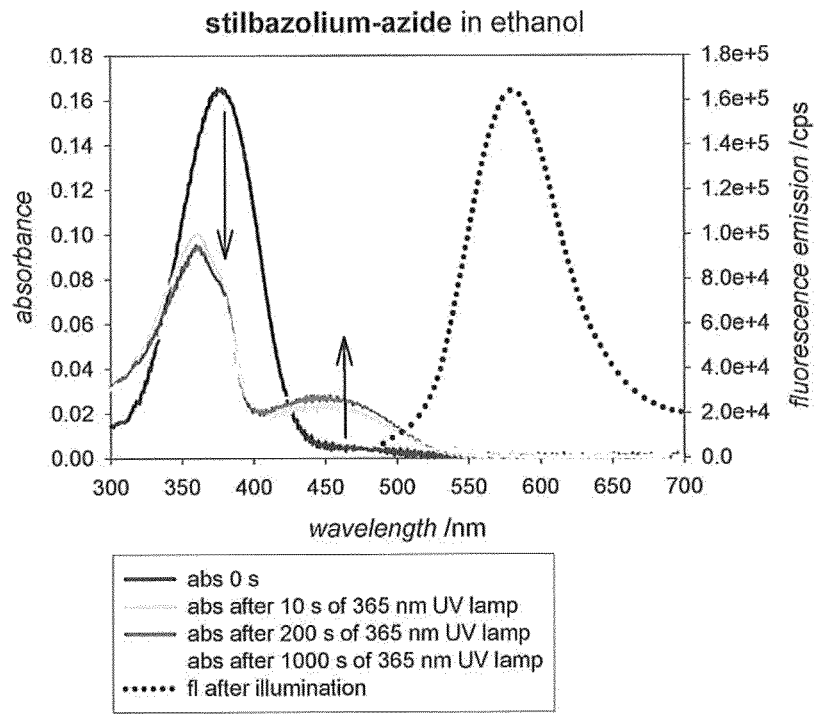
FIG. 18 is a graph illustrating the absorbance and wavelength of stilbazolium-azide in ethanol.
Figure 19:
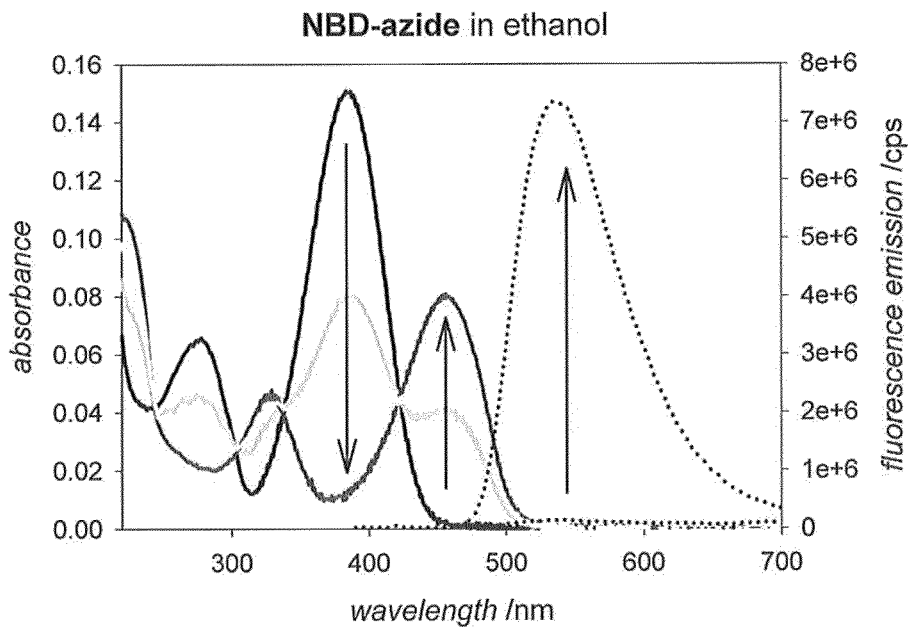
FIG. 19 is a graph illustrating the absorbance and wavelength of NBD azide in ethanol.

| | $\lambda_{abs,azido}$ (nm)[a] {$\epsilon_{max}$ (M$^{-1}$ cm$^{-1}$)} | $\lambda_{abs,amino}$ (nm)[b] {$\epsilon_{max}$ (M$^{-1}$ cm$^{-1}$)} | $\lambda_{fl,amino}$[c] (nm) | yield[d] | $\phi_F$[e] | $\phi_P$[f] {$\lambda_P$}[g] | $\phi_B(10^{-6})$[h] in PVA |
|---|---|---|---|---|---|---|---|
| 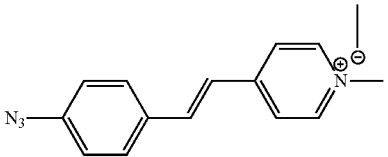 stilbazolium-azide | 375 (41,000)[i] | 449 | 580 | ~25% | | ~0.2 (365 nm) | (see FIG. 18) |
| 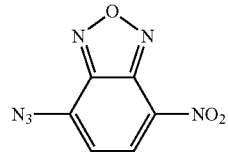 NBD-azide | 384 (14,400)[i] | 456 | 539 | ~50% | 0.20 | ~0.2 (365 nm) | 100[i] (see FIG. 19) |

[a]The absorbance peak and molar absorption coefficient for the azido fluorogen.
[b]The absorbance peak and molar absorption coefficient of the photoactivated amino fluorophore.
[c]The fluorescence emission peak of the photoactivated amino fluorophore.
[d]Overall chemical reaction yield (azido fluorogen → amino fluorophore) measured from photoactivation spectra (FIGURE 1 and SI). Approximate values are calculated using molar absorption coefficient from solvents other than ethanol.
[e]The fluorescence quantum yield of the photoactivated amino fluorophore. DCDHFs become much brighter in rigid environments
[f]The quantum yield of photoconversion of the azido fluorogens to any product (see SI). Approximate values are calculated using molar absorption coefficient from solvents other than ethanol.
[g]The wavelength used to photoactivate the azido fluorogens: 365-nm source is a handheld Hg UV lamp (0.62 mW cm$^{-2}$); 385 nm source is a LED flashlight (1.1 mW cm$^{-2}$, see SI for spectrum); 407-nm source is a Kr-ion laser (3.1 mW cm$^{-2}$).
[h]The photobleaching quantum yield of the amino fluorophores (see SI). For comparison, the value for fluorescein in gelatin is 64 × 10$^{-6}$. The standard errors are typically less than 10%.
[i]In dichloromethane.
[j]In acetonitrile.
[k]In gelatin.
[l]In PMMA.

Scheme.
By P-ATA, photoconversion of dark azido push-pull fluorogens produce fluorescent amino molecules.

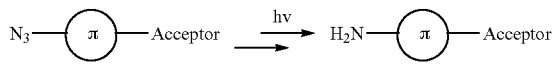

For spectra of azido push-pull fluorogens see FIGS. 11 through 19.

Thermal Conversion of a Fluorogen to Fluorophore via an Alkene or Strained Alkene (T-ATA)

Another important aspect of the present invention is that it was surprisingly found that fluorogens such as an azide-pi-acceptor compound when reacted with an alkene or a strained alkene yield a fluorophore that absorbs (i.e. can be excited by) visible light. The acceptors generally include the acceptors set forth hereinabove with respect to the photoactivation route as well as specific acceptors set forth in Formulas 1 through 8, all of which are hereby fully incorporated by reference. The pi compounds of the fluorogen include the pi compounds set forth hereinabove with regard to the photoactivation route and the same is fully incorporated by reference including the various pi compounds set forth in Formulas 11 through 19. The chemically created fluorophores set forth herein are highly fluorescent and generally contain a heterocyclic nitrogen group such as a dihydrotriazole, or an amine group, (e.g. secondary) but the product identity is influenced by the nature of the specific reactants and conditions as set forth hereinbelow.

The general reaction conditions for the photochemical and thermal reactions are as follows. Acceptable temperatures can range from about 0° C. to about 65° C. with desirably temperatures ranging from about 10° C. to about 45° C. and suitable temperatures including room temperature as from about 15° C. to 30° C. and more preferably from about 20° C. to about 25° C. Biological reaction temperatures can occur at higher temperatures, for example up to about 40° C. or to a temperature at which the molecule will not degrade. Suitable solvents include water, an alcohol containing from 2 to about 10 carbon atoms such as ethanol or methanol, or other protic solvents, as well as other solvents known to the art and to the literature. The thermal reaction between the azido fluorogen and a norbornene or other strained alkene or alkyne does not generally require a catalyst. The amounts of reactants are dependent on the application. For the thermal reactions, higher concentrations of reactants will accelerate the reaction; the two reactants can be used in equal relative amounts, with more of the azide molecules, or more of the alkyne or alkene molecules.

While simple alkenes can be utilized, they are not preferred. Simple alkenes include 1-butene, cyclohexane, 2-butene, and the like. Simple alkenes undergo cycloaddition with azides at temperatures that may not be compatible with biological systems. However, strained alkenes do react with azides at temperatures compatible with biological systems.

Strained or activated alkenes are preferred and generally are defined as cycloalkenes having a total of from about 3 to about 40 carbon atoms, desirably from about 3 to about 15 carbon atoms with from about 7 to about 12 carbon atoms being preferred and including one or more heteroatoms either within the ring or attached to the ring wherein the heteroatom can be an oxygen, a nitrogen, and the like. An example of such preferred strained compounds include the so-called bridge alkenes such as bridged bicyclic alkenes with norbornene being a preferred example thereof. The following paragraphs generally set forth desirable examples of such strained alkenes.

With regard to the rate of cycloaddition (1,3-dipolar cycloaddition between alkene azide, also known as a [2+3] cycloaddition) producing a dihydrotriazole is influenced by a variety of factors. For the azide component the main influence is electronic and depends on the properties of the single group attached to the azide and to a lesser extent any steric issues associated with this substituent. For the alkene component the influences are more complicated due, in part, to the presence of up to four unique sites of substitution on the alkene. Electronic contributions from substituents on the alkene influence the cycloaddition rate along with olefin geometry and steric issues associated with the alkene. Some of these same factors also influence the ability of the dihydrotriazole to function as a donor in a donor-pi-acceptor system (should the dihydrotriazole adduct prove to be sufficiently stable).

Some of the same factors that influence the initial cycloaddition producing the 4,5-dihydrotriazole also influence the stability of the 4,5-dihydrotriazole and the rate and outcome of any subsequent rearrangements of this dihydrotriazole including any rearrangement with concomitant loss of nitrogen producing an amine (secondary amine and/or aziridine) or imine. Patterns of reactivity are described in some detail here: R. Huisgen, R, Grashey, J. Sauer, "Chemistry of Alkenes", Interscience, New York, 1964, 806-877.

For practical use in biolabeling the azide alkene cycloaddition reaction must proceed at a useful rate under ambient conditions. In order to enhance the reaction rate we have chosen strain relief as a driving force in these reactions. Many alkene candidates are known but we have used readily available and highly reactive norbornene as the strained alkene (other factors also contribute to the high reactivity of this alkene as seen in, R. Huisgen, et. al., "Exceptional Reactivity of the Bicyclo[2.2.1]heptene Double Bond", J. Amer. Chem. Soc., 120, pp 3951-3953 (1980)). Other options for strained systems including alkenes are found by reference here: J. March, Advanced Organic Chemistry Reactions, Mechanisms, and Structure, 4$^{th}$ edition, John Wiley & Sons, 1992, pp. 150-164. Introduction of strain into an alkene is accomplished by one or more distortions of the bonds between the alkene carbons and their substituent atoms involving bond length changes, bond angle changes, deviation from planarity and torsional changes. These distortions often result from inclusion of the alkene in a ring (a cis-alkene in small rings or a trans-alkene in some medium rings) or at a bridgehead position found in polycyclic systems. Reactions of picryl aide with a range of alkene containing molecules illustrate the influence on cycloaddition rates and product structure distribution, K. J. Shea and J.-S. Kim, "Influence of Strain on Chemical Reactivity, Relative Reactivity of Torsionally Strained Double Bonds in 1,3-Dipolar Cycloadditions", J. Amer. Chem. Soc., 114, 4846-4855 (1992). Some specific alkene examples are provided but are not limited to hydrocarbon examples; cyclopropene, cyclobutene, bicyclo[2.1.0]pent-2-ene, bicyclo[2.2.1]hept-2-ene (norbornene), bicyclo[2.2.1]hepta-2,5-diene (norbornadiene), exo-tricyclo[3.2.1.0$^{2,4}$]oct-6-ene, endo-tricyclo-[3.2.1.0$^{2,4}$]oct-6-ene, endo-tricyclo[4.3.0.1$^{2,5}$]deca-3,7-diene, trans-cyclooctene, bicyclo[3.3.1]non-1-ene; examples with additional heteroatom substituents and/or heteroatoms in rings; anti-sesquinorbornene endo-anhydride, (+/-)-bicyclo[2.2.1]hept-5-en-2-one, 2-norbornen-7-one ethylene acetal, 7-oxabicyclo[2.2.1]hept-2-ene, diethyl 2,3-diazabicyclo[2.2.1]hept-5-ene-2,3-dicarboxylate, 2-norbornen-7-one ethylene acetal.

The additional functional groups on the alkene-containing molecules are useful as sites for introduction of additional reactive functional groups, for example norborn-5-en-2-ylacetic acid or norbornenyl-1-acetic acid converted to their respective hydroxy succinimide esters.

The following paragraphs generally relate to photo-physical parameters of various azide-pi-acceptor fluorogens, and to the preparation, examples, data tables, graphs, etc., with regard to fluorophores derived from azide-pi-acceptor compounds thermally reacted with alkenes or strained alkenes.

Figure 20:
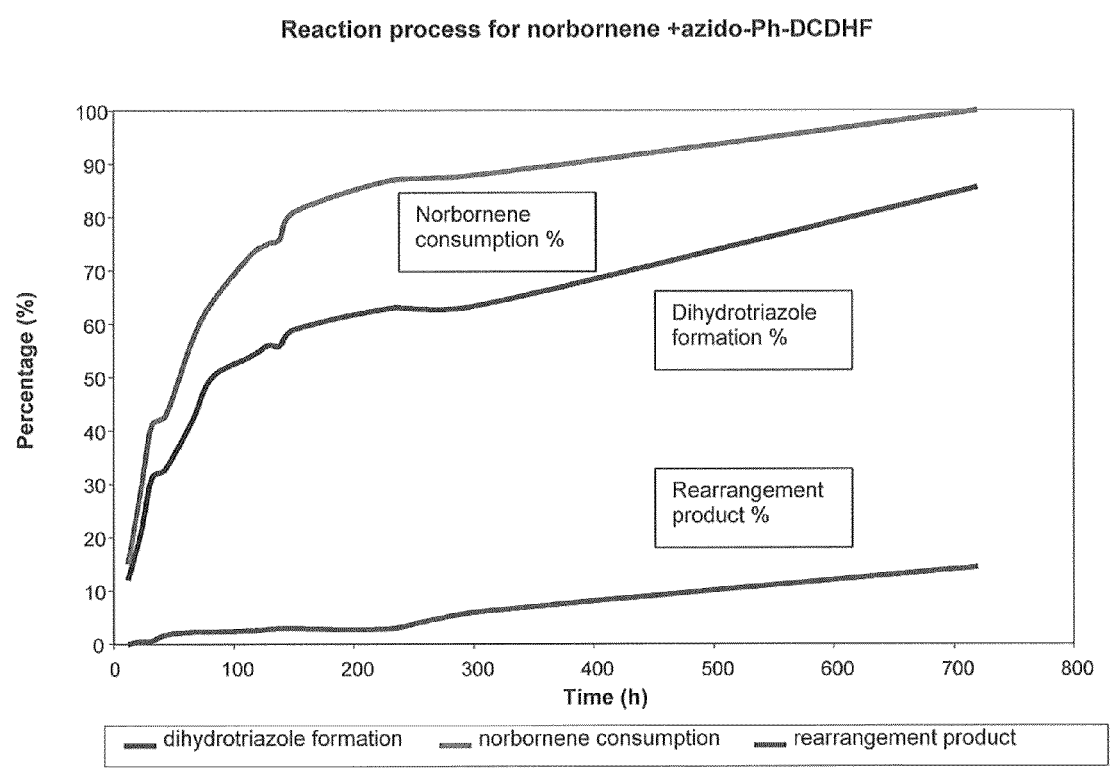
FIG. 20 is a graph illustrating the reaction process for norbornene+azide-Ph-DCDEHF monitored by NMR spectrum.

Reaction between azido DCDHF and norbornene in deuterochloroform was followed by NMR. As seen in FIG. 20, the reaction rate was very low and the dihydrotriazole intermediate could be observed in addition to the final rearranged amine product. In this case, cycloaddition to give the dihydrotriazole appears to be significantly faster than the loss of nitrogen and rearrangement to give the amine.

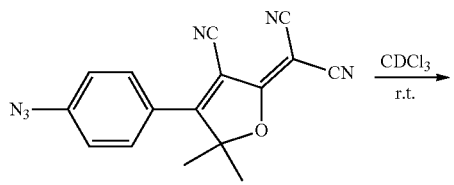

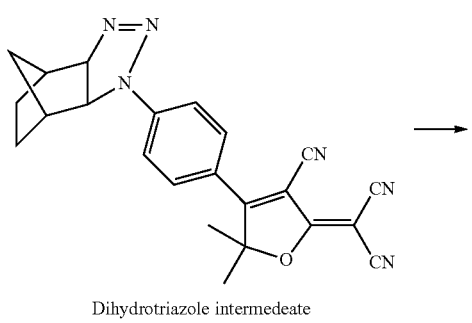

Dihydrotriazole intermedeate

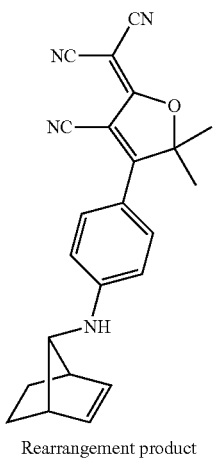

Rearrangement product

The FIG. 20 reaction conditions, amount of dihydrotriazode formation and norbornene consumption are set forth in the following table.

| Time Period | Reaction condition | Dihydrotriazole formation % | Norbornene consumption % | Rerrange- ment ratio[a] |
|---|---|---|---|---|
| 0-12 h (12 h) | Standing at r.t. without spinning | 12% | 15% | 0% |
| 12-23 h (11 h) | Standing at r.t. without spinning | 21% | 29% | 0.50% |
| 23-32 h (9 h) | Spinning in NMR at r.t. | 31% | 41% | 0.55% |
| 32-44 h (12 h) | Standing at r.t. without spinning | 33% | 43% | 1.75% |
| 44-68 h (22 h) | Standing at r.t. without spinning | 42% | 57% | 2.3% |
| 68-84 h (16 h) | Spinning in NMR at r.t. | 50% | 64% | 2.3% |
| 84-117 h (33 h) | Standing at r.t. without spinning | 54% | 73% | 1.7% |
| 117-131 h (14 h) | Spinning in NMR at r.t | 56% | 75% | 2.8% |
| 131-141 h (10 h) | Standing at r.t. without spinning | 58% | 76% | 2.9% |
| 141-153 h (12 h) | Spinning in NMR at r.t. | 59% | 81% | 1.5% |
| 153-235 h (82 h) | Standing at r.t. without spinning | 63% | 87% | 2.9% |
| 235-307 h (72 h) | Standing at r.t. without spinning | 63.5% | 88% | 6.0% |
| After 1 month | Standing at r.t. without spinning | 100% | — | 14.4% |

[a]ratio = rearrangement product/(didhydrotriazole + azido-P-DCDHF)

Figure 21:
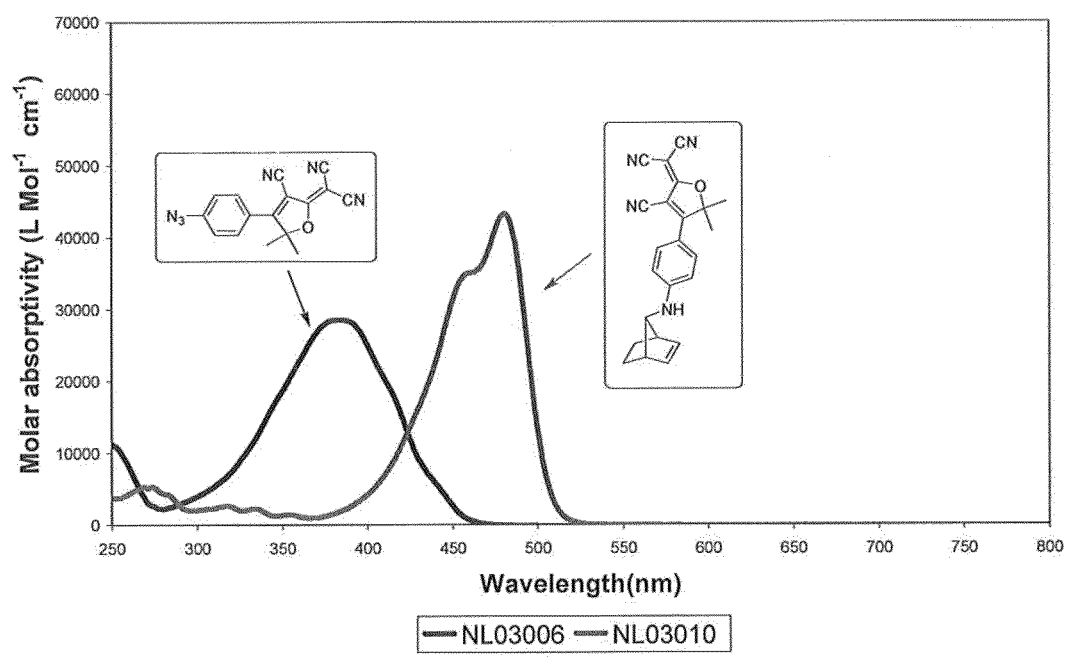
FIG. 21 is a graph of molar absorptivity and wavelength of NL03006 and NL03010 in CH$_2$Cl$_2$. NL03006: UV-Vis (CH$_2$Cl$_2$): $\lambda_{max}$=384 nm, $\epsilon$=2.86×10$^4$ L·mol$^{-1}$·cm$^{-1}$ and NL03010 UV-Vis (CH$_2$Cl$_2$): $\lambda_{max}$=481 nm, $\epsilon$=4.33×10$^4$ L·mol$^{-1}$·cm$^{-1}$.

Comparison of the IN-vis spectra of the DCDHF azide and the rearranged product is informative and is set forth in FIG. 21. The fluorogen is the DCDHF azide with λmax at 380 nm and λcutoff at 470 nm. The fluorophore has a more intense absorption, characteristic of a push-pull system, with λmax 480 nm and λcutoff 515 nm. As a result, the secondary amine can be pumped (to produce fluorescence) at wavelengths where the azide does not absorb (>~475 nm).

There was some concern that the natural presence of thiols in biological media might interfere with the thermal-azide to amine T-ATA process. Therefore, reactions were run between DCDHF azide and norbornene in a variety of solvents in the presence or absence of butanethiol. There was little difference found between reactions run in the presence or absence of butanethiol and so the presumption is that thiols will not interfere with the T-ATA in a cellular environment.

TABLE

Summary of a series of reactions between norbornene and azido-P-DCDHF with or without butanethiol

| Reac- tion # | A:N:B | Butane- thiol | Solvent | Isolated Yield of amine | SM recovery |
|---|---|---|---|---|---|
| NL02119 | 1:1 | No | CHCl₃ | — | — |
| NL03010 | 5:9 | No | MeOH + CH₂Cl₂ | 30% | 42% |
| NL03013 | 1:2 | No | THF | 28% | 40% |
| NL03020 | 2:1:9 | Yes | THF | 30% | 50% |
| NL03022 | 1.7:1:1.8 | Yes | THF | 27% | 60% |

A = azido-P-DCDHF  N = norbornene  B = butanethiol

As proof of structure for the secondary amine reaction product obtained from DCDHF azide and norbornene a crystal structure was performed which confirmed the anticipated structure.

X-ray structure (ball and stick):

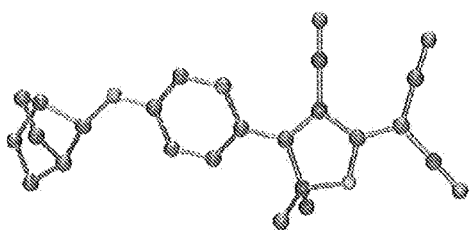

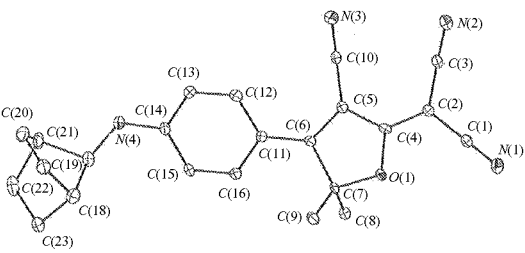

X-ray structure (thermal ellipsoid plot)

Figure 22:
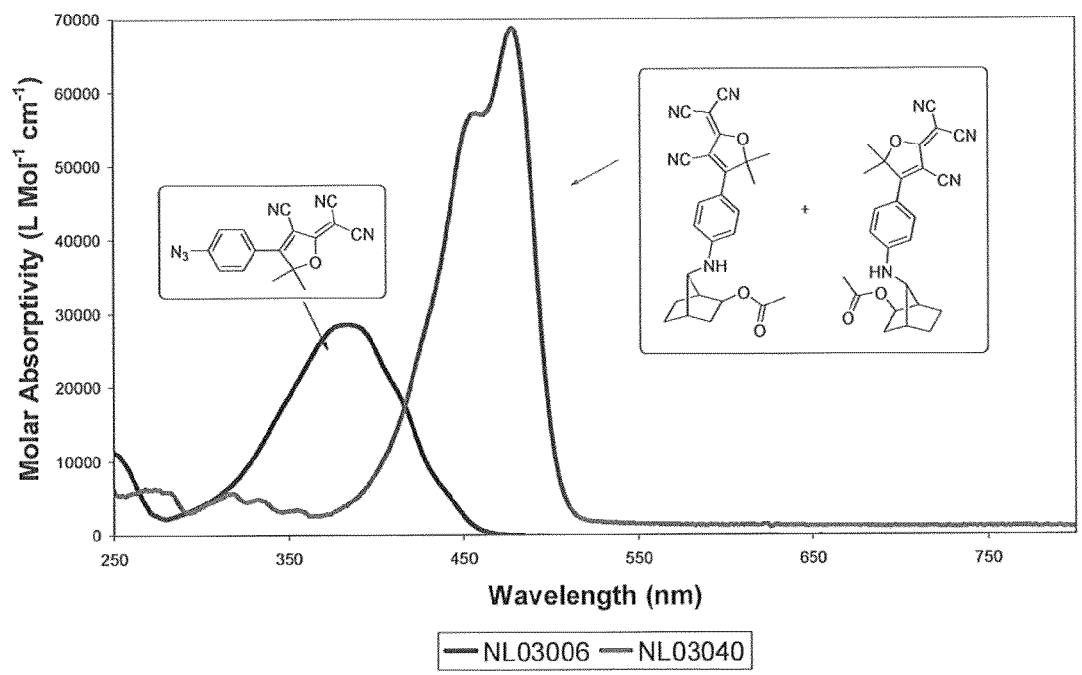
FIG. 22 is a graph of molar absorptivity and wavelength of NL03006 and NL03040 in CH$_2$Cl$_2$. NL03006: UV-Vis (CH$_2$Cl$_2$): $\lambda_{max}$=384 nm, $\epsilon$=2.9×10$^4$ L·mol$^{-1}$·cm$^{-1}$ and NL03010: UV-Vis (CH$_2$Cl$_2$): $\lambda_{max}$=478 nm, $\epsilon$=6.9×10$^4$ L·mol$^{-1}$·cm$^{-1}$.

The identity of the solvent medium in some cases has a large effect on the rate of reaction and the product distribution. For example, in a mixture or dichloromethane and acetic acid acetate ester products resulting from trapping by the solvent appear. Here again the secondary amine products have significantly red-shifted absorption and enhanced fluorescence relative to the azide precursor as seen in FIG. 22.

Figure 23:
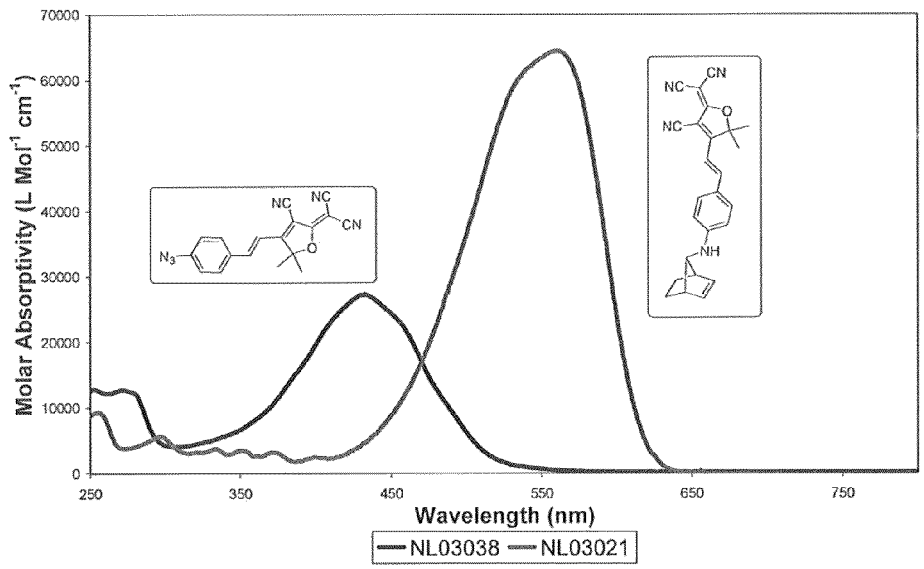
FIG. 23 is a graph of molar absorptivity and wavelength of NL0303$ and NL03021 absorption in $CH_2Cl_2$. NL03038: UV-Vis ($CH_2Cl_2$): $\lambda_{max}$=433 nm, $\epsilon$=2.7×10$^4$ L·mol$^{-1}$·cm$^{-1}$ and NL03021: UV-Vis ($CH_2Cl_2$): $\lambda_{max}$=561 nm, $\epsilon$=6.4×10$^4$ L·mol$^{-1}$·cm$^{-1}$.

Other DCDHF-type azides have been prepared and reacted with norbornene. The rate of reaction and outcome of the reaction in terms of product mix depends on the exact structures of the starting materials and other parameters concerned with the reaction system. For example, the vinylogous DCDHF azide has also been prepared and reacted with norbornene. In this case fluorescent dyes were produced but the reaction is relatively slow and it proved impossible to separate some of them. Therefore some of these reaction products were independently synthesized by an alternative sequence of reactions. The alternative route involves preparation of 4-azidobenzaldehyde, the reaction of the azidobenzaldehyde with norbornene to give a rearranged secondary amine benzaldehyde mixture, which could be separated, and then the reaction of the respective secondary amine aldehyde with methyl DCDHF. A comparison of the UV-vis of DCDHF-V azide vs. the DCDHF-V amine product obtained upon reaction with norbornene is as follows in FIG. 23:

As can be seen in FIG. 23, the addition of the alkene into the overall pi system has red shifted the λmax of absorption for the azide from 384 nm to 481 nm and the norbornene reaction product (secondary amine) from 433 nm to 561 nm which is a result that is useful for imaging applications. The addition of the extra alkene extending the pi slows down the overall reaction rate somewhat.

One approach which has delivered enhanced reaction rates for T-ATA involves structure modifications of the azide compound. As a representative example, the tetrafluoro derivative of azido DCDHF-V was reacted with norbornene (perfluorination of the azide substituted ring). The rate of reaction (amine production) is enhanced but also resulted in two undesirable side effects. The reaction now produces an aziridine product and the absorption wavelength of both the azide and aziridine products are shorter and the difference in wavelength between the azide and aziridine product is also reduced. The extinction coefficients are also diminished compared with the nonfluorinated compounds. These trends are seen in the diagram below and compared with the simple amine.

2-(4-{2-[4-(3-Aza-tricyclo[3.2.1.0$^{2,1}$]oct-3-yl)-2,3,5, 6-tetrafluoro-phenyl]-vinyl}-3-cyano-5,5-dimethyl-5H-furan-2-ylidene)-malononitrile (NL03062)

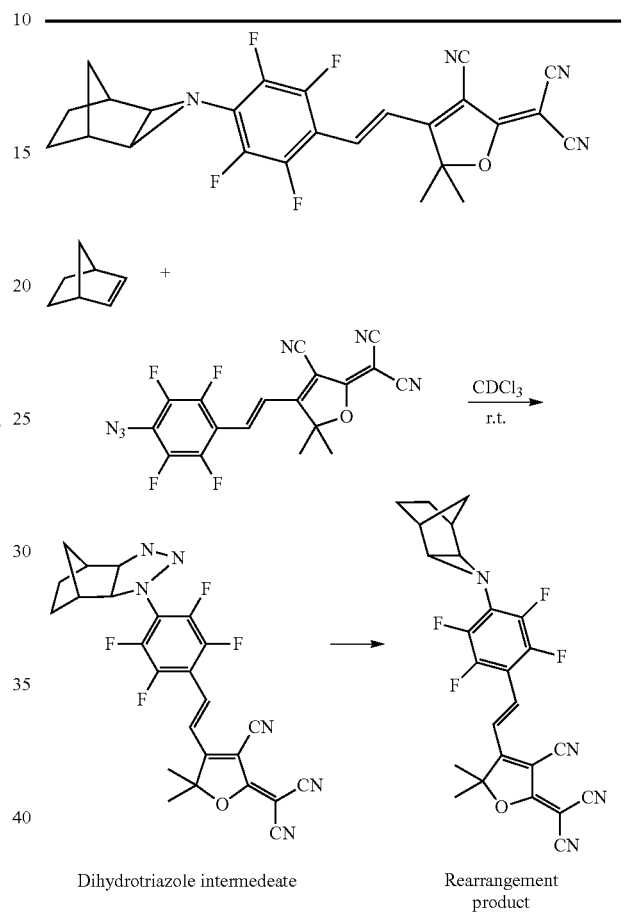

| Time (min) | SM (%) | IP (%) | RP (%) |
|---|---|---|---|
| 5 | 83 | 17 | |
| 35 | 41 | 45 | 14 |
| 65 | 28 | 28 | 44 |
| 95 | 17 | 41 | 42 |
| 125 | 11 | 33 | 56 |
| 155 | 0 | 28 | 72 |
| 185 | 0 | 23 | 77 |
| 215 | 0 | 9 | 91 |
| 245 | 0 | 0 | 100 |

SM: Azido compound

Norbornene (excess amount) and 2-{4-[2-(4-azido-2,3,5, 6-tetrafluoro-phenyl)-vinyl]-3-cyano-5,5-dimethyl-5H-furan-2-ylidene}-malononitrile (SM) were mixed together in an NMR tube with CDCl$_3$. The NMR tube was spinning in the NMR instrument and the reaction began instantly. After 5 minutes, some starting material was converted to the dihydrotriazole compound (its structure was identified from its NMR data), which is quite unstable and converted only to the rearrangement product, an aziridine compound at these reaction conditions (the aziridine compound formed here has the same NMR spectrum as the aziridine compound prepared independently). After about 2 h, the starting material was almost gone and the aziridine compound was the main component. After 4 h, the aziridine compound is the only component with some minor byproducts.

Figure 24:
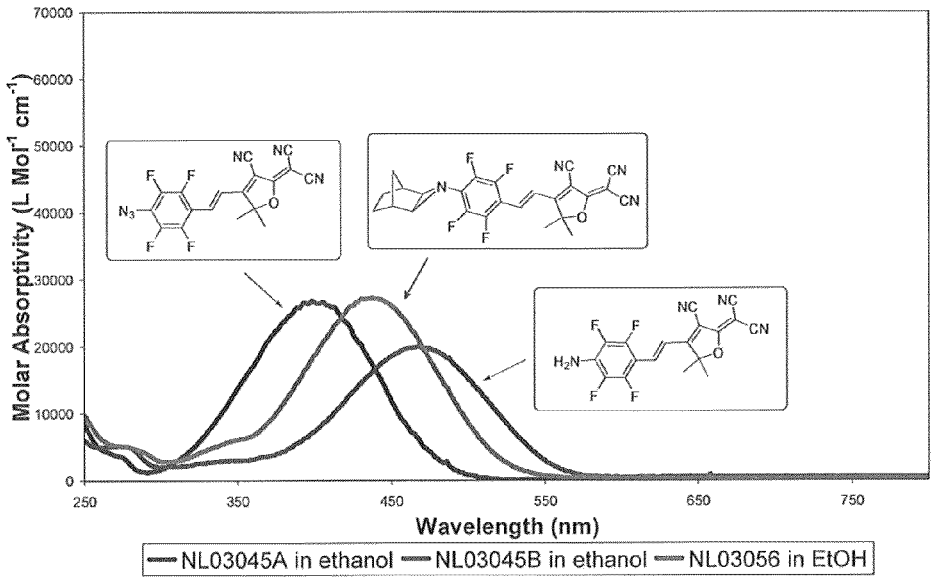
FIG. 24 is a graph of molar absorptivity and wavelength of NL03045A, NL03045B and NL03056 absorption in EtOH. NL03045A: UV-Vis (EtOH): $\lambda_{max}$=406 nm, $\epsilon$=2.7×10$^4$ L·mol$^{-1}$·cm$^{-1}$; NL03045B: UV-Vis (EtOH): $\lambda_{max}$=468 nm, $\epsilon$=2.0×10$^4$ L·mol$^{-1}$·cm$^{-1}$, and NL03056: UV-Vis (EtOH): $\lambda_{max}$=438 nm, $\epsilon$=2.7×10$^4$ L·mol$^{-1}$·cm$^{-1}$.

The final tetrafluorinated product was independently prepared by a route similar to that used previously for the non-fluorinated series. As can be seen in FIG. 24, in the UV-vis spectra in this series the aziridine and simple amine derivatives are not very much red shifted from the azide as the presence of fluorine attenuates the donor capability of the amines.

As such, adjustments in T-ATA rate must be pursued with careful attention to consequences in the spectra of the starting materials and products. Another adjustment is to use alternative more reactive alkenes instead of norbornene. The reactivity can be adjusted electronically or by change in strain resulting from adjustment of bond angles, twist of geometry and other distortions of the alkene.

The following includes synthesis, preparation and characterization of compounds used in the DCDHF series for T-ATA reactions:

2-(4-(4-Azidophenyl)-3-cyano-5,5-dimethylfuran-2 (5H)-ylidene)malononitrile (NL03006)

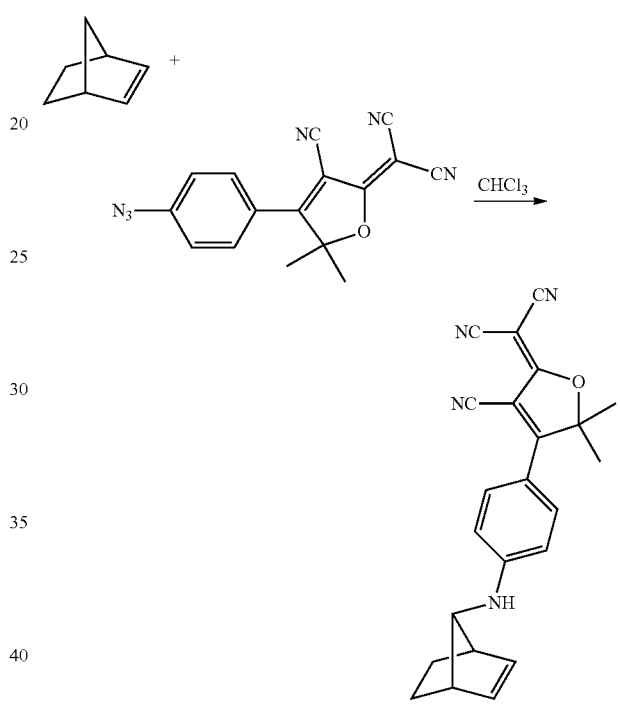

Figure 25:
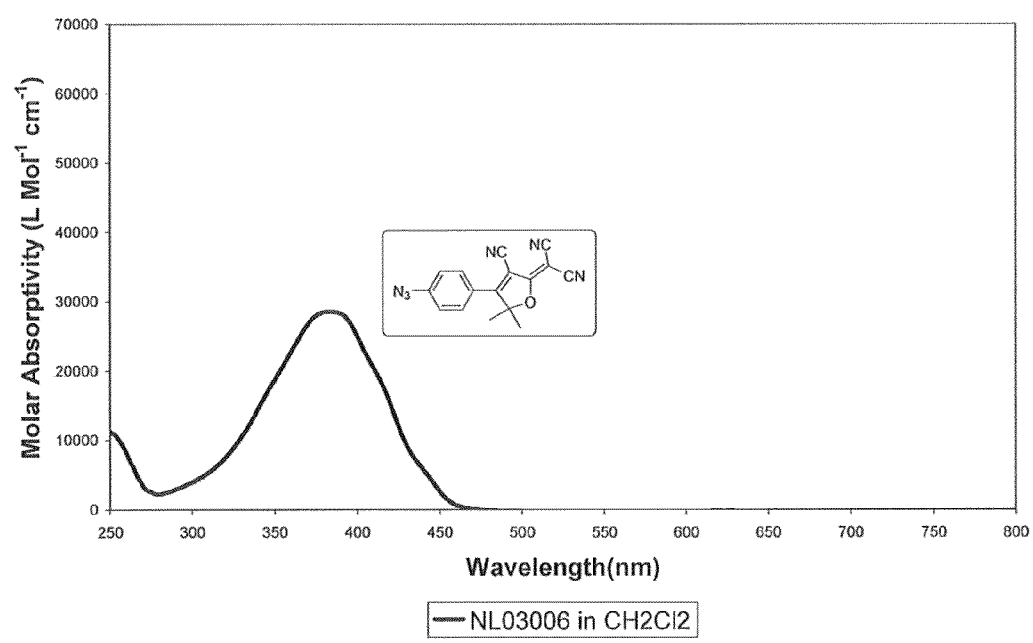
FIG. 25 is a graph of molar absorptivity and wavelength of NL03006 absorption in $CH_2Cl_2$. In the graph UV-V is ($CH_2Cl_2$): $\lambda_{max}$=384 nm, $\epsilon$=2.9×10$^4$ L·mol$^{-1}$·cm$^{-1}$.

To a 200-mL round bottom flask with stirbar was added 2-[3-cyano-4-(4-fluoro-phenyl)-5,5-dimethyl-5H-furan-2-ylidene]-malononitrile (0.20 g, 0.716 mmol) and DMSO (8 mL). The mixture was stirred at room temperature, then sodium azide (0.08 g, 1.23 mind) was added to it and the reaction continued to react at room temperature. After 2 h, the reaction mixture was completely homogeneous. The product mixture was poured into ice-water (300 mL) and stirred 0.5 h. The yellow precipitate was filtered out through suction filtration. The solid was recrystallized from 1-propanol to give the final product as a yellow solid having a UV spectra as set forth in FIG. 25; (0.19 g, 88% yield), IR (neat): 2924, 2228, 2113, 1567, 1533, 1366, 1279, 1188, 1111, 841 cm$^{-1}$. $^1$H NMR (400 MHz, DMSO): δ 7.94 (ddd, J=9.2, 2.8, 2.0 Hz, 2H), 7.40 (ddd, J=9.2, 2.8, 2.0 Hz, 2H), 1.78 (s, 6H), $^{13}$C NMR (100 MHz, DMSO): δ 177.1, 176.6, 145.0, 130.6, 123.4, 120.3, 112.3, 111.4, 111.3, 101.6, 100.3, 55.2, 24.9. UV-Vis (CH$_2$Cl$_2$): $\lambda_{max}$=384 nm, ϵ=2.9×10$^4$ L·mol$^{-1}$·cm$^{-1}$.

2-(4-(4-((1R,4S,7r)-Bicyclo[2.2.1]hept-2-en-7-ylamino)phenyl)-3-cyano-5,5-dimethylfuran-2(5H)-ylidene)malononitrile (NL02119) (reaction in chloroform)

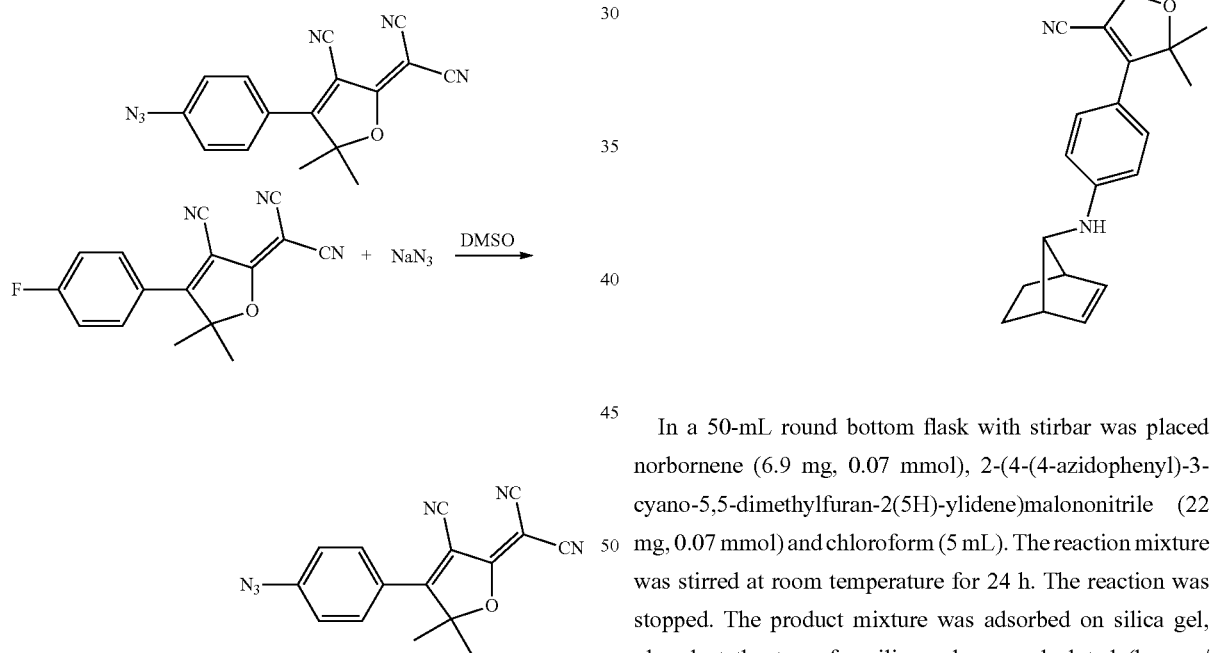

In a 50-mL round bottom flask with stirbar was placed norbornene (6.9 mg, 0.07 mmol), 2-(4-(4-azidophenyl)-3-cyano-5,5-dimethylfuran-2(5H)-ylidene)malononitrile (22 mg, 0.07 mmol) and chloroform (5 mL). The reaction mixture was stirred at room temperature for 24 h. The reaction was stopped. The product mixture was adsorbed on silica gel, placed at the top of a silica column and eluted (hexane/EtOAc=3/1) to give a red solid, which was recrystallized from 1-propanol to give the final product as red crystals. Mp 316° C. IR (neat): 3348, 2225, 1607, 1562, 1537, 1478, 1346, 1114, 838 cm$^{-1}$, $^1$H NMR (400 MHz, DMSO): δ 7.99 (br s, 1H), 7.94 (d, J=6.4 Hz, 2H), 6.80 (d, J=7.2 Hz, 2H), 6.04 (t, J=1.4 Hz, 2H), 3.50 (d, J=6.0 Hz, 1H), 2.96 (br s, 2H), 1.90-1.83 (m, 2H), 1.79 (s, 6H), 0.98 (d, J=3.6 Hz, 1H), 0.95 (d, J=4.0 Hz, 1H); $^{13}$C NMR (100 MHz, DMSO): δ 177.8, 174.3, 155.0, 132.8, 132.7, 132.3, 113.7, 113.65, 112.8, 112.6, 98.1, 88.5, 69.1, 50.2, 44.9, 26.6, 22.8. UV-Vis (CH$_2$Cl$_2$): $\lambda_{max}$=481 nm, $\epsilon$=4.3×10$^4$ L·mol$^{-1}$·cm$^{-1}$.

2-(4-(4-(((1R,4S,7r)-Bicyclo[2.2.1]hept-2-en-7-ylamino)phenyl)-3-cyano-5,5-dimethylfuran-2(5H)-ylidene)malononitrile (NL03010) (reaction in methanol)

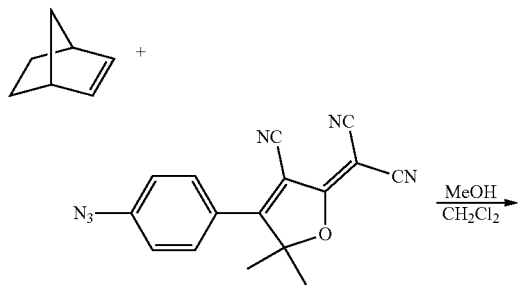

To a 200-mL round bottom flask with stirbar was added norbornene (0.095 g, 1 mmol), 2-(4-(4-azidophenyl)-3-cyano-5,5-dimethylfuran-2(5H)-ylidene)malononitrile (0.30 g, 1 mmol) and methanol (10 mL). The reaction mixture was stirred at room temperature for 1 h. Most of the starting material (azido-DCDHF) has not been dissolved in methanol yet. More methanol (20 mL) was added. There was still a large amount of undissolved azido-DCDHF starting material. Dichloromethane (30 mL) was added to it to help dissolve all starting material. The reaction was permitted to react for 8 h at room temperature, then more norbornene (0.02 g, 0.21 mmol) was added to it. After another 6 h, more norbornene (0.05 g, 0.5 mmol) was added to it and the reaction was permitted to react for another 6 h. The reaction was stopped. More dichloromethane (40 ml) was added to dissolve all solids. The product mixture was adsorbed on silica gel, placed at the top of a silica column and eluted (hexane/EtOAc=3/1) to give a red solid, which was recrystallized from 1-propanol to give the final product as red crystals having a UV spectra as set forth in FIG. 26; (0.12 g, 30% yield). Mp 316° C. IR (neat): 3348, 2225, 1607, 1562, 1537, 1478, 1346, 1114, 838 cm$^{-1}$. $^1$H NMR (400 MHz, DMSO): δ 7.99 (br s, 1H), 7.94 (d, J=6.4 Hz, 2H), 6.80 (d, J=−7.2 Hz, 2H), 6.04 (t, J=1.4 Hz, 2H), 3.50 (d, J=6.0 Hz, 1H), 2.96 (br s, 2H), 1.90-1.83 (m, 2H), 1.79 (s, 6H), 0.98 (d, J=3.6 Hz, 1H), 0.95 (d, J=4.0 Hz, 1H); $^{13}$C NMR (100 MHz, DMSO): δ 177.8, 174.3, 155.0, 132.8, 132.7, 132.3, 113.7, 113.65, 112.8, 112.6, 98.1, 88.5, 69.1, 50.2, 44.9, 26.6, 22.8; UV-Vis (CH$_2$Cl$_2$): $\lambda_{max}$=481 nm, $\epsilon$=4.3×10$^4$ L·mol$^{-1}$·cm$^{-1}$.

(1S,4S,7R)-7-(4-(4-Cyano-5-(dicyanomethylene)-2,2-dimethyl-2,5-dihydrofuran-3-yl)phenylamino)bicyclo[2.2.1]heptan-2-yl acetate and its enantiomer

(1R,2R,4R,7R)-7-(4-(4-Cyano-5-(dicyanomethylene)-2,2-dimethyl-2,5-dihydrofuran-3-yl)phenylamino)bicyclo[2.2.1]heptan-2-yl acetate (NL03040) (Reaction of DCDHF Azide with Norbornene in the Presence of Acetic Acid)

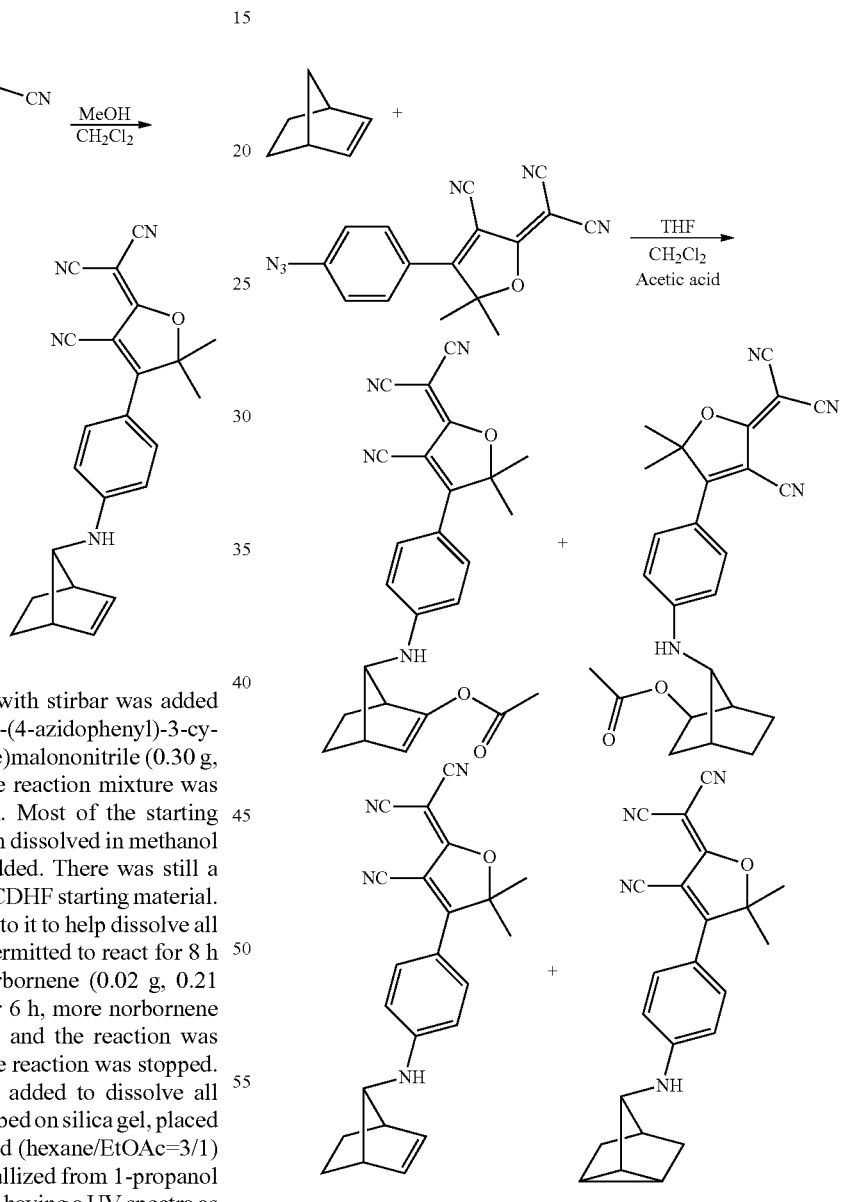

To a 100-mL round bottom flask with stirbar was added 2-(4-(4-azidophenyl)-3-cyano-5,5-dimethylfuran-2(5H)-ylidene)malononitrile (0.604 g, 2 mmol), norbornene (0.235 g, 2.5 mmol), dichloromethane (30 mL), anhydrous THF (10 mL) and acetic acid (10 mL). The above mixture was stirred at room temperature under nitrogen. In the beginning, a little bit 2-(4-(4-azidophenyl)-3-cyano-5,5-dimethylfuran-2(5H)- ylidene)malononitrile was not dissolved. After a while, all starting material was dissolved completely. The reaction was kept at room temperature for 24 h. Some red solid was precipitated out and the solid was filtered off by suction filtration. $^1$H NMR showed that this is the mixture of above four product (as shown in the above reaction, the two enantiomer were predominant. Their structures were assigned on the NMR data). The solid was dissolved into $CH_2Cl_2$ (200 mL). The crude product was preloaded on silica gel, placed at the top of silica column and eluted (hexane/$CH_2Cl_2$/EtOAc=50/50/1). Fractions containing only the first two products (they are just next to each other and hard to be separated) were combined and concentrated to give red solid. This is the mixture of the last two products (around 3/1 ratio according to their NMR data). The eluent was changed to $CH_2Cl_2$/EtOAc=25/1. Fractions containing only the third product were combined and concentrated to give a dark yellow solid, which was recrystallized from $CH_2Cl_2$/1-propanol to give an orange solid (0.40 g, 50% yield). This is the mixture of above enantiomer. Mp 278° C., IR (neat): 3362, 2959, 2223, 1714, 1611, 1582, 1539, 1488, 1397, 1360, 1322, 1259, 1116, 837 cm$^{-1}$. $^1$H NMR (400 MHz, CDCl$_3$): δ 7.98 (d, J=9.2 Hz, 2H), 6.70 (d, J=8.8 Hz, 2H), 6.65 (d, J=7.2 Hz, 1H), 4.92 (dd, J=7.6, 3.2 Hz, 1H), 3.65 (d, J=6.8 Hz, 1H), 2.53 (t, J=4.4 Hz, 1H), 2.45 (d, J=4.4 Hz, H), 2.12 (s, 3H), 2.10-2.01 (m, 1H), 1.86 (s, 6H), 1.85-1.72 (m, 3H), 1.38-1.29 (m, 2H); $^1$H NMR (400 MHz, DMSO): δ 8.02 (d, J=8.8 Hz, 2H), 7.60 (d, J=5.6 Hz, 1H), 6.91 (d, J® 9.2 Hz, 2H), 4.61-4.53 (m, 1H), 3.61 (d, J=5.6 Hz), 2.40-2.30 (m, 1H), 2.11-2.02 (m, 1H), 1.96-1.88 (m, 1H), 1.81 (d, 6H), 1.79 (s, 3H), 1.77-1.60 (m, 2H), 1.26-1.13 (m, 2H); $^{13}$C NMR (100 MHz, DMSO): δ 178.4, 175.1, 170.4, 155.2, 114.24, 114.2, 113.6, 113.1, 98.8, 90.0, 77.2, 61.1, 43.2, 38.9, 37.3, 27.17, 27.15, 26.0, 23.0, 21.3, UV-Vis (CH$_2$Cl$_2$): λ$_{max}$=478 nm, ε=$^4$ 6.9×10$^4$ L·mol$^{-1}$·cm$^{-1}$.

4-Azidobenzaldehyde (NL03003)

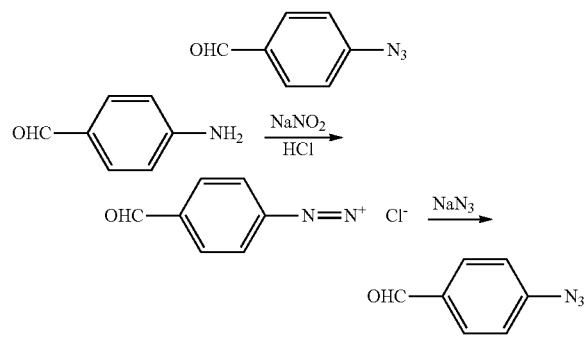

To a 500-mL round bottom flask with stirbar was added 4-amino-benzaldehyde (2.0 g, 0.0165 mol) and diluted hydrochloric acid (4 N, 150 mL). The mixture was cooled in ice-water bath to keep the temperature around 0° C. Sodium nitrite (2.28 g, 0.033 mol) solution in water (20 mL) was added to the above mixture at 0° C. and stirred for 0.5 h, and then sodium azide (2.15 g, 0.033 mol) solution in water (20 mL) was added to the above mixture dropwise to keep the temperature at 0° C. (a lot of foam were formed in this process). The reaction was warmed gradually to room temperature over 1 h, and then permitted to react at room temperature overnight. TLC showed that there was only one main product in the reaction mixture so the reaction was stopped. The crude product was extracted with EtOAc (50 mL×5) and the combined organic layers were dried with anhydrous MgSO$_4$. After removing the solvent, a light yellow liquid was obtained as the pure final product (2.30 g, 95% yield), IR (neat): 3062, 2114, 1693, 1597, 1578, 1503, 1282, 1166, 1126, 852 cm$^{-1}$. $^1$H NMR (400 MHz, CDCl$_3$): δ 9.97 (s, 1H), 7.91 (dt, J=8.8, 2.0 Hz, 2H), 7.19 (dt, J=8.8, 2.0 Hz, 2H); $^1$H NMR (400 MHz, MeOD): δ 7.45 (dt, J=8.8, 2.0 Hz, 2H), 7.08 (dt, J=8.8, 2.0 Hz, 2H), 5.38 (s, 1H); $^{13}$C NMR (100 MHz, CDCl$_3$): δ 190.7, 146.4, 133.2, 131.6, 119.5.

(E)-2-(4-(4-Azidostyryl)-3-cyano-5,5-dimethylfuran-2(5H)-ylidene)malononitrile (NL03038)

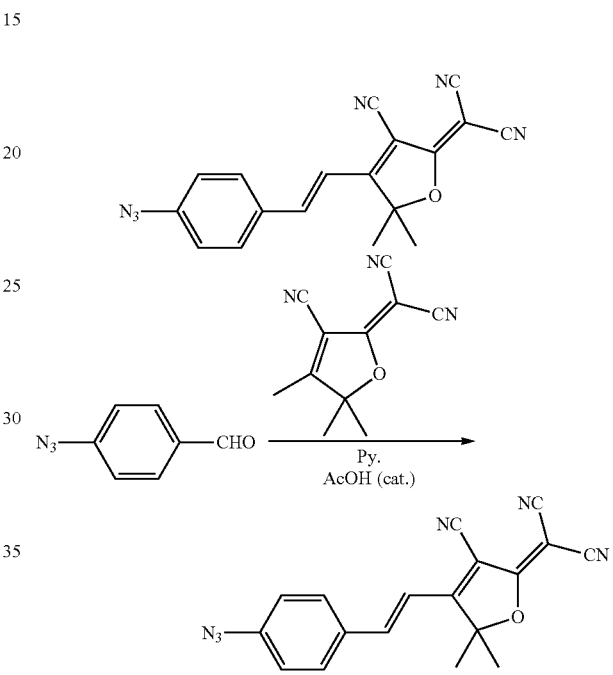

2-{4-(4'-Azidophenylethenyl)-3-cyano-5,5-dimethyl-5H-furan-2-ylidene}-malononitrile: The 4-azidobenzaldehyde (2.00 g, 13.6 mmol) and 3-cyano-2-dicyanomethylene-4,5,5-trimethyl-2,5-dihydrofuran (2.70 g, 13.6 mmol) were dissolved in 90 mL pyridine and a few drops of acetic acid were added. The mixture was stirred at room temperature for 24 h, poured into water, stirred for 30 min, kept in the refrigerator overnight, and then the precipitate was filtered off and air dried. The material was further purified by silica-gel column chromatography using hexane/EAC (7:3) as eluent and then filially recrystallized from dichloromethane/1-propanol to give the product as a solid (2.00 g, 44% yield), Mp 177-178° C., IR (neat) 3060, 2992, 2227, 2118, 1575, 1526, 1380 cm$^{-1}$. $^1$H NMR (400 MHz, CDCl$_3$): δ 7.61 (d, 2H, 8.4 Hz), 7.56 (d, 2H, J=16.4 Hz), 7.09 (d, 2H, J=8.4 Hz), 6.92 (d, J=16.4 Hz, 2H), 1.77 (s, 6H); $^{13}$C NMR (100 MHz, CDCl$_3$): δ 174.5, 173.19, 145.65, 144.52, 130.48, 130.18, 119.84, 114.00, 111.27, 110.52, 109.94, 97.30, 26.23. UV-vis (CH$_2$Cl$_2$): λ$_{max}$=433 nm; Anal. Calcd for C$_{16}$H$_{12}$N$_6$O: C, 65.85; H, 3.68; N, 2560. Found: C, 65.58; H, 3.74; N, 25.94.

(E)-2-(4-(4-Azido-2,3,5,6-tetrafluorostyryl)-3-cyano-5,5-dimethylfuran-2(5H)-ylidene)malononitrile: To a 100-mL round bottom flask with stirrer was added 4-azido-2,3,5,6-tetrafluorobenzaldehyde (0.22 g, 1 mmol) and 2-(3-cyano. 4,5,5-trimethyl-5H-furan-2-ylidene)-malononitrile (0.22 g, 1.1 mmol), pyridine (5 mL) and acetic acid (several drops).

The mixture was stirred at room temperature for 2.5 days. TLC showed the desired azido product had been formed as the main product. The reaction was stopped and poured into ice-water (500 mL). After stirring for 2 h, the precipitate was filtered off by suction filtration. The solid was recrystallized from 1-propanol. After recrystallization, part of the azido product was converted to the corresponding amino compound. The mixture was adsorbed on silica gel, placed at the top of a silica column and eluted ($CH_2Cl_2$/EtOAc=20/1). Fractions containing only the first product were combined and concentrated to give an orange product (40 mg, 10% yield). This is the final azido product, (E)-2-(4-(4-azido-2,3,5,6-tetrafluorostyryl)-3-cyano-5,5-dimethylfuran-2(5H)-ylidene)malononitrile. Recrystallization cannot be done on this compound, since it has high photo-reactivity. It is readily converted to the corresponding amino compound in solvents (like propanol) in daylight. IR (neat); 2933, 2228, 2124, 1586, 1557, 1489, 1372, 1253, 998 cm-1, 1H NMR (400 MHz, CDCl3); δ 7.63 (d, J=16.8 Hz, 1H), 7.31 (d, J=16.4 Hz, 1H), 1.82 (s, 6H); $^{13}C$ NMR (100 MHz, $CDCl_3$): δ 174.5, 172.5, 146.9 (m), 144.4 (m), 142.0 (m), 139.4 (m), 130.7, 121.4 (t, J=9.8 Hz), 111.1, 110.3, 109.5, 102.6, 97.8, 51.3, 26.3; 19F NMR (470 MHz, $CDCl_3$): δ 143.5 (2F), −155.2 (2F). UV-vis (EtOH): $\lambda_{max}$=406 nm, $\epsilon$=2.7×10$^4$ L mol$^{-1}$ cm$^{-1}$ HRMS m/z Calcd. for $C_{18}H_8F_4N_6O$ (M+Na): 423.0593. Found 423.0590.

(E)-2-(4-(4-Azido-2,3,5,6-tetrafluorostyryl)-3-cyano-5,5-dimethylfuran-2(5H)-ylidene)malononitrile: To a 100-mL round-bottom flask with stirbar was added 4-azido-2,3,5,6-tetrafluoro-benzaldehyde (0.22 g, 1.1 mmol) and 2-(3-cyano-4,5,5-trimethyl-5H-furan-2-ylidene)-malononitrile (0.22 g, 1.1 mmol), 5 mL pyridine and several drops of acetic acid. The mixture was stirred at room temperature for 2.5 days. TLC showed the desired azido product had been formed as the main product. The reaction was stopped and poured into 500 mL ice-water. After stirring for 2 h, the precipitate was filtered off by suction filtration. The solid was recrystallized from 1-propanol. After recrystallization, part of the azido product was converted to the corresponding amino compound. The mixture was adsorbed on silica gel, placed at the top of a silica column and eluted ($CH_2Cl_2$:EtOAc=20:1). Fractions containing only the first product were combined and concentrated to give an orange product (40 mg, 10% yield). This is the final azido product, (E)-2-(4-(4-azido-2,3,5,6-tetrafluorostyryl)-3-cyano-5,5-dimethylfuran-2(5H)-ylidene)malononitrile. Recrystallization could not be done on this compound, since it has high photoreactivity: it readily converts to the corresponding amino compound in solvents (like propanol) in daylight. IR (neat): 2933, 2228, 2124, 1586, 1557, 1489, 1372, 1253, 998 cm$^{-1}$, 1H NMR (400 MHz, $CDCl_3$): δ 7.63 (d, J=16.8 Hz, 1H), 7.31 (d, J=16.4 Hz, 1H), 1.82 (s, 6H); $^{13}C$ NMR (100 MHz, $CDCl_3$): δ 174.5, 172.5, 146.9 (m), 144 (m), 142.0 (m), 139.4 (m), 130.7, 121.4 (t, J=9.8 Hz), 111.1, 110.3, 109.5, 102.6, 97.8, 51.3, 26.3; $^{19}F$ NMR (470 MHz, $CDCl_3$): δ −143.5 (2F), −155.2 (2F). UV-vis (EtOH): $\lambda_{max}$=406 nm, $\epsilon$=2.7×10$^4$ L mol$^-$cm$^{-1}$.

To a 100-mL round bottom flask with stirbar was added 4-azido benzaldehyde (0.30 g, 2 mmol), 2-(3-cyano-4,5,5-trimethyl-5H-furan-2-ylidene)-malononitrile (0.40 g, 2 mmol), pyridine (5 mL) and acetic acid (several drops). The mixture was stirred at room temperature for 2.5 days. TLC showed the desired azido product had been formed as the main product. The reaction was stopped and poured into ice-water (1 L). After stirring for 2 h, the precipitate was filtered off by suction filtration. The solid was recrystallized from 1-propanol to give the final product as a dark red solid (0.55 g, 84% yield). This compound decomposes at around 180° C. before melting (observed under microscope and DSC). IR (neat); 2227, 2119, 1600, 1530, 1281, 1184, 823 cm$^{-1}$. 1H NMR (400 MHz, $CDCl_3$): δ 7.67 (d, J=8.8 Hz, 2H), 7.60 (d, J=16.4 Hz, 1H), 7.15 (d, 8.4 Hz, 2H), 7.0 (d, J=16.4 Hz), 1.83 (s, 6H); $^{13}C$ NMR (100 MHz, $CDCl_3$): δ 175.2, 173.5, 145.9, 144.8, 130.8, 130.5, 120.1, 114.3, 111.6, 110.8, 110.2, 99.9, 97.6, 51.1, 26.5. Anal. Calcd for $C_{18}H_{12}N_6O$; C, 65.85; H, 3.68; N, 25.60. Found: C, 65.58; H, 3.74; N, 25.94. UV-Vis ($CH_2Cl_2$): $\lambda_{max}$=433 nm, $\epsilon$=2.7×10$^4$ L·mol$^{-1}$·cm$^{-1}$.

4-(3-Aza-tricyclo[3.2.1.0$^{2,4}$]oct-3-yl)-2,3,5,6-tetrafluoro-benzaldehyde (NL03051A)

4-((1R,4S,7r)-Bicyclo[2.2.1]hept-2-en-7-ylamino)-2,3,5,6-tetrafluorobenzaldehyde (NL03051B)

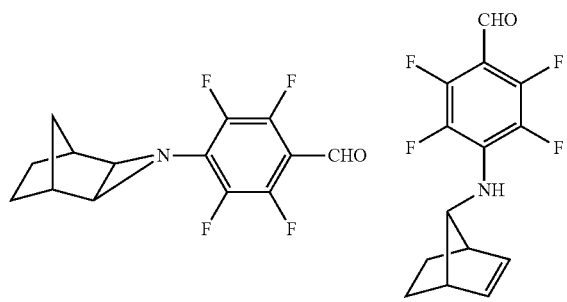 [SMILES: O=Cc1c(F)c(F)c(N2C3C4CCC(C4)C32)c(F)c1F ; O=Cc1c(F)c(F)c(NC2C3C=CC2CC3)c(F)c1F]

NL03051A  NL03051B

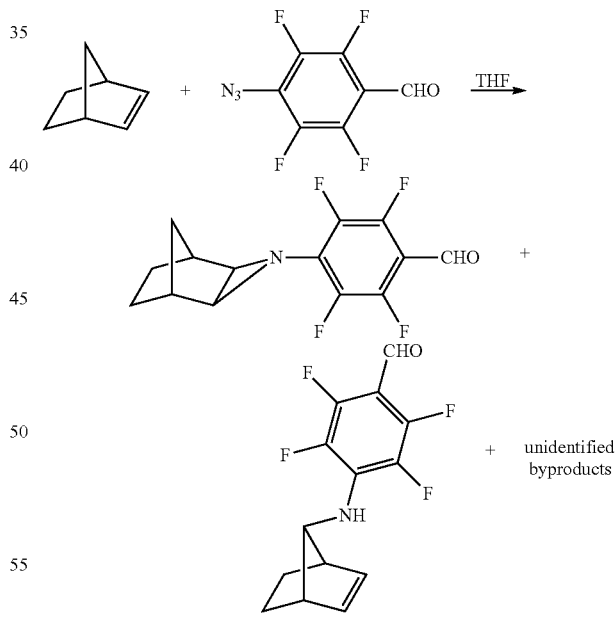

In a 100-mL round bottom flask with stirbar was added norbornene (0.24 g, 0.0025 mol), 4-azido-2,3,5,6-tetrafluoro-benzaldehyde (0.44 g, 0.002 mol) and THF (8 mL). The mixture was stirred at room temperature under nitrogen for 24 h. TLC showed that four products had been formed. The reaction was stopped and the product mixture was preloaded directly on silica gel, placed at the top of a column and eluted (hexane/EtOAc=20/1). Fractions containing only the first product (the first product was very minor among all four products) and second product were combined and concentrated to give yellow solid. This is mainly 4-(3-aza-tricyclo[3.2.1.0$^{2,4}$]oct-3-yl)-2,3,5,6-tetrafluoro-benzaldehyde (further purification did not apply here since only very small amount of the first product was produced, the second product is the main product in all four products formed here, 0.35 g, 62% yield). $^1$H NMR (400 MHz, CDCl$_3$): δ 10.21-10.17 (m, 1H), 2.69 (br 5, 4H), 1.63-1.50 (m, 3H), 1.35-1.20 (m, 2H), 1.00-0.95 (m, 1H). Fractions containing only the second and third products were combined and concentrated to give a yellow oily product. This is the mixture of 4-(3-aza-tricyclo[3.2.1.0$^{2,4}$]oct-3-yl)-2,3,5,6-tetrafluoro-benzaldehyde and 4-((1R,4S,7r)-bicyclo-[2.2.1]hept-2-en-7-ylamino)-2,3,56-tetrafluorobenzaldehyde (the latter is the second main product). $^1$H NMR data of the second main product is as follows: $^1$H NMR (400 MHz, CDCl$_3$): δ 10.11-10.08 (m, 1H), 6.08 (s, 2H), 4.90 (br s, 1H), 4.00-3.90 (m, 1H), 3.00-2.95 (m, 2H), 1.90-1.84 (m, 2H), 1.12-1.06 (m, 2H); Fractions containing only the fourth product were combined and concentrated to give a yellow solid. Its structure has not been identified yet.

2-(4-{2-[4-(3-Aza-tricyclo[3.2.1.0$^{2,4}$]oct-3-yl)-2,3,5,6-tetrafluoro-phenyl]-vinyl}-3-cyano-5,5-dimethyl-5H-furan-2-ylidene)-malononitrile (NL03056)

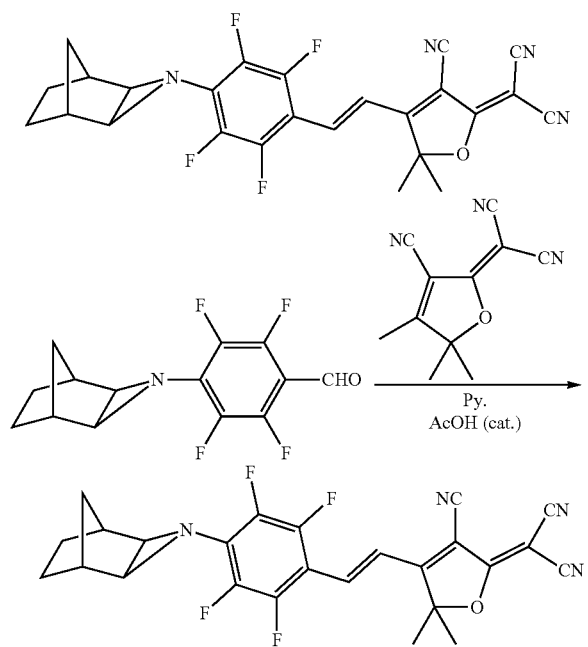

In a 100-mL round bottom flask with stirbar was added 4-(3-aza-tricyclo[3.2.1.0$^{2,4}$]oct-3-yl)-2,3,5,6-tetrafluoro-benzaldehyde (0.35 g, 1.23 mmol), 2-(3-cyano-4,5,5-trimethyl-5H-furan-2-ylidene)-malononitrile (0.39 g, 2 mmol), pyridine (5 mL) and acetic acid (several drops). The mixture was stirred under nitrogen at room temperature for 3 days. TLC showed that one red fluorescent product had formed as the main product. The reaction was stopped. The product mixture was poured into ice-water (500 mL) and vigorously stirred for 4 h. The crude products were extracted with CH$_2$Cl$_2$ (100 mL×5). The combined organic layer was dried over anhydrous MgSO$_4$. After removing solvent, the crude organic product was adsorbed on silica gel, placed at the top of a silica column and eluted (hexane/EtOAc=2/1). Fraction containing only the first red fluorescent product were combined and concentrated to give a red solid, which was recrystallized from 1-propanol to give the final product as red needles. Mp 233° C. IR (neat): 2951, 2228, 1573, 1481, 1390, 1366, 1163, 1107, 983, 962 cm$^{-1}$. $^1$H NMR (400 MHz, CDCl$_3$): δ 7.64 (d, J=16.8 Hz, 1H), 7.23 (d, J=16.8 Hz, 1H), 2.70 (br s, 4H), 1.80 (s, 6H), 1.63-1.51 (m, 3H), 1.34-1.27 (m, 2H), 0.98-0.92 (m, 1H); $^{13}$C NMR (100 MHz, CDCl$_3$): 176.4, 173.4, 148-139 (m), 132.5, 118.8 (t), 111.4, 110.6, 109.9, 97.6, 95.3 (m).

Demonstration of T-ATA with a stilbazolium azide. It was found that a stilbazolium azide also reacts with norbornene to produce a new compound, likely a secondary amine, with a red shifted absorption. See the synthesis of Formula 5, set forth hereinabove hereby fully incorporated by reference including preparation of Formulas 5A and 5B. The thermal transformation of azide to amine has been monitored by UV-vis and NMR.

Stilbazole compound 4-(2-pyridin-4-yl-vinyl)-phenylamine was prepared by a known method (Loew, L. M., Hassner, A. Birnbaum, D. *J. Org. Chem.* 1984, 49, 2546) by Heck reaction of 4-vinylpyridine and 4-iodoaniline. The amine was converted to the azide by a standard diazotization technique. Alkylation of the pyridine in the stilbazole converted it to the stilbazolium salt. The stilbazolium salt is the fluorogen in the overall process.

Once the stillbazolium azide was synthesized, its reactivity with norbornene was tested. Because of the ionic nature of these compounds and hence their extremely high polarity, TLC could not be used to monitor reaction progress. Therefore, these reactions were followed using UV-vis absorption spectroscopy. Because the azide functionality is a relatively weak donor group at best, or even a weak acceptor group, the formation of a dihydrotriazole adduct or a subsequent amine, each a stronger electron donor, should show a bathochromic shift. The overall reaction sequence is shown below in Scheme 11.

The amine fluorophore is the desired fluorophore to produce as it is more red-shifted and likely more fluorescent that the dihydrotriazole intermediate. However the dihydrotriazole itself may also suffice in some cases as the fluorophore.

Scheme 11

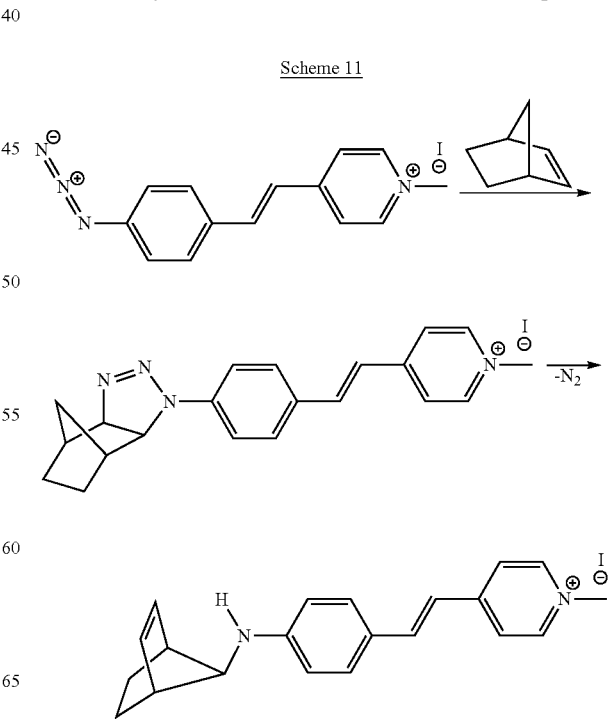

Figure 26:
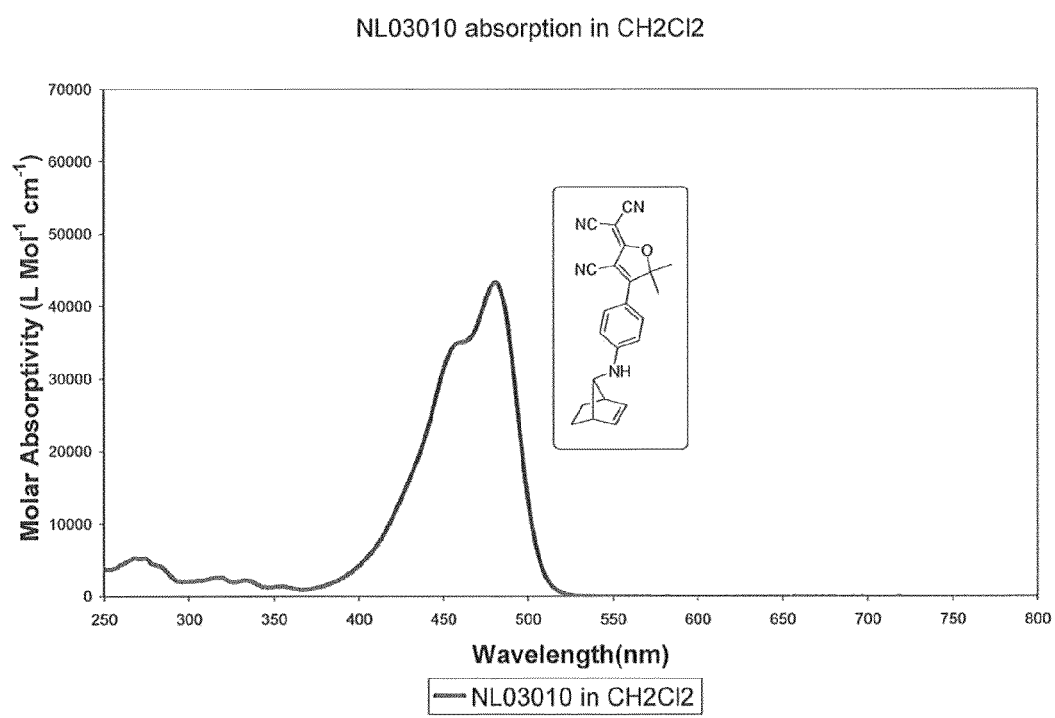
FIG. 26 is a graph of molar absorptivity and wavelength of NL03010 absorption in $CH_2Cl_2$. In the graph UV-Vis ($CH_2Cl_2$): $\lambda_{max}$=481 nm, $\epsilon$=4.3×10$^4$ L·mol$^{-1}$·cm$^{-1}$.
Figure 27:
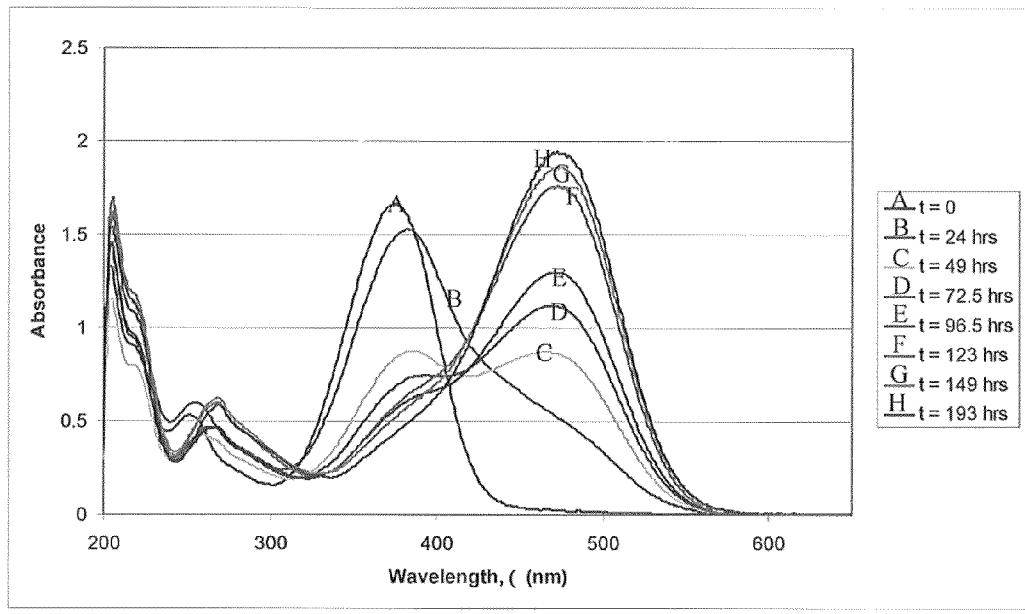
FIG. 27 illustrates time elapsed UV-visible spectra for the reaction of stilbazolium azide with norbornene in methanol at 55° C. The azide with peak absorbance wavelength about 375 nm is consumed with a new product appearing at 475 nm.

In methanol, a reaction between the stilbazolium azide with a peak absorbance wavelength at about 375 nm and the norbornene was seen at room temperature as evidenced by the appearance of a new peak at 475 nm. At elevated temperature (55° C.) the reaction progressed at a faster rate. The time-elapsed sequence of UV-vis spectra for this reaction is shown in FIG. 26. While it is clear from these spectra that a reaction occurred, it is not clear what species formed since no product was isolated. It is likely that the amine product is dominant, since the dihydrotriazole adduct is unlikely to produce such a large red shift. While the shift in absorbance is dependent on many factors, a similar experiment using an azido DCDHF system found that a red-shift of 92 nm relative to the azide counterpart occurred when the secondary amine was the product. Because of the similar shift found with the stilbazolium-azide system, it was expected that the secondary amine was formed in this experiment. The fluorescence properties of the species with absorption λmax at 475 nm remain to be examined. The rates of the initial cycloaddition reaction and the rates of decomposition of the dihydrotriazole to the amine products are dependent on a range of factors still under study. A time-elapsed NMR study in chloroform showed a clean transformation from the azide to new product. It is unknown whether the new compound formed in chloroform is the same as is formed in methanol. In any case, the thermal ATA process in the specific stilbazolium system described here may be too slow for most applications in a biological system. Modification of the rate, for example by structure and functional group transformations in the components, can influence the reaction rate.

Demonstration of T-ATA with an NBD (nitrobenzoxadiazole) azide. NBD fluorophores have been very popular for a variety of biological applications although they do have a relatively short wavelength pumping and fluorescence wavelengths. The NBD system is well suited to demonstrate to concepts of both photochemical and thermal ATA. The synthesis of NBD-azide is straightforward, and the process, starting from commercially available 7-chloro-4-nitrobenzoxadiazole, is set, forth herein above with respect to Formula 4 and hereby incorporated by reference.

The reactivity of NBD-azide, Formula 4, with norbornene was studied in both methanol and chloroform. In methanol the norbornene added to the azide giving at least four fluorescent products, including a secondary amine NBD fluorophore product (structure 26) after loss of nitrogen. This secondary amine has absorption in the visible $\lambda_{max}^{CH2Cl2}$ 465 nm ($\epsilon$ 2.07×10$^4$). In contrast to the reaction in methanol the reaction in chloroform produces a product which is an NBD azirdine fluorophore (27) $\lambda_{max}^{CH2Cl2}$ 447 nm ($\epsilon$ 1.54×10$^4$). This is an example how solvent can influence the structure of the amine product in the thermal ATA process.

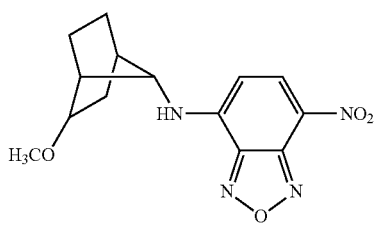

(26)

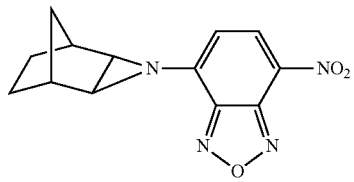

(27)

To compare the UV-vis spectra of the T-ATA fluorophores with a known NBD fluorophore, 7-diethylamino-4-nitrobenzoxadiazole (28), $\lambda_{max}^{CH2Cl2}$ 483 nm ($\epsilon$ 2.51×10$^4$), was synthesized by substitution of the chlorine in 7-chloro-4-nitrobenzoxadiazole with diethylamine. The relative absorption peak wavelength of these three compounds are consistent with the assigned structures

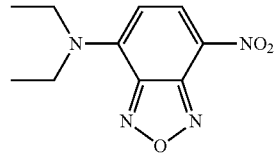

(28)

When NBD-azide was reacted with norbornene in methanol at room temperature, a secondary amine product was isolated from a mixture of four fluorescent products produced. Because of the formation of a carbocation species after the loss of nitrogen, instead of reforming a double bond, in this case the carbocation is trapped with methanol, attaching a methoxy group to the norbornane system. Because of this methoxy group, a mixture of isomers was obtained in the isolated product. Because of this there is structural ambiguity in the $^1$H NMR spectrum of (26).

In chloroform, the reaction of NBD-azide with norbornene afforded the aziridine product after loss of nitrogen. No dihydrotriazole product was detected in the product isolated from this reaction and this is probably due to the electronic properties of the NBD system. This reaction occurred nearly quantitatively at room temperature in approximately 20 minutes with only a small excess of norbornene present. In fact, the reaction proceeded so quickly that nitrogen gas was seen being liberated from solution. Such impressive results in terms of yield and reaction rate have not been seen in other systems but indicate that with appropriate structure modification systems can deliver the needed kinetics for biological application of the thermal ATA process.

Even though the adducts are highly fluorescent (both the secondary amine from the reaction in methanol and the aziridine from the reaction in chloroform), as noted a shortcoming of these fluorophores is that their emission wavelengths are too short to be practical in cellular imaging studies. However, because of this system's good behavior in forming a fluorophore both quickly and efficiently, it is possible that it could find use in applications other than cellular imaging where a long emission wavelength is not required.

Synthesis of (2-methoxy-bicyclo[2.2.1]hept-7-yl)-(7-nitro-benzoxadiazol-4-yl)-amine (26): In a 50-mL round bottom flask equipped with a stirbar, 7-azido-4-nitrobenzoxadiazole (25.5 mg, 0.124 mmol) was mixed with norbornene (40.0 mg, 0.425 mmol) in methanol (5 mL) and stirred at room temperature for 4.5 hrs. TLC showed four distinct spots, all of which were fluorescent. The solvent was evaporated and the crude product was added to a column of silica gel and eluted with a 1:1 mixture of hexane and ethyl acetate. The second product was collected and recrystallized from methanol to give lustrous orange crystals in the amount of 8.3 mg (22% yield). Other products were not isolated due to close similarities in $R_f$ values but appeared to be present in similar (~25%) yields. mp 177.9-180.3° C. $^1$H NMR (400 MHz, CDCl$_3$) δ 8.50 (d, J=8.7 Hz, 1H), δ 8.13 (s, 1H), δ 6.18 (d, J=8.7 Hz, 1H), S 3.84-338 (m, 1H), δ 3.67-3.63 (m, 1H), δ 3.45 (s, 3H), δ 2.64-2.58 (m, 2H), δ 1.95-1.72 (m, 4.35H), δ 1.40-1.17 (m, 6.52M), δ 0.9-4.0.80 (m, 2.36H). $^{13}$C NMR (100 MHz, CDCl$_3$) δ 136.6, 97.8, 84.7, 62.6, 56.5, 42.9, 38.8, 36.5, 29.7, 26.7, 22.5. $\lambda_{max}^{CH2Cl2}$ 465 nm (ε 2.07×10$^4$).

Synthesis of 3-(7-Nitrobenzoxadiazol-4-yl)-3-aza-tricyclo [3.2.1.0$^{2,4}$]octane (27): In a 50-mL round bottom flask equipped with a 7-azido-4-nitrobenzoxadiazole (0.203 g, 0.985 mmol) was mixed with norbornene (0.109 g, 1.16 mmol) in chloroform (5 and stirred at room temperature for 2 hrs. TLC showed complete conversion. The solution was concentrated until crystals began to form and then placed in the refrigerator for 1 h. The crystals were filtered yielding the product as small red-orange crystals in the amount of 0.25 g (92% yield). mp 1322-133.1° C. $^1$H NMR (400 MHz, CDCl$_3$) δ 8.45 (d, J=8.2 Hz, 1H), δ 6.71 (d, J=8.2 Hz, 1H), 82.92 (s, 2H), δ 2.82 (s, 2H), δ 1.69-1.62 (m, 2H), δ 1.59-1.54 (m, 1H), δ 1.39-1.33 (m, 2H), 81.07 (d, J=10.4 Hz, 1H). $^{13}$C NMR (100 MHz, CDCl$_3$) δ 149.9, 146.5, 143.9, 133.8, 128.4, 111.7, 43.9, 36.5, 29.1, 25.7. $\lambda_{max}^{CH2Cl2}$ 447 nm (ε 1.54×10$^4$).

Synthesis of 7-Diethylamino-4-nitrobenzoxadiazole (28): In a 50-mL round bottom flask equipped with a stirbar, 7-chloro-4-nitrobenzofurazen (0.10 g, 0.501 mmol) and diethylamine (44 mg, 0.601 mmol) were stirred in ethanol (5 mL) for 30 min at room temperature. TLC shows consumption of starting material. The solution was poured into ice water, forming a precipitate which was filtered and washed with water. The product was collected as small orange crystals in the amount of 0.115 g (97% yield). mp 133.0-136.2° C., $^1$H NMR (400 MHz, CDCl3) δ 8.47 (d, J=9.1 Hz, 1H), δ 6.15 (d, J=9.1 Hz, 1H), $\lambda_{max}^{CH2Cl2}$ 483 nm (ε 2.51×10$^4$).

Thermal Conversion of a Fluorogen to a Fluorophore via an Alkyne or a Strained Alkyne (T-AAT)

As an alternative approach to the chemical creation of fluorescence from an azide-pi-acceptor fluorogen (P-ATA or T-ATA already described in detail), a "click" reaction of an azide with an alkyne-pi-acceptor fluorogen may be accomplished (T-ATT). Here, the precursor fluorogen is an acetylene or strained alkyne connected to the pi-acceptor structure, and a second compound, also a fluorogen, contains an azide. Alternatively, an azide-pi-acceptor fluorogen molecule may be reacted with an alkyne or strained alkyne fluorogen; however, the preferred form in the cases we have examined is an acetylene- or strained alkyne-pi-acceptor fluorogen reacting with an azide fluorogen (reaction type [I] below). That is, the present invention provides a method by which an azide compound, when reacted with an alkyne or a strained alkyne, yields a fluorophore that can be excited and imaged by visible light. The acceptors generally include the acceptors set forth hereinabove with respect to the photoactivation route as well as specific acceptors set forth in Formulas 1 through 8, all of which are hereby fully incorporated by reference. The pi compounds of the fluorogen include the pi compounds set forth hereinabove with regard to the photoactivation route and the same is fully incorporated by reference including the various pi compounds set forth in Formulas 11 through 19. The pi-acceptor compounds are terminated by either an alkyne or a strained alkyne group as set forth hereinbelow. The result of this reaction is a triazole-pi-acceptor (or donor-triazole-pi-acceptor) fluorophore that is achieved through a thermal reaction. A similar triazole-pi-acceptor (or donor-triazole-pi-acceptor) fluorophore can be obtained by reacting an alkyne or a strained alkyne compound with an azide-pi-acceptor compound, that is the pi-acceptor groups instead of having an alkyne or strained alkyne end group attached to the pi structure has an azide, end group attached to the pi structure (type [II] below). In both cases the triazole unit may act as an electron donor or, more likely, a bridge for a different electron donor. Generally, these two types of reactions are set forth as follows.

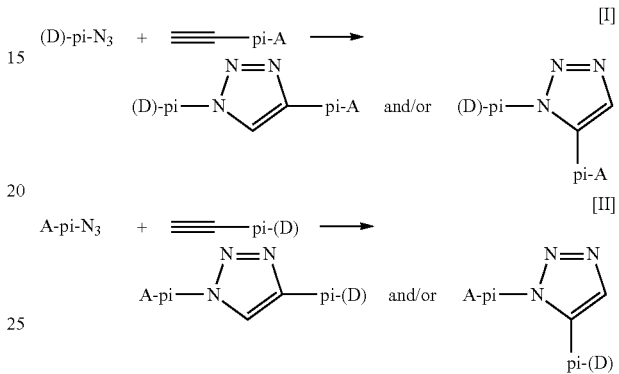

The T-AAT reaction is performed between an azide compound and an alkyne compound to give a 1,2,3-triazole product. Both the azide and alkyne precursors may be considered fluorogens and the product triazoles are, relatively, fluorophores although the actual difference of spectroscopic properties amongst them is highly dependent on the particular substitution pattern of the precursors and the isomer structure of the products. The azide compound may be substituted by a donor [I] or acceptor [II] (i.e. donor-pi-azide or azide-pi-acceptor, respectively) and likewise the acetylene compound may be substituted by a complementary acceptor [I] or donor [II] (i.e. alkyne-pi-acceptor, or donor-pi-alkyne, respectively). We have also examined some cases in which there is no donor group intentionally installed on the azide component.

The general reaction conditions employed for producing the triazole-pi-acceptor compounds are somewhat different from the reaction conditions for the production of an amine-pi-acceptor fluorophore (or a dihydrotriazole-pi-acceptor compound) in the T-ATA reactions. The main difference is that the azide+alkyne (T-AAT) reactions were run using copper catalysis while the thermal (T-ATA) reactions did not involve catalysis. The temperature range for the copper-catalyzed process was in the range of 50-70° C. Ethanol was used as solvent but other suitable solvents include water, alcohols containing from 2 to about 10 carbon atoms such as ethanol or methanol, or other protic solvents as well as mixtures of such solvents as well as other solvents known to the art and to the literature. Like the azide+alkene reaction, the azide+alkyne reaction also responds to strain relief and electronic influence; therefore, strained alkyne systems may eliminate the need for a copper catalyst. For instance, initial bioconjugation applications employing copper catalysis in the literature have been largely supplanted by systems with activated alkynes: S. Brase, et. al., "Cycloaddition Reactions of Azides Including Bioconjugation", *Topics in Heterocyclic Chemistry*, 12, 45-115 (2008). The amounts of reactants are dependent upon the application but generally are utilized in equal relative molar amounts while greater proportions of one of the reactants or the other reactants can be readily utilized.

Typical alkynes or strained alkynes that can be utilized in the present invention have the formula $R^1—C\equiv C—R^2$ where $R^2$ is the said pi-acceptor system for reaction type [I] above (or donor-pi system for [II]) and $R^1$ is a donor-pi or pi-acceptor, for [I] and [II], respectively. $R^1$ can also be a hydrogen atom; or an alkyl group having from 1 to about 10 carbon atoms wherein the alkyl group can contain one or more halide atoms thereon such as bromine; or an aromatic group; or a substituted aromatic group; or an alkyl substituted aromatic group having a total of from 7 to 20 carbon atoms; or a cyclic or heterocyclic group having from 4 to about 10 carbon atoms; or combinations of aromatic, substituted aromatic, cyclic, and heterocyclic groups. If a simple strained alkyne such as cyclooctyne is employed there are no sites available for other donor or acceptor groups other than those already on the azide. However, if a more conjugated strained alkyne is employed, such as an annulyne or benzocyclooctyne or (Z)-cyclooct-1-en-3-yne, then a more fully conjugated system is available derived from a strained alkyne.

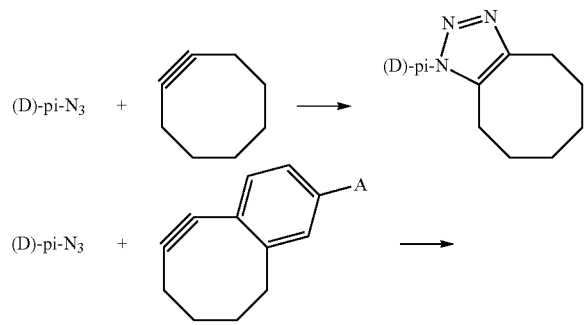

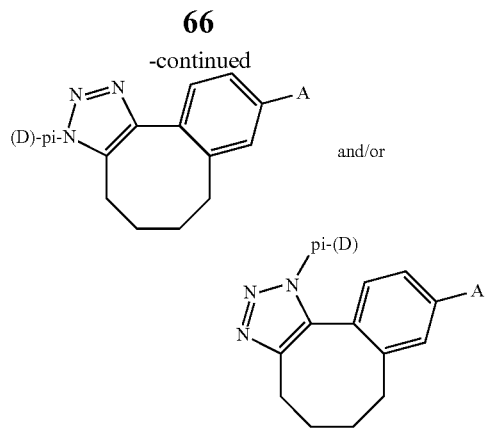

Examples of conceptual use of a strained alkyne in a T-AAT process in the case of the reaction of a donor-pi-azide to a simple cyclooctyne, an adduct will result with little acceptor component (due to absence of acceptor in the starting alkyne). However, if an acceptor-substituted alkyne is used (In this example an acceptor-substituted benzocyclooctyne), then a more polar product results which will be more likely to have a red-shifted chromophore. The structures in this figure refer to a type [I] T-AAT reaction, but the same rationale as just described applies for the opposite combination of azide-pi-acceptor cyclooctyne or donor-substituted benzocyclooctyne (type [II]).

Specific examples of the preparation and reactions of type [I] alkyne-pi-acceptor compounds (here alkyne-pi-DCDHF) with a variety of azide-pi-donor and azide-pi compounds with no donor intentionally installed as well as the synthesis of the latter azide compounds, are set forth below. Some example compounds for type [II] T-AAT (or even ATA) reactions are also described, such as the azide-pi-DCDHF.

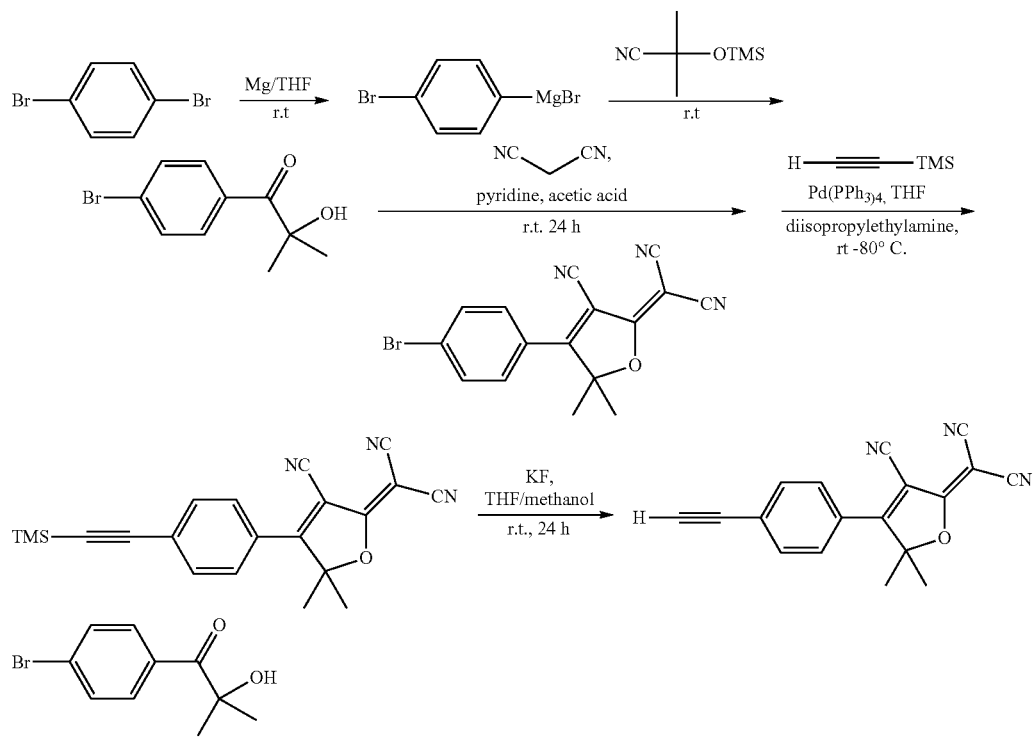

1-(4-Bromophenyl)-2-hydroxy-2-methyl-propan-1-one. In a dry 250 ml three necked flask was placed magnesium turnings (2.46 g, 101.2 mmol), 5 ml dry THF and two drops of 1,2-dibromoethane, stirred under N$_2$ at room temperature. Subsequently 1,4-dibromobenzene (19.8 g, 84 mmol) in 15 ml dry THF was added dropwise over 30 min. An ice water bath was occasionally used to moderate the reaction. After addition was complete the reaction was stirred for 2 hrs to complete conversion of bromobenzene. A solution of 2-methyl-2-trimethylsilanyloxy-1-propionitrile (13.25 g, 85 mmol) in 15 ml dry THF was added dropwise to the Grignard reagent and the mixture was stirred for 20 hrs. By this time a large quantity of white precipitate was formed. The intermediate produced was hydrolyzed by cautious addition of 80 ml 6N HCl with ice cooling and vigorous stirring as the solution warmed to room temperature and then kept stirring at this temperature for 4 hrs. Solid sodium bicarbonate was added cautiously to neutralize the excess acid and the solid in the mixture was removed by vacuum filtration through a pad of Celite and the Celite pad was washed three more times with ethyl acetate. The filtrate was extracted three times with ethyl acetate, dried over anhydrous MgSO$_4$. The solvent was removed by rotary evaporation and the product obtained as liquid, which was suitable for direct use in the next step. For further characterization one gram of the crude product was purified by silica gel column chromatography using EtOAc/hexane 1/4 as eluent. Calculated yield: (77%). $^1$H NMR (400 MHz, CDCl$_3$) δ 7.88 (d, J=8.4 Hz, 2H), 7.49 (d, J=8.4 Hz, 2H), 4.01 (s, 1H), 1.51 (s, 6H). $^{13}$C NMR (100 MHz, (100 MHz, CDCl$_3$) δ 203.21, 134.46, 132.63, 131.28, 127.68, 76.66, 28.11.

3-Cyano 2-dicyanomethylen-5,5-dimethyl-4-(4-bromophenyl)-2,5-dihydrofuran. A mixture of the crude liquid 1-(4-bromophenyl)-2-hydroxy-2-methyl-propan-1-one (28.0 g, 65% 115 mmol, 74 mmol), malononitrile (35 g, 0.52 mol), acetic acid (0.4 g) and dry pyridine (100 mL) was stirred at room temperature for 24 hrs. The reaction mixture was then poured into 1 L of ice water with vigorous stirring and kept in the refrigerator overnight. The yellow precipitate was collected by vacuum filtration, washed with methanol and dried under vacuum. The product was recrystallized from 70% dichloromethane/methanol. Yield: 10.0 g (40%). mp: 235° C. $^1$H NMR (400 MHz, CDCl$_3$) δ 1.77 (s, 6H),) 7.58 (d, J=8.4 Hz, 2H), 7.72 (d, J=8.4 Hz, 2H). $^{13}$C NMR (100 MHz, (100 MHz, CDCl$_3$) δ 176.55, 174.76, 133.35, 129.40, 129.18 125.89, 111.05, 110.19, 110.05, 99.21, 26.09.

The following two examples relate to the preparation of an alkyne fluorogen (for type [I] reactions).

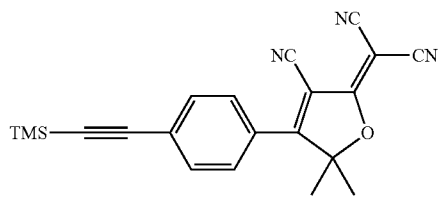

3-Cyano-2-dicyanomethylene-5,5-dimethyl-4-(4'-trimethylsilylethynyl phenyl)-2,5-dihydrofuran. To an oven dried flask containing a magnetic stir bar and condenser, Pd(PPh$_3$)$_4$ (160.0 mg, 0.14 mmol), cuprous iodide (70 mg, 0.36 mmol) and 1-(4-bromophenyl)-2-hydroxy-2-methyl-propan-1-one (800 mg, 2.35 mmol) was added, evacuated and back flushed with N$_2$. Dry THF (25 mL) was added followed by dry degassed diisopropylethylamine (1.60 mL, 9.2 mmol) and stirred for 10 min. Trimethylsilylacetylene (0.65 mL, 4.5 mmol) was added and stirred at rt for 4 h and subsequently at 80° C. for 1 hr. The mixture was cooled to room temperature, poured into water and extracted with CH$_2$Cl$_2$ (X 3). The combined organic layers were washed with a saturated solution of ammonium chloride and water, dried over anhydrous MgSO$_4$ and the solvent was removed by rotary evaporation. The crude product was further purified by column chromatography over silica gel, hexane/EAC 7:3 as eluent. The pure product separated as yellow solid. Yield: 0.55G (66%). mp. 201° C., $^1$H NMR (400 MHz, CDCl$_3$) δ 7.69 (d, J=8.8 Hz, 2H) 7.60 (d, J=8.8 Hz, 2H), 1.76 (s, 8H), 0.22 (s, 9H), $^{13}$C NMR (100 MHz, CDCl$_3$) δ 178.56, 174.34, 133.14, 129.25, 128.18, 126.51, 111.23, 110.32, 102.97, 101.85, 100.96, 99.23, 26.28.

Formula 18

3-Cyano-2-dicyanomethylene-5,5-dimethyl-4-(4'-ethynylphenyl)-2,5-dihydrofuran. (RS01039) Potassium) fluoride (260 mg, 4.5 mmol) was added to a solution of 2-dicyanomethylene-3-cyano-5,5-dimethyl-4-(4'-trimethylsilylethynylphenyl)-2,5-dihydrofuran (500 mg, 1.4 mmol) in degassed THF/methanol (1.5:1, 40 mL). The reaction mixture was stirred for 24 h at room temperature, poured into water, stirred for 1 hr, kept in the refrigerator overnight, filtered and air-dried. The product was recrystallized from dichloromethanel/1-propanol, Yield: 330 mg. (90%), mp: 225° C., $^1$H NMR (400 MHz, CDCl$_3$) δ 7.72 (d, J=8.8 Hz, 2H), 7.67 (d, J=8.8 Hz, 2H), 3.36 (s, 1H), 1.81 (s, 6H). $^{13}$C NMR (100 MHz, CDCl$_3$) 176.24, 174.31, 133.32, 128.00, 126.93, 110.98, 110.06, 109.97, 102.50, 99.08, 82.29, 81.71, 26.13. IR (neat, cm$^{-1}$ 2965, 2226, 1623, 1614, 1534.

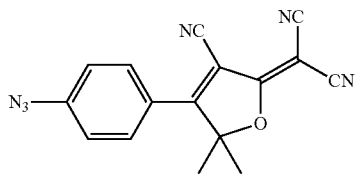 [SMILES: CC1(C)OC(=C(C#N)C#N)C(C#N)=C1c1ccc(N=[N+]=[N-])cc1]

2-[4-(4-Azido phenyl)-3-cyano-5,5-dimethyl-5H-furan-2-ylidene]malononitrile (RS01031) (for type [II] reactions)

A solution of NaNO$_2$ (0.69 g, 10.0 mmol) in 10 mL water was added dropwise to a solution of 2-[4-(4-aminophenyl)-3-cyano-5,5-dimethyl-5H-furan-2-ylidene] malononitrile (1.4 g, 5.0 mmol) in 30 mL 4M HCl at 0-5° C. After stirring the mixture at this temperature for 46 min, a solution of NaN$_3$ (0.53 g, 8.0 mmol) in 10 mL water was added dropwise to the mixture at the same temperature. Stirring was continued for 1 h below 5° C. and then at room temperature overnight. The precipitate formed was filtered off, washed with water and air-dried. The yellow product was recrystallized from dichloromethane/1-propanol. Yield: 1.25 g (82%). Mp; 184° C. IR (neat) 3056, 2990, 2235, 2122, 2091, 1601, 1568 cm$^{-1}$; $^1$H NMR (400 MHz, DMSO) δ 7.90 (d, J=8.8 Hz, 2H), 7.26 (d, J=8.8 Hz, 2H), 1.86 (s, 6H); $^{13}$C NMR (100 MHz, CDCl$_3$) δ 177.1, 176.6, 145.0, 130.61, 123.4, 120.30, 112.35, 111.4, 111.3, 101.60, 100.30, 55.20, 24.90; Anal, Calcd for C$_{16}$H$_{10}$N$_6$O: C, 63.57; H, 3.33; N, 27.80. Found: C, 63.51H, 3.44; N, 27.20; UV-Vis (CH$_2$Cl$_2$): $\lambda_{max}$=384 nm ϵ=2.9×10$^4$ L.mol$^{-1}$cm$^{-1}$.

1-Azidooctane (RS0210)

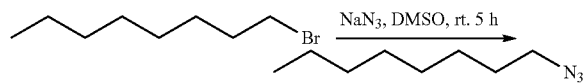

In a 100 mL round bottomed flask, sodium azide (2.60 g, 37.6 mmol) was dissolved in 80 mL DMSO, 1-Octyl bromide (5.5 g, 28.4 mmol) was added and stirred at room temperature for 5 h. The reaction was quenched by addition of water (200 mL) and was stirred for 1 h. The mixture was extracted with diethyl ether (50×3). The combined organic layers were washed with brine solution. The ether solution was dried over anhydrous MgSO$_4$ and the solvent was removed by rotary evaporation. The product was further purified by filtration through a short silica gel column using hexane as eluent. Yield: 2.5 g (78%) IR (neat) 2957, 2857, 2093, 1466, 1377, 1279 cm$^{-1}$; $^1$H NMR (400 MHz, CDCl$_3$) δ 3.21 (d, J=6.2 Hz, 2H), 1.55-1.57 (m, 2H), 1.25-1.32 (m, 10H), 0.84 (m, 3H); $^{13}$C NMR (CDCl$_3$) δ 51.51, 31.80, 29.19, 29.16, 28.89, 26.77, 22.66, 14.06,

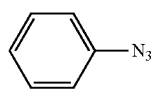

Azidobenzene (RS01073)

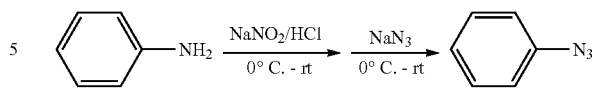

A solution of NaNO$_2$ (5.7 g, 82.5 mmol)) in water (20 mL) was added dropwise to a solution of aniline (3.06 g, 33 mmol) in 4M HCl (330 mL) at 0-5° C. After stirring the mixture at this temperature for 45 min, a solution of NaN$_3$ (429 g, 66 mmol) in water (20 mL) was slowly added to the mixture at the same temperature. Stirring was continued for 30 min below 5° C. and then for overnight at room temperature. The reaction mixture was extracted with diethyl ether (50×3), washed with water and dried over anhydrous MgSO$_4$. The solvent was removed under reduced pressure and the crude liquid was purified by silica gel column chromatography using hexane/EAC 0-5% as eluent. Yield: 1.70 g (43%). IR (neat) 2925, 2093, 1933, 1620, 1492, 1295, 1175 cm$^{-1}$; $^1$H NMR (400 MHz, CDCl$_3$) δ7.10-7.21 (m, 2H), 7.22-7.24 (m, 1H), 7.42-7.46 (m, 2H); $^{13}$C NMR (CDCl$_3$) δ 140.02, 129.72, 124.88, 109.00.

2-{3-Cyano-5,5-dimethyl 4-[4 (1-octyl-1H-[1,2,3]triazol-4-yl)phenyl]-5H-furan-2-ylidene}malononitrile (RS02011) (type [I] reaction)

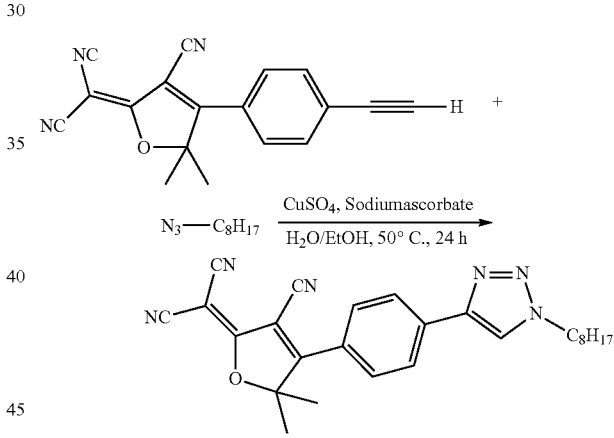

A mixture of 2-[3-cyano-4-(4-ethynyl-phenyl)-5,5-dimethyl-5H-furan-2-ylidene]malononitrile (90 mg, 0.34 mmol) and 1-azidooctane (80 mg, 0.51 mmol) in 15 mL ethanol was stirred at 50° C. under nitrogen and a solution of sodium ascorbate (25 mg, 0.12 mmol in 1 mL water) was added, followed by copper sulfate (15 mg, 0.06 mmol in 1 mL water) solution. The resulting mixture was stirred at the same temperature for 24 h, cooled and the reaction mixture was poured into cold water (100 mL). The mixture was stirred overnight at room temperature, the precipitate formed was filtered off and air dried. The crude product was recrystallized from dichloromethane/1-propanol, Yield: 70 mg (46%) Mp (DSc): 203° C.; IR (neat) 2933, 2974, 2266, 1574, 1565 cm$^{-1}$, $^1$H NMR (400 MHz, CDCl$_3$) δ 8.02 (d, J=8.4 Hz 2H), 7.87 (s, 1H), 7.85 (d, J=8.4 Hz, 2H), 4.39 (t, J=7.2 Hz, 2H), 1.94-1.96 (m, 2H), 1.82 (s, 6H), 1.20-1.31 (m, 10H), 0.82 (t, 3H); $^{13}$C NMR (CDCl$_3$) δ 176.69, 175.14, 145.30, 136.33, 129.01, 126.40, 125.91, 121.03, 111.20, 110.47, 110.38, 100.79, 99.08, 59.85, 50.44, 31.41, 30.01, 29.41, 28.76, 28.66, 26.20, 22.31, 13.78; Anal. Calcd for C$_{26}$H$_{28}$N$_6$O: C, 70.89; H, 6.41, N, 19.08. Found: C, 70.59, H, 6.18; N, 19.37. UV-Vis (CH$_2$Cl$_2$): $\lambda_{max}$=384 nm $\epsilon$=3.01×10$^4$ L.mol$^{-1}$cm$^{-1}$.

2-{3-Cyano-5,5-dimethyl 4-[4 (1-phenyl-1H-[1,2,3]triazol-4-yl)phenyl]-5H-furan-2-ylidene}malononitrile (RS01086) (type [I] reaction)

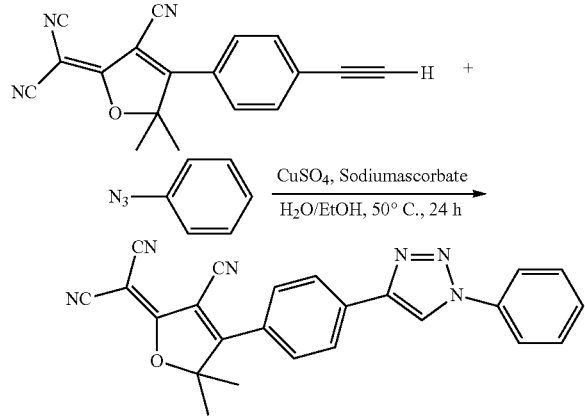

A mixture of 2-[3-cyano-4-(4-ethynyl-phenyl)-5,5-dimethyl-5H-furan-2-ylidene]malononitrile (150 mg, 0.53 mmol) and azidobenzene (80 mg, 0.67 mmol) in 20 mL ethanol was heated to 50° C. and stirred under N$_2$. Sodium ascorbate (30 mg, 0.15 mmol in 1 mL water) solution was added followed by copper sulfate (20 mg, 0.08 mmol in 2 ml . . . water) solution. The mixture was stirred at 50° C. for 24 h, cooled and poured into cold water (100 mL) and was stirred at room temperature for 1 h. The precipitate formed was filtered off and air-dried. The crude product was further purified by silica gel column chromatography using hexane/EAC 30-50% and then recrystallized from dichloromethane/1-propanol. Yield: 140 mg (65%) mp 298° C.; IR (neat) 2930, 2232, 1580 cm$^{-1}$; $^1$H NMR (400 MHz, DMSO) δ 9.44 (s, 8.19 (d, J=8.4 Hz, 2H), 7.94-8.00 (m, 2H), 7.63-7.65 (m, 2H), 7.53-7.62 (m, 1H), 1.86 (s, 6H); $^{13}$C NMR (CDCl$_3$) δ 177.26, 176.73, 145.69, 136.31, 134.75, 129.74, 129.24, 128.76, 126.64, 125.91, 121.12, 120.02, 112.06, 111.17, 110.98, 102.32, 100.33, 55.58 23.82; Anal, Calcd for C$_{24}$H$_{16}$N$_6$O: C, 71.28; H, 3.99; N, 20.78 Found: C, 70.95; H, 3.74; N, 26.04; UV-Vis(CH$_2$Cl$_2$): $\lambda_{max}$=384 nm $\epsilon$=3.22×10$^4$ L.mol$^{-1}$cm$^{-1}$.

2-{3-Cyano 5,5-dimethyl 4-[4 (4-phenyl-[1,2,3]triazol-1-yl)-phenyl]-5H-furan-2-ylidene}malononitrile (RS01057) (type [II] reaction)

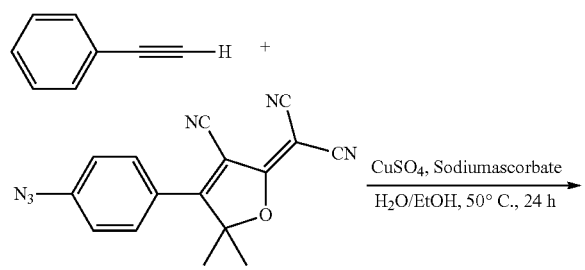

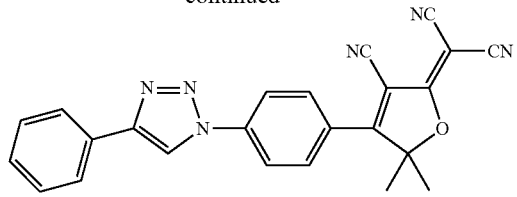

A mixture of 2-[4-(4-azido phenyl)-3-cyano-5,5-dimethyl-5H-furan-2-ylidene]malononitrile (100 mg, 0.33 mmol) and phenylacetylene (40 mg, 0.40 mmol) in 15 mL ethanol was stirred at 50° C. under N$_2$. Sodium ascorbate (20 mg, 0.10 mmol in 2 ml water) solution was added followed by copper sulfate (12 mg, 0.048 mmol, 2 mL water) solution and stirred at 50° C. for 24 h. The reaction mixture was cooled, poured into cold water (100 mL) and was stirred at room temperature for 1 h. The precipitate formed was filtered off and air-dried. The crude product was further purified by recrystallization from EAC/1-propanol, Yield: 70 mg (52%) mp: 280° C. IR (neat) 3097, 2232, 1645, 1530 cm$^{-1}$: $^1$H NMR (400 MHz, DMSO) δ 9.46 (s, 1H), 8.24 (d, J=8.8 Hz, 2H), 8.06 (d, J=8.8 Hz, 1H), 7.95-7.97 (m, 3H), 7.41-7.54 (m, 3H), 1.80 (s, 6H); $^{13}$C NMR (DMSO) δ 176.68, 176.52, 149.83, 147.27, 139.40, 130.17, 129.45, 128.86, 128.08, 126.9, 125.20, 120.34, 111.88, 111.00, 110.58, 103.71, 100.49, 54.80, 24.40; Anal. Calcd for C$_{24}$H$_{16}$N$_6$O: C, 71.28; H, 3.99; N, 20.78. Found: C, 71.58; H, 3.84; N, 20.64. UV-Vis(CH$_2$Cl$_2$): $\lambda_{max}$=369 nm, $\epsilon$=2.05×10$^4$ L.mol$^{-1}$cm$^{-1}$.

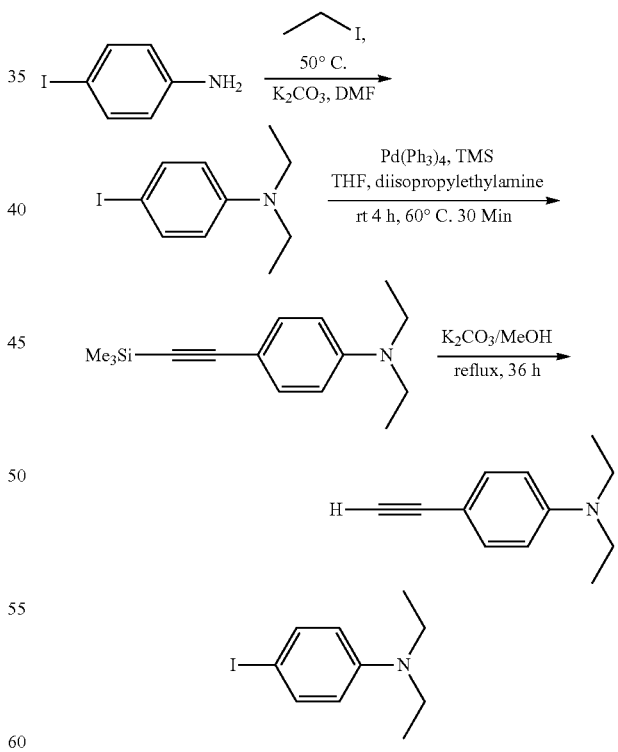

N,N-Diethyl-4-iodo-aniline (RS01056)

In a 250 mL two necked flask, a mixture of 4-iodoaniline (7 g, 31.9 mmol) and potassium carbonate (13.27 g, 96 mmol) was dissolved in dry DMF (50). The mixture was stirred for 10 min subsequently ethyl iodide (7.6 mL, 96 mmol) was added. The resulting mixture was stirred at 50° C. for 24 h, cooled to rt and poured into water. The product was extracted with ethyl acetate, washed with water, dried over anhydrous magnesium sulfate and the solvent was removed by rotary evaporation. The crude product was further purified by silica gel column chromatography using hexane eluent. The liquid product separated was used directly in the next step. Yield 6.5 g (74%). IR (neat) 2969, 1622, 1587, 1553 cm$^{-1}$; $^1$H NMR (400 MHz, CDCl$_3$) et 7.42 (d, J=8.8 Hz, 2H), 6.44 (d, J=8.8 Hz, 2H), 3.30 (q, J=72 Hz, 4H), 1:15 (t, J=6.8 Hz, 6H); $^{13}$CNMR (100 MHz, CDCl$_3$) δ 147.17 137.67, 114.01, 75.54, 44.30, 12.36.

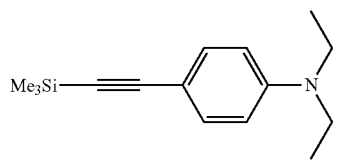 [SMILES: CCN(CC)c1ccc(C#C[Si](C)(C)C)cc1]

N,N-Diethyl-(4-trimethylsilanylethynylphenyl) amine (RS01058)

To an oven dried flask fitted with a magnetic stir bar and condenser, Pd(PPh$_3$)$_4$ (207 mg, 0.18 mind) and cuprous iodide (115 mg, 0.6 mmol) was added and the system was evacuated and back flushed with N$_2$. Dry THF (25 mL) was added, subsequently N,N-diethyl-(4-iodophenyl)amine (1 g, 3.6 mmol in THF) and dry degassed diisopropylethylamine (2.5 mL, 14.5 mmol) stirred for 10 min. Trimethylsitylacetylene (0.85 mL, 6 mmol) was added and the mixture was stirred at room temperature for 4 h and then at 80° C. for 30 min. The reaction mixture was cooled to room temperature, poured into ice water and stirred at it for 1 h. The mixture was extracted with ethyl acetate (50×3), the combined organic layer was washed with saturated ammonium chloride solution and was dried over anhydrous magnesium sulfate. The solvent was removed by rotary evaporation and the crude product was purified by silica gel column chromatography using hexane/EAC (0-5%) as eluent, Yield: 0.54 g. (61%). IR (neat) 2958, 2857, 2145, 1605, 1515, 1468, 1401 cm$^{-1}$; $^1$H NMR (400 MHz, CDCl$_3$) 7.37 (d, J=8.8 Hz, 2H), 6.57 (d, J=8.8 Hz, 2H), 3.37 (q, 7.2 Hz, 4H), 1.19 (t, 6.8 Hz, 6H), 0.32 (s, 9H); $^{13}$CNMR (100 MHz, CDCl$_3$) δ 147.41, 133.14, 110.81, 108.66, 106.77, 90, 43, 44.09, 12.35.

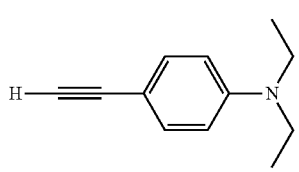

N,N-Diethyl-(4-ethynylphenyl) amine (RS01066) (for type [II])

A mixture of N,N-diethyl-(4-trimethylsilanylethynyl-phenyl)amine (500 mg 2.03 mmol), K$_2$CO$_3$ (1.5 g 10.8 mmol) and methanol (30 mL) was stirred at 65° C. for 30 h. The reaction mixture was cooled, poured into water and extracted with ethyl acetate (50×3). The combined extract was dried over anhydrous MgSO$_4$. The solvent was removed under reduced pressure and the crude material was further purified by filtration through a short silica gel column with hexane/EAC (0-5%) and the product separated as a semi solid. Yield: 250 mg (72.2%) IR (neat) 2971, 2098, 1607, 1551 cm$^{-1}$; $^1$H NMR (400 MHz, CDCl$_3$) δ7.36 (d, J=8.4 Hz, 2H), 6.59 (d, J=8.4 Hz, 2H), 3.36 (q, J=6.8 Hz, 4H), 1.16 (t, 6.8 Hz, 6H); $^{13}$CNMR (100 MHz, CDCl$_3$) δ 147.68, 133.31, 110.90, 107.46, 84.96, 74.38, 44.19, 12.41.

P-N,N-Diethylazidoaniline (RS01070) (for type [I])

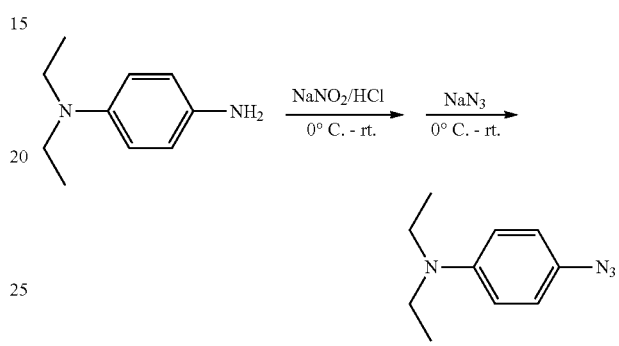

A solution of NaNO$_2$ (2.07 g, 30 mmol) in 20 mL water was added drop wise to a solution of (4-amino phenyl) diethyl amine (2.0 g, 12 mmol) in 60 mL 4M HCl at 0-5° C. The mixture was stirred at this temperature for 45 min. A solution of NaN$_3$ (1.5 g, 23 mmol) in 20 mL water was slowly added to the mixture at the same temperature. Stirring was continued for 30 min below 5° C. and then overnight at room temperature. The solution was extracted with dichloromethane (50×2) and dried over anhydrous MgSO$_4$. The solvent was removed by rotary evaporation and the solid separated was recrystallized from dichloromethane/methanol. The product obtained as white solid. Yield: 500 mg (87%). mp: 145° C.; $^1$H NMR (400 MHz, CDCl$_3$) δ 7.70 (id, Hz 2H) 7.11 (d, J=8.4 Hz, 2H), 3.60 (bs, 2H), 3.24 (bs, 2H), 1.24 (t, 7. Hz, 6H); $^{13}$C NMR (100 MHz, CDCl$_3$) δ 142.17, 133.51, 124.26, 120.64, 53.67, 10.23, IR (neat,); 2977, 2121, 1604, 1312, 1275 cm$^{-1}$. Anal. Calcd for C$_{10}$H$_{14}$N$_4$: C, 63.13; H, 7.42; N, 29.45 Found: 63.48; H, 7.31; N, 29.24.

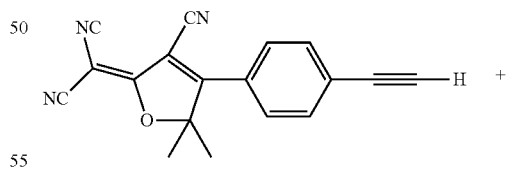

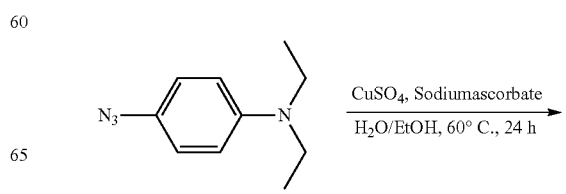

-continued

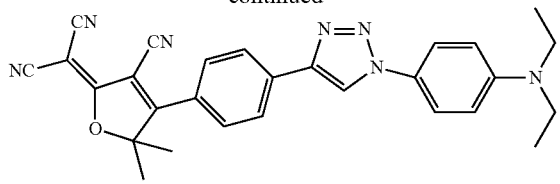

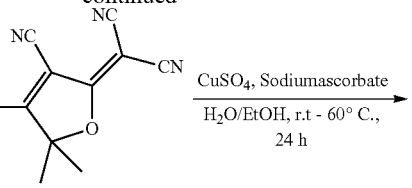

2-{3-Cyano-4-{4-[1-(4-diethylamino-phenyl)-1H-[1,2,3]triazol-4-yl)phenyl}5,5-dimethyl-6H-furan-2-ylidene}malononitrile (RS01065) (type [I])

To a mixture of 2-[3-cyano-4-(4-ethynyl-phenyl)-5,5-dimethyl-5H-furan-2-ylidene]malononitrile (80 mg, 0.31 mmol) and p-N,N-diethylazidoaniline (60 mg, 0.31 mmol) in ethanol (20 mL) was stirred at 60° C. under $N_2$. Sodium ascorbate (25 mg, 0.12 mmol in 1 mL water) solution and copper sulfate (12 mg, 0.05 mmol in 2 mL water) solution was added respectively. The mixture was continued to stirred at 60° C. for 24 h, cooled, poured into cold water, stirred at room temperature for 30 min and the precipitate formed was filtered off and air dried. The product was further purified by silica gel column chromatography using hexane/EAC 30-50% and the solid product obtained was finally recrystallized from dichloromethane/methanol. Yield: 115 mg (82%) Mp: 265° C.; IR (neat) 3012, 2950, 2228, 1610, 1582 $cm^{-1}$; $^1$H NMR (400 MHz, $CDCl_3$) δ 8.16 (s, 1H), 8.08 (d, J=8.8 Hz 2H), 7.88 (d, J=8.8 Hz, 2H), 7.51 (d, J=8.8 Hz, 2H), 6.71 (d, J=8.8 Hz, 2H), 3.40 (q, 7.2 Hz, 4H), 1.83 (s, 6H), 1.16 (t, J=7.2 Hz, 6H); $^{13}$CNMR ($CDCl_3$) δ176.33, 174.93, 148.01, 145.37, 136.27, 128.97, 126.43, 126.47, 125.90, 121.96, 118.81, 111.32, 111.27, 111.11, 110.18, 100.78, 98.85, 59.85, 44, 30, 26.31, 12.16. Anal, Calcd for $C_{28}H_{25}N_7O$: C, 70.72; H, 5.30; N, 20.62. Found: C, 70.58; H, 5.18; N, 20.98; $\lambda_{max}$ ($CH_2Cl_2$)= 379 nm. UV-Vis($CH_2Cl_2$): $\lambda_{max}$=379 nm $\epsilon$=1.92×10$^4$ L.$mol^{-1}$ $cm^{-1}$.

2-(3-Cyano-4-{4-[4-(4-diethylamino-phenyl)-[1,2,3]triazol-1-yl]phenyl}5,5-dimethyl-5H-furan-2-ylidene)malononitrile (RS01071) (type [II])

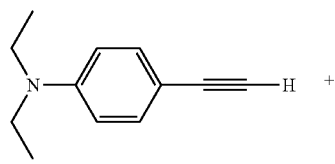

To a mixture of 2-[4-(4-azidophenyl)-3-cyano-5,5-dimethyl-5H-furan-2-ylidene]malononitrile (60 mg, 0.20 mmol) and diethyl-(4-ethynyl-phenyl) amine (35 mg, 0.20 mmol) in ethanol (10 mL) was stirred at 60° C. Sodium ascorbate (14 mg, 0.07 mmol in 1 mL water) solution was added followed by copper sulfate (8 mg, 0.03 mmol in 1 mL water) solution. The mixture was stirred at 60° C. for 24 h, cooled, poured into cold water and was stirred at room temperature for 1 h. The precipitate formed was filtered off and air dried. The product was further purified by silica gel column chromatography using hexane/EAC 30-50% and finally recrystallized from dichloromethane/methanol. Yield: 70 mg (73%) Mp: 275° C. IR (neat) 3022, 2230, 1620 $cm^{-1}$; $^1$H NMR (400 MHz, $CDCl_3$) 8.09 (s, 1H), 8.05 (d, J=8.8 Hz, 2H), 7.93 (d, J=8.8 Hz, 2H), 7.72 (d, J=8.8 Hz, 2H), 6.73 (d, J=8.8 Hz, 2H), 3.40 (q, 4H), 1.83 (s, 6H), 1.18 (t, 6.8 Hz, 6H); $^{13}$CNMR ($CDCl_3$) δ 175.44, 174.40, 149.64, 147.93, 140.30, 129.83, 128.81, 126.91, 126.14, 120.32, 115.77, 114.36, 110.77, 110.79, 109.99, 102.25, 98.91, 59.89, 44.11, 26.07, 12.30. Anal. Calcd for $C_{28}H_{25}N_7O$: C, 70.72; H, 5.30; N, 20.62. Found: C, 69.33; H, 5.63; N, 20.87. UV-Vis($CH_2Cl_2$): $\lambda_{max}$=319 nm $\epsilon$=3.562×10$^4$ L.$mol^{-1}$$cm^{-1}$.

Spectroscopic Data for 1,2,3-Triazole Derivatives and Precursors

| structure | type | properties |
|---|---|---|
| 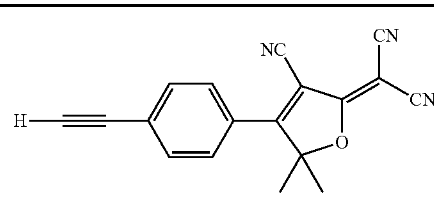 | [I] | (RS01039)<br>λmax 357 nm<br>2.25E4 L/molcm<br>λ cutoff 450 nm |

Spectroscopic Data for 1,2,3-Triazole Derivatives and Precursors

| structure | type | properties |
|---|---|---|
| (structure) | [II] | (RS01031; NL00006) $\lambda$max 384 nm 2.90E4 L/molcm $\lambda$ cutoff 460 nm |
| (structure) | [I] | (RS02011) $\lambda$max 384 nm 3.01E4 L/molcm $\lambda$ cutoff 460 nm |
| (structure) | [II] | (RS01057) $\lambda$max 369 nm 2.05E4 L/molcm $\lambda$ cutoff 460 nm |
| (structure) | [I] | (RS01086) $\lambda$max 384 nm 3.22E4 L/molcm $\lambda$ cutoff 470 nm |
| (structure) | [II] | (RS01071) $\lambda$max 319 (360) nm 3.56E4 L/molcm $\lambda$ cutoff 550 nm |
| (structure) | [I] | (RS01065) $\lambda$max 379 nm 1.90E4 L/molcm $\lambda$ cutoff 520 nm (600 nm in polymer film) |

Figure 28:
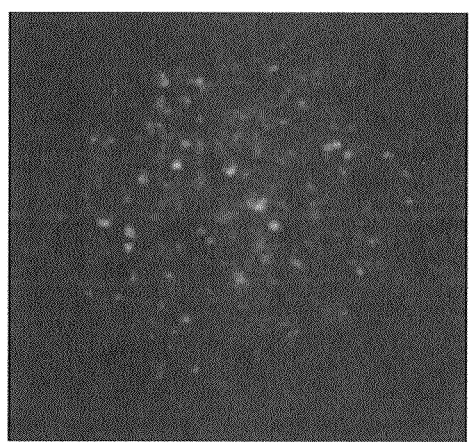
FIG. 28 illustrates the emission from single molecules of RS01065 when excited at 488 nm in a PMMA polymer film; read and orange emission is visible from many molecules

When pumped at 488 nm, the molecule of Formula 18 (RS01039) emits weakly at 500 nm. To demonstrate the generation of long-wavelength fluorescence, a click reaction was performed with 4-dithylaminophenylacetylene and copper catalyst. The fluorescence of the triazole product (Formula 18A, (RS01065) is red-shifted to about 600 nm in a polymer, dramatically different from either of the starting materials. The image in FIG. 28 shows the emission from single molecules of RS01065 when excited at 488 nm in a PMMA polymer film; red and orange emission is visible from many molecules.

| structure | type | properties |
|---|---|---|
| (structure) | [I] | (RS01065) $\lambda$max 379 nm 1.90E4 L/molcm $\lambda$ cutoff 520 nm (600 nm in polymer film) |

Red and orange fluorescence of single molecules of fluorophore RS01065 in PMMA when pumped at 488 nm. Neither of the precursors shows significant red or orange fluorescence when pumped at this wavelength and as such function as fluorogens.

Labeling

Any of the above described fluorogen or fluorophore compounds (P-ATA, T-ATA, or T-AAT) can be used for labeling and visualizing biomolecules and biological structures. The methods of use can involve in vitro applications or in vivo applications.

Biomolecules that can be labeled include DNA, RNA, monosaccharides, polysaccharides, nucleotides (ATP, GTP, cAMP), lipids, peptides, and proteins (including enzymes and other structural proteins). Biological structures such as lipid bilayers, membranes, micelles, transmembrane proteins, ribosomes, liposomes, nucleosomes, peroxisomes, cytoskeletal units, plastids, chloroplasts, or mitochondria, can also be labeled using the fluorophore compounds. The biomolecules and biological structures can interact with the fluorophore compounds in a variety of manners. For example, the interaction can be through a covalent bond, through an ionic bond, through a pi-pi stacking interaction, through hydrophobic interactions, through amphiphilic interactions, through van der Waals interactions, fluorophore-fluorophore interactions, and so on. The interaction can be reversible or irreversible. The interaction can be with the surface of the biomolecules and biological structures, or the fluorophore compound can interact with an interior cavity, binding site, or other available structure or space.

Fluorophore compounds can be designed and selected for their ability to form covalent bonds with various biological molecules. For example, fluorophore compounds containing maleimide, acetamide, or methanethiosulfonate groups can covalently react with thiol groups such as found in protein or peptide cysteine residues. N-hydroxy-succinimide groups can be used to covalently attach, to amine groups such as found in protein or peptide lysine groups. Phosphoramidite groups can be used to covalently attach the fluorophore compounds to nucleic acids such as DNA or RNA.

Besides super-resolution imaging, the azido push-pull fluorogens for P-ATA could be applied to other biological imaging schemes. For instance, photoaffinity labeling (PAL) requires a chemically inert binding molecule that becomes reactive upon illumination; the reactive photoproduct forms a covalent bond to a biomolecule to which it is bound or near. Thus a fluorogenic PAL, can be produced, i.e. a dark ligand that can both become fluorescent and bioconjugated in one illumination step. Moreover a nonspecific fluorogenic PAL can be produced.

Labeling methods can involve contacting the biomolecules with at least one fluorophore compound under conditions suitable for labeling. Typically, the labeling will be performed in a liquid solution with other chemical agents present. The additional chemical agents can include salts, buffers, detergents, and so on. The liquid solution can also include water and/or other solvents such as methanol, ethanol, dimethylsulfoxide (DMSO), and tetrahydrofuran (THE).

The in vivo applications can involve contacting the fluorophore compound with cells suspended in culture, with cells immobilized on a surface, with a slice of tissue, with a monolayer of cells, with a tissue, or with an intact organism. For example, the fluorophore compounds may directly insert into the membrane of the cell or pass through the membrane into the cytoplasm. The in vivo applications can further comprise a step of enhancing the ability of the target cells to uptake the fluorophore compound. The enhancing step can comprise treating the cells with a detergent, treating the cells with dimethylsulfoxide (DMSO), treating the cells with one or more pulses of an electrical charge (electroporation), or treating the cells briefly with osmotic shock. Alternatively, the contacting step can comprise direct injection of the fluorophore compound into the cell using a micropipette or other syringe devices.

The liquid solution can generally be at any pH compatible with the biomolecule and the fluorophore compound. For example, the pH can be about 5, about 5.5, about 6, about 6.5, about 7, about 7.5, about 8, about 8.5, about 9, and ranges between any two of these values.

The liquid solution can generally be at any temperature compatible with the biomolecule and the fluorophore compound. Typically, the liquid solution will be at a temperature of about 0° C. to about 50° C. Temperatures can be about 0° C., about 5° C., about 10° C., about 15° C., about 20° C., about 25° C., about 30° C., about 35° C., about 40° C., about 45° C., about 50° C., and ranges between any two of these values.

The contacting step can generally be performed for any suitable length of time. For example, the contacting step can be performed for about 1 minute, about 2 minutes, about 3 minutes, about 4 minutes, about 5 minutes, about 10 minutes, about 20 minutes, about 30 minutes, about 40 minutes, about 50 minutes, about 1 hour, about 2 hours, about 3 hours, about 4 hours, about 5 hours or longer, or ranges between any two of these values.

The methods of use can further comprise a purification step performed after the contacting step. The purification step can comprise separating unbound fluorophore compound from fluorophore compound bound to the biomolecules. The purification step can comprise the use of chromatography (such as agarose gel electrophoresis, polyacrylamide gel electrophoresis ("PAGE"), SDS polyacrylamide gel electrophoresis ("SDS-PAGE"), isoelectric focusing, affinity chromatography, size-exclusion chromatography, separation with magnetic particles, ELISA, HPLC, FPLC, centrifugation, density gradient centrifugation, dialysis, or osmosis.

The methods of use can further comprise visualizing the fluorophore compound bound to the biomolecules. The visualization can be performed by illumination by a light source followed by epifluorescence microscopy, by total internal reflection fluorescence microscopy, by confocal microscopy, by two-photon or mufti-photon excitation microscopy, by second-harmonic imaging microscopy, by polarization microscopy, or by aperture-based or apertureless near-field optical microscopy. The methods of use can further comprise quantifying the fluorophore compound bound to the biomolecules. The quantification can be performed by counting detected photons in a time interval, by pumping the fluorophore with light of different polarizations, by measuring the polarization of the detected photons, by measuring the anisotropy of the detected photons, by measuring the spectrum of the detected photons, by measuring the lifetime of the detected photons, or by measuring the correlations of the detected photons. Correlations can be measured by fluorescence correlation spectroscopy, by start-stop coincidence counting, by using hardware autocorrelators, or by time-tagging the emission time of each photon with respect to the time of a pumping light pulse followed by off-line computation.

While in accordance with the patent statutes the best mode and preferred embodiment have been set forth, the scope of the invention is not intended to be limited thereto, but only by the scope of the attached claims.

What is claimed is:

1. A label comprising:
a fluorophore covalently linked to a biomolecule, wherein said biomolecule comprises a DNA, RNA, monosaccharide, polysaccharide, nucleotide (ATP, GTP, cAMP), lipid, peptide, or a protein including enzyme and other structural proteins, or any combination thereof;
wherein said fluorophore is derived from a photoactivatable fluorogen, said photoactivatable fluorogen comprising an azide conjugated covalently to an acceptor group through a pi-conjugated system (pi-bridge);
wherein said fluorophore is derived from said photoactivatable fluorogen by a photochemical conversion whereby said azide group is converted to an amine donor group and wherein said fluorophore comprises said amine donor group conjugated covalently to said acceptor group through said pi-bridge so that an electron from the amine donor can be delocalized to said acceptor group through said pi-bridge;
wherein said pi-bridge of said fluorogen is a conjugated system and is derived from one or more contiguous alkenes each, independently, containing from 2 to about 12 carbon atoms, or wherein said one or more contiguous alkenes is a replaced —(CH=N)— unit, or wherein said one or more contiguous alkenes are substituted with an aliphatic group containing from 1 to about 18 carbon atoms;
or is derived from one or more alkynes each, independently, containing from 2 to about 12 carbon atoms;
or is derived from one or more aromatic or heterocyclic aromatic or mono or polysubstituted aromatic or heterocyclic wherein each, independently, aromatic group has from 3 to about 26 total ring atoms, or each, independently, heterocyclic aromatic group has from 3 to 26 total ring atoms and from 1 to 3 nitrogen, oxygen, sulfur, phosphorus, or selenium atoms, and wherein each substituent, independently, is a) one or more alkyl groups having a total of from 1 to about 18 carbon atoms, or b) is one or more alkene groups having a total of from 2 to about 4 carbon atoms, or c) one or more alkyne groups having a total of from 2 to 10 carbon atoms; or d) is an unsubstituted heterocyclic group having a total of from 3 to about 26 carbon atoms, and, independently, from 1 to 3 nitrogen, oxygen, sulfur, phosphorus, or selenium atoms; or e) wherein said substituent is one or more halides; or f) wherein said substituent can be connected to 2 or more of said aromatic groups; or
any combination of the preceding;
wherein said acceptor group of said fluorophore is

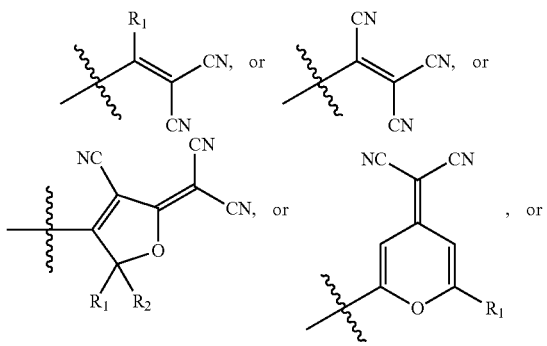

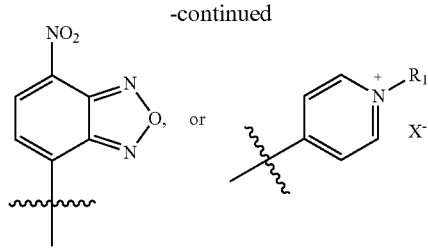

pyridinium wherein $R_1$ is not H and X— is a counterion, or

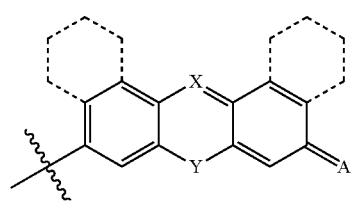

$X = CR_1, N$
$Y = NR_2, O, S, or CR_3R_4$
$A = O, or N^+R_5R_6$ where $R_3$, $R_4$, $R_5$, and $R_6$, each, independently, can be the same as $R_1$ or $R_2$, except that $R_5$ and $R_6$ can be combined as a cycloaliphatic group; or

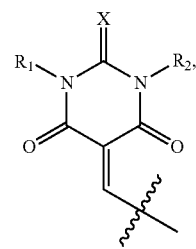

$X = O, or S$ or any combination thereof, and
wherein said $R_1$ and said $R_2$, independently, comprises H; or, an alkyl group having from 1 to about 18 carbons; or an aryl group having from 4 to about 14 carbon atoms; or an aromatic heterocyclic group containing one or more of oxygen, nitrogen, or sulfur atoms and from 4 to about 14 carbon atoms, or any combination thereof; or an alkene or an alkyne group each, independently, containing from 2 to about 18 carbon atoms; or wherein said alkyl, alkene, alkyne, or said aromatic heterocyclic group, aryl group, each, independently and optionally, contain a functional group comprising an ether, an amine, a cyano, an alcohol, a carboxylic acid, or a sulfonic acid, or any combination thereof;
wherein said pi-bridge of said fluorophore is the same as said pi-bridge of said fluorogen, and wherein said acceptor group of said fluorophore is the same as said acceptor group of said fluorogen; and
wherein said fluorophore is excitable at a wavelength of greater than about 440 nanometers.

2. A label comprising the conjugated covalently linked fluorophore-biomolecule according to claim 1, wherein with respect to said pi group said one or more aromatic or heterocyclic aromatic or mono or polysubstituted aromatic or heterocyclic aromatic groups each, independently, contains from about 5 to about 14 total ring atoms, wherein said one or more substituent alkyl groups each, independently, contains from 1 to 8 carbon atoms, and wherein said heterocyclic aromatic group ring contains one or more of only said nitrogen, oxygen, or sulfur atoms therein.

3. A label comprising the conjugated covalently linked fluorophore-biomolecule according to claim 2, wherein said one or more electron accepting groups is bonded to one or more alkenes, independently, having from 2 to 20 carbon atoms or bonded to at least one other electron accepting group through one or more alkenes, or one or more heterocyclic aromatic rings containing one or more nitrogen atoms and/or one or more oxygen atoms; or any combination thereof, and wherein said azide group is derived from an azide having the formula R-N3 where R comprises an aromatic having one or more rings, or a substituted aromatic wherein said substituted group is an aliphatic having from 1 to about 12 carbon atoms, or a heterocyclic containing a total of 3 to about 12 atoms with one or more atoms being O, S, N, or a halide, or a combination thereof.

4. A label comprising a conjugated covalently linked fluorophore-biomolecule according to claim 1, wherein said fluorophore is a compound comprising

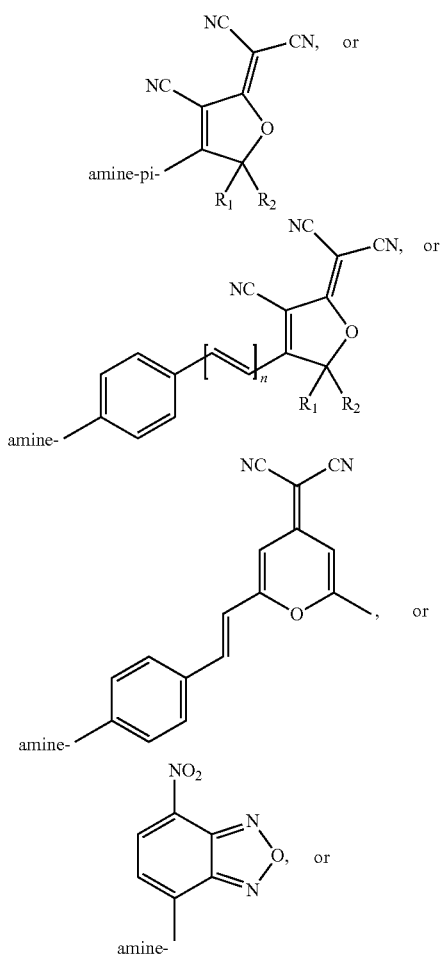

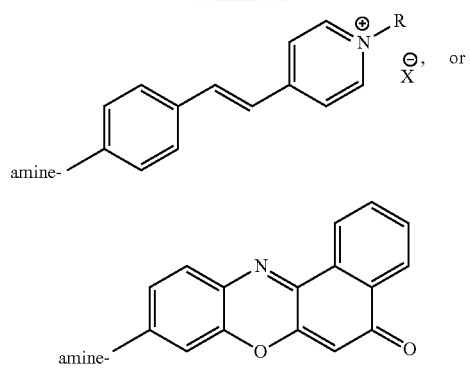

wherein n is 0, or 1 to about 4, wherein said $R_1$ and said $R_2$, independently, comprises H; or, an alkyl group having from 1 to about 18 carbons; or an aryl group having from 4 to about 14 carbon atoms; or an aromatic heterocyclic group containing one or more of oxygen, nitrogen, or sulfur atoms and from 4 to about 14 carbon atoms, or any combination thereof; or an alkene or an alkyne group each, independently, containing from 2 to about 18 carbon atoms; or wherein said alkyl, alkene, alkyne, or said aromatic heterocyclic group, aryl group, each, independently and optionally, contain a functional group comprising an ether, an amine, a cyano, an alcohol, a carboxylic acid, or a sulfonic acid, or any combination thereof, wherein said amine end group comprises —$NH_2$, H-alkyl-N—, dialkyl-N—, H-phenyl-N—, diphenyl-N—, wherein said alkyl group, independently, contains from 1 to about 15 carbon atoms and can be linear, branched, or functionalized, wherein said phenyl group, independently, can be substituted and contain from 1 to about 15 carbon atoms, or wherein an organic heterocyclic group having a total of from 3 to about 12 atoms can be substituted on said nitrogen atom and optionally include one or more O, S, or N atoms, or wherein said nitrogen atom is part of a ring.

5. A label comprising a conjugated covalently linked fluorophore-biomolecule according to claim 2, wherein said fluorophore is a compound comprising

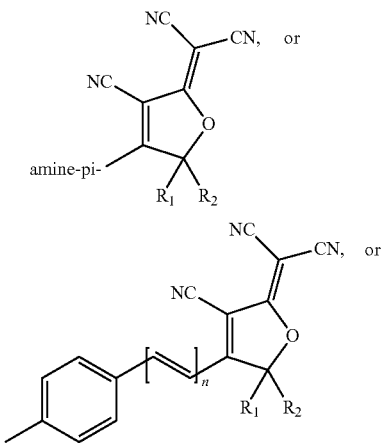

-continued

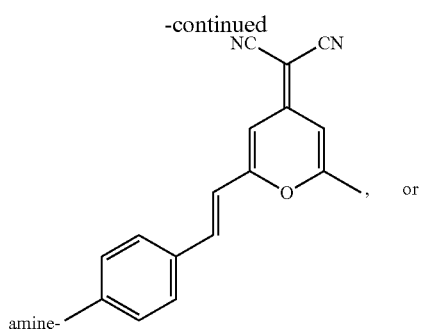

, or

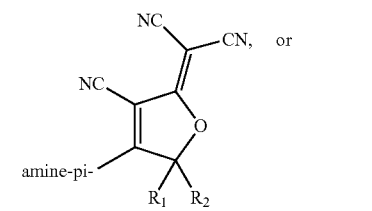

6. A label comprising a conjugated covalently linked fluorophore-biomolecule according to claim 3, wherein said fluorophore is a compound comprising

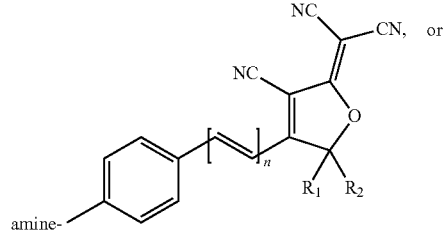

, or

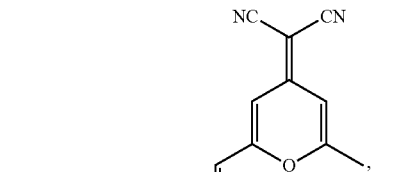

, or

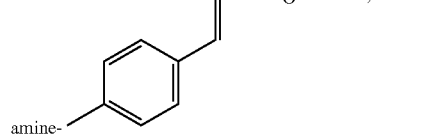

, or

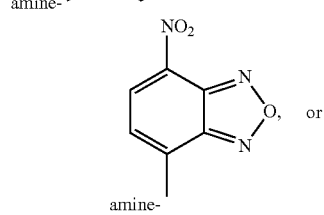

wherein n is 0, or 1 to about 4, wherein said $R_1$ and said $R_2$, independently, comprises H; or, an alkyl group having from 1 to about 18 carbons; or an aryl group having from 4 to about 14 carbon atoms; or an aromatic heterocyclic group containing one or more of oxygen, nitrogen, or sulfur atoms and from 4 to about 14 carbon atoms, or any combination thereof; or an alkene or an alkyne group each, independently, containing from 2 to about 18 carbon atoms; or wherein said alkyl, alkene, alkyne, or said aromatic heterocyclic group, aryl group, each, independently and optionally, contain a functional group comprising an ether, an amine, a cyano, an alcohol, a carboxylic acid, or a sulfonic acid, or any combination thereof, wherein said amine end group comprises —NH$_2$, H-alkyl-N—, dialkyl-N—, H-phenyl-N—, diphenyl-N—, wherein said alkyl group, independently, contains from 1 to about 15 carbon atoms and can be linear, branched, or functionalized, wherein said phenyl group, independently, can be substituted and contain from 1 to about 15 carbon atoms, or wherein an organic heterocyclic group having a total of from 3 to about 12 atoms can be substituted on said nitrogen atom and optionally include one or more O, S, or N atoms, or wherein said nitrogen atom is part of a ring.

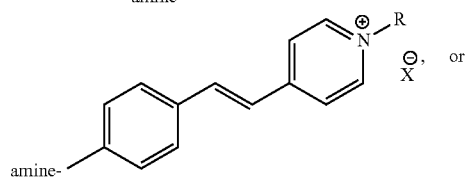

, or

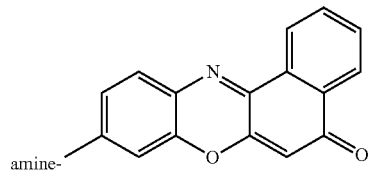

wherein n is 0, or 1 to about 4, wherein said $R_1$ and said $R_2$, independently, comprises H; or, an alkyl group having from 1 to about 18 carbons; or an aryl group having from 4 to about 14 carbon atoms; or an aromatic heterocyclic group containing one or more of oxygen, nitrogen, or sulfur atoms and from 4 to about 14 carbon atoms, or any combination thereof; or an alkene or an alkyne group each, independently, containing from 2 to about 18 carbon atoms; or wherein said alkyl, alkene, alkyne, or said aromatic heterocyclic group, aryl group, each, independently and optionally, contain a functional group comprising an ether, an amine, a cyano, an alcohol, a carboxylic acid, or a sulfonic acid, or any combination thereof, wherein said amine end group comprises —NH$_2$, H-alkyl-N—, dialkyl-N—, H-phenyl-N—, diphenyl-N—, wherein said alkyl group, independently, contains from 1 to about 15 carbon atoms and can be linear, branched, or functionalized, wherein said phenyl group, independently, can be substituted and contain from 1 to about 15 carbon atoms, or wherein an organic heterocyclic group having a total of from 3 to about 12 atoms can be substituted on said nitrogen atom and optionally include one or more O, S, or N atoms, or wherein said nitrogen atom is part of a ring.

7. A visualizable label comprising the composition of claim 1.

8. A visualizable label comprising the composition of claim 2.

9. A visualizable label comprising the composition of claim 3.

10. A visualizable label comprising the composition of claim 4.

11. A visualizable label comprising the composition of claim 5.

12. A visualizable label comprising the composition of claim 6.

* * * * *